(12) United States Patent
Aiguade Bosch et al.

(10) Patent No.: US 10,300,072 B2
(45) Date of Patent: May 28, 2019

(54) CYCLOHEXYLAMINE DERIVATIVES HAVING β2 ADRENERGIC AGONIST AND M3 MUSCARINIC ANTAGONIST ACTIVITIES

(71) Applicant: ALMIRALL, S.A., Barcelona (ES)

(72) Inventors: Jose Aiguade Bosch, Barcelona (ES); Silvia Gual Roig, Barcelona (ES); Maria Prat Quinones, Barcelona (ES); Carlos Puig Duran, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 15/668,817

(22) Filed: Aug. 4, 2017

(65) Prior Publication Data

US 2018/0015097 A1  Jan. 18, 2018

Related U.S. Application Data

(63) Continuation of application No. 14/956,767, filed on Dec. 2, 2015, now Pat. No. 9,757,383, which is a continuation of application No. 14/357,344, filed as application No. PCT/EP2012/072309 on Nov. 9, 2012, now Pat. No. 9,233,108.

(60) Provisional application No. 61/563,907, filed on Nov. 28, 2011.

(30) Foreign Application Priority Data

Nov. 11, 2011  (EP) .................................... 11382344

(51) Int. Cl.
| | |
|---|---|
| *C07D 403/12* | (2006.01) |
| *A61K 31/538* | (2006.01) |
| *C07D 413/14* | (2006.01) |
| *C07D 409/12* | (2006.01) |
| *C07D 409/14* | (2006.01) |
| *C07D 417/14* | (2006.01) |
| *A61K 31/4178* | (2006.01) |
| *A61K 31/423* | (2006.01) |
| *A61K 31/428* | (2006.01) |
| *A61K 31/4709* | (2006.01) |
| *A61K 45/06* | (2006.01) |
| *C07D 263/58* | (2006.01) |
| *C07D 401/12* | (2006.01) |
| *C07D 413/12* | (2006.01) |
| *C07D 417/12* | (2006.01) |
| *A61K 31/4184* | (2006.01) |

(52) U.S. Cl.
CPC ........ *A61K 31/538* (2013.01); *A61K 31/4178* (2013.01); *A61K 31/4184* (2013.01); *A61K 31/423* (2013.01); *A61K 31/428* (2013.01); *A61K 31/4709* (2013.01); *A61K 45/06* (2013.01); *C07D 263/58* (2013.01); *C07D 401/12* (2013.01); *C07D 403/12* (2013.01); *C07D 409/12* (2013.01); *C07D 409/14* (2013.01); *C07D 413/12* (2013.01); *C07D 413/14* (2013.01); *C07D 417/12* (2013.01); *C07D 417/14* (2013.01)

(58) Field of Classification Search
None
See application file for complete search history.

(56) References Cited

U.S. PATENT DOCUMENTS

| | | |
|---|---|---|
| 4,556,653 A | 12/1985 | Giani et al. |
| 5,397,800 A | 3/1995 | Alker et al. |
| 6,673,908 B1 | 1/2004 | Stanton |
| 9,072,734 B2 | 7/2015 | Mitsuyama et al. |
| 9,233,108 B2 | 1/2016 | Aiguade Bosch et al. |
| 9,315,463 B2 | 4/2016 | Prat Quinones et al. |
| 9,518,050 B2 | 12/2016 | Sole Feu et al. |
| 9,549,934 B2 | 1/2017 | Aiguade Bosch et al. |
| 9,562,039 B2 | 2/2017 | Julia Jane et al. |
| 9,579,316 B2 | 2/2017 | Julia Jane et al. |
| 9,643,961 B2 | 5/2017 | Prat Quinones et al. |
| 10,005,771 B2 | 6/2018 | Puig Duran et al. |
| 2009/0221664 A1 | 9/2009 | Ray et al. |
| 2012/0046467 A1 | 2/2012 | Mitsuyama et al. |
| 2013/0053359 A1 | 2/2013 | Prat Quinones et al. |
| 2013/0281415 A9 | 10/2013 | Prat Quinones et al. |
| 2014/0303127 A1 | 10/2014 | Bosch et al. |
| 2015/0329535 A1 | 11/2015 | Sole Feu et al. |
| 2016/0009698 A1 | 1/2016 | Julia Jane et al. |
| 2016/0015704 A1 | 1/2016 | Aparici Virgili et al. |
| 2016/0166566 A1 | 6/2016 | Julia Jane et al. |
| 2016/0175295 A1 | 6/2016 | Aparici Virgili et al. |
| 2016/0264557 A1 | 9/2016 | Prat Quinones et al. |

(Continued)

FOREIGN PATENT DOCUMENTS

| | | |
|---|---|---|
| CN | 101 44 572 | 9/2009 |
| EP | 0 147 475 | 10/1985 |
| EP | 1 078 629 | 2/2001 |

(Continued)

OTHER PUBLICATIONS

Brittain, Harry G., "Theory and Principles of Polymorphic Systems," Polymorphism in Pharmaceutical Solids, Second Addition, Drus and the Pharmaceutical Sciences, vol. 192, pp. 1-4, 15-19, 318-430 (2009).

(Continued)

*Primary Examiner* — Heidi Reese
(74) *Attorney, Agent, or Firm* — Finnegan, Henderson, Farabow, Garrett & Dunner, LLP

(57) ABSTRACT

The present invention relates to novel compounds having β2 adrenergic agonist and M3 muscarinic antagonist dual activity, to pharmaceutical compositions containing them, to the process for their preparation and to their use in respiratory therapies.

24 Claims, No Drawings

(56) References Cited

U.S. PATENT DOCUMENTS

2017/0275277 A1    9/2017  Puig Duran et al.

FOREIGN PATENT DOCUMENTS

| | | |
|---|---|---|
| EP | 1 894 568 | 3/2008 |
| EP | 2 386 555 | 11/2011 |
| EP | 2 426 121 | 3/2012 |
| EP | 2 592 077 | 5/2013 |
| EP | 2 592 078 | 5/2013 |
| JP | 2011-524897 | 9/2011 |
| JP | 2013-519705 A | 5/2013 |
| WO | WO 98/09632 | 3/1998 |
| WO | WO 99/30703 | 6/1999 |
| WO | WO 00/12067 | 3/2000 |
| WO | WO 01/14339 | 3/2001 |
| WO | WO 2004/074246 | 9/2004 |
| WO | WO 2004/074276 | 9/2004 |
| WO | WO 2004/074812 | 9/2004 |
| WO | WO 2004/106333 | 9/2004 |
| WO | WO 2004/089892 | 10/2004 |
| WO | WO 2005/080375 | 9/2005 |
| WO | WO 2005/111004 | 11/2005 |
| WO | WO 2005/123693 | 12/2005 |
| WO | WO 2006/023454 | 3/2006 |
| WO | WO 2006/023457 | 3/2006 |
| WO | WO 2006/023460 | 3/2006 |
| WO | WO 2007/017670 | 2/2007 |
| WO | WO 2007/090859 | 8/2007 |
| WO | WO 2007/107828 | 9/2007 |
| WO | WO 2008/000483 | 1/2008 |
| WO | WO 2008/017824 | 2/2008 |
| WO | WO 2008/017827 | 2/2008 |
| WO | WO 2008/041095 | 4/2008 |
| WO | WO 2008/087437 | 7/2008 |
| WO | WO 2008/096127 | 8/2008 |
| WO | WO 2008/096129 | 8/2008 |
| WO | WO 2008/149110 | 12/2008 |
| WO | WO 2009/013244 | 1/2009 |
| WO | WO 2009/017813 | 2/2009 |
| WO | WO 2009/098448 | 8/2009 |
| WO | WO 2009/139709 | 11/2009 |
| WO | WO 2009/154562 A1 | 12/2009 |
| WO | WO 2010/004517 | 1/2010 |
| WO | WO 2010/011813 | 1/2010 |
| WO | WO 2010/015792 | 2/2010 |
| WO | WO 2010/069504 | 6/2010 |
| WO | WO 2010/123766 | 10/2010 |
| WO | WO 2011/012897 | 2/2011 |
| WO | WO 2011/101374 A1 | 8/2011 |
| WO | WO 2011/141180 | 11/2011 |
| WO | WO 2012/044825 | 4/2012 |
| WO | WO 2012/085582 | 6/2012 |
| WO | WO 2012/085583 | 6/2012 |
| WO | WO 2012/168349 | 12/2012 |
| WO | WO 2012/168359 | 12/2012 |
| WO | WO 2013/068554 | 5/2013 |
| WO | WO 2013/068875 | 5/2013 |
| WO | WO 2013/071009 | 5/2013 |
| WO | WO 2013/071169 | 5/2013 |
| WO | WO 2014/086924 | 6/2014 |
| WO | WO 2014/086927 | 6/2014 |
| WO | WO 2014/095920 | 6/2014 |
| WO | WO2014095700 A1 | 6/2014 |
| WO | WO2014100158 A1 | 6/2014 |
| WO | WO 2014/031851 | 9/2014 |
| WO | WO 2014/131852 | 9/2014 |
| WO | WO 2015/011244 | 1/2015 |
| WO | WO 2015/011245 | 1/2015 |
| WO | WO2015049574 A1 | 4/2015 |
| WO | WO 2016/046390 | 3/2016 |

OTHER PUBLICATIONS

Banerjee, Rahul et al., "Saccharin Salts of Active Pharmaceutical Ingredients, Their Crystal Structures, and Increase water Solubilities," Crystal Growth and Design, vol. 5, No. 6, pp. 2299-2309 (2005).

Hughes, Adam D. et al., "Discovery of muscarinic acetylcholine receptor antagonist and beta 2 adrenoceptor agonist (MABA) dual pharmacology molecules," Bioorganic & Medicinal Chemistry Letters 21, pp. 1354-1358 (2011).

Milara J. et al., Neutrophil Activation in Severe, Early-Onset COPD Patients versus Healthy Non-Smoker Subjects in vitro: Effects of Antioxidant Therapy, Respiration (2012), 83, 147-158.

Nocker R. E. et al., Interleukin-8 in airway inflammation in patients with asthma and chronic obstructive pulmonary disease, International Archives of Allergy and Immunology, 1996, 109 (2): 183-91.

Paulekuhn, G. Steffen et al., "Trends in Active Pharmaceutical Ingredient Salt Selection based on Analysis of the Orange Book Database," J. Med. Chem, vol. 50, pp. 6665-6672 (2007).

Yamamoto C. et al., Airway inflammation in COPD assessed by sputum levels of interleukin-8*; Chest, 1997, 112 (2): 505-10.

Office Action dated Jun. 15, 2017 in U.S. Appl. No. 14/906,957.

Restriction Requirement dated Dec. 7, 2017, in U.S. Appl. No. 15/514,294.

Bannerjee, R. et al., "Synthon robustness in saccharinate salts of some substituted pyridines," CrystEngComm, 8, pp. 680-685 (2006).

Barnes, Peter J., "Airway Pharmacology," Textbook of Respiratory Medicine, $3^{rd}$ Edition, Chapter 11, 2000, pp. 267-272.

Bastin, R.J. et al., "Salt Selection and Optimisation Procedures for Pharmaceutical New Chemical Entities," Org. Process Res Dev, 4, pp. 427-435 (2000).

Bateman, E.D., "Pharmacodynamics of GSK961081, a bi-functional molecule, in patients with COPD," *Pulmonary Pharmacology & Therapeutics*, vol. 26, pp. 581-587 (2013).

Berge, S. et al., Pharmaceut. Sci., vol. 6691), pp. 1-19 (1977).

Chung, K.F., "p38 Mitogen-Activated Protein Kinase Pathways in Asthma and COPD," Chest, 139(6), pp. 1470-1479 (2011).

Glossop, Paul A. et al., "Progress in the Development of Inhaled, Long-Acting $\beta_2$-Adrenoceptor Agonists," Annual Reports in Medicinal Chemistry, vol. 41, pp. 237-248 (2006).

Hoffman, Brian B., "Catecholamines, Sympathomimetic Drugs, and Adrenergic Receptor Antagtonists," Goodman & Gilman's The Pharmacological Basis of Therapeutics, $10^{th}$ Edition, Chapter 10, pp. 215-232, (2001).

Hughes, A.D., "Discovery of Muscarinic Acetylcholine Receptor Antagonist and Beta-2 Adrenoceptor Agonist (MABA) Dual Pharmacology Molecules," Respiratory Drug Delivery Europe, pp. 47-58 (2013).

Hughes, A.D., et al., "Multivalent Dual Pharmacology Muscarinic Antagonist and β2 Agonist (MABA) Molecules for the Treatment of COPD, Progress in Medicinal Chemistry," vol. 51, pp. 71-95 (2012).

Hughes, Adam, et al., "Dual-pharmacology Muscarinic Antagonist and β2 Agonist Molecules for the Treatment of Chronic Obstructive Pulmonary Disease," Future Med. Chem., (2011), 3(13), pp. 1585-1605.

Jacobsen, John R., "Third-generation long-acting $\beta_2$-adrenoceptor agonists: medicinal chemistry strategies employed in the identification of once-daily inhaled $\beta_2$-adrenoceptor agonists," Future Med. Chem., 3(13), pp. 1607-1622 (2011).

McNamara, A., et al., "Preclinical Efficacy of THRX-200495, a Dual Pharmacology Muscarinic Receptor Antagonist and β2-Adrenoceptor Agonist (MABA)," Pulmonary Pharmacology & Therapeutics, 25 (5), pp. 357-363, (2012).

Miller-Larsson, A. et al., "Advances in Asthma and COPID Treatment: Combination Therapy with Inhaled Cortisoteroids and Long-Acting β2 Agonists," Curr Pharm Des. 12(25), pp. 3261-3279 (2006).

Naito, Ryo et al., "Synthesis and Antimuscarinic Properties of Quinuclidin-3-yl 1,2,3,4-Tetrahydroisoquinoline-2-carboxylate Derivatives as Novel Muscarinic Receptor Antagonists," J. Med. Chem., 2005, 48, pp. 6597-6606.

Norman, P., "Evaluation of WO-2012085582 and WO-2012085583 two identified MABAs: backups to AZD-2115?" Expert Opin. Ther. Patents, 22(11), pp. 1377-1383 (2012).

(56) References Cited

OTHER PUBLICATIONS

Norman, P., "Novel dihydroquinoline-based MABAs; clues to the identity of LAS-190792: evaluation of WO20111411802," Expert Opin. Ther. Patents, 22 (2), pp. 185-192 (2012).
Norris, v. et al., "Bronchodilation and safety of supratherapeutic doses of salbutamol or ipratroplum bromide added to single dose GSK961081 in patients with moderate to severe COPD," Pulmonary Pharmacology and Therapeutics, vol. 26, pp. 574-580 (2013).
P. Heinrich Stahl, Camille G. Wermuth. Handbook of Pharmaceutical Salts. Properties, Selection, and Use. Chapter 12, "Monographs on Acids and Bases", pp. 264-267, 283, 284, 290-293 and 300; Chapter 7, "A procedure for Salt Selection and Optimization", pp. 162-177 and 183-188; Chapter 2, "Solubility and Dissolution of Weak Acids, Bases and Salts"; pp. 19 and 28; Wiley-VCH; 2002.
Ray, Nicholas C. et al., "Muscarinic antagonist-β-adrenergic agonist dual pharmacology molecules as bronchodilators: a patent review," Expert Opinion on Therpeutic Patents, Informa Healthcare, vol. 19, No. 1, pp. 1-12 (2009).
Rogers, D.F., "Techykinin receptor antagonists for asthma and COPD," Expert Opin Ther Patents, 11(7): pp. 1097-1121 (2001).
Shan, W. et al. "Dual β2-adrenoceptor agonists-PDE4 inhibitors for the treatment of asthma and COPD," Bloorg Med. Chem Lett, 22: pp. 1523-1526 (2012).
Thorsson, L. et al., "Factors guiding the choice of delivery device of inhaled corticosteroids in the long-term management or stable asthma and COPD: Focus on budesonide," Respir Med., 99: pp. 836-849 (2005).
Van Noord, J.A., "Comparison of tiotropium once daily, formoterol twice daily and both combined once daily in patients with COPD," European Respiratory Journal, vol. 26, No. 2, pp. 214-222 (2005).
Wielders, Pascal L.M.L. et al., "A New class of bronchodilator improves lung function in COPD: a trial with GSK961081," Eur Respir J, 42: pp. 972-981 (2013).
International Search Report for International Application No. PCT/EP2011/002376, dated Aug. 1, 2011.
International Search Report for International Application No. PCT/EP2012/0072311, dated Dec. 10, 2012.
International Search Report for International Application No. PCT/EP2012/072309, dated Dec. 18, 2012.
International Search Report for International Application No. PCT/EP2013/076973, dated Mar. 11, 2014.
International Search Report for International Application No. PCT/2014/053871, dated Mar. 27, 2014.
International Search Report for International Application No. PCT/EP2014/053874, dated Apr. 17, 2014.
International Search Report for International Application No. PCT/EP2014/065966, dated Aug. 19, 2014.
International Search Report for International Application No. PCT/EP2014/065965, dated Sep. 18, 2014.
International Search Report of International Application No. PCT/EP2015/072158, dated Nov. 2, 2015.
Written Opinion of the International Searching Authority for International Application No. PCT/EP2015/072158.
Restriction Requirement dated Feb. 18, 2015, in U.S. Appl. No. 14/357,400.
Restriction Requirement dated Feb. 20, 2015, in U.S. Appl. No. 13/697,060.
Restriction/Election Requirement dated Feb. 11, 2016, for U.S. Appl. No. 14/770,200.
Restriction/Election Requirement dated Sep. 22, 2016, for U.S. Appl. No. 14/906,957.
Notice of Allowance dated Dec. 15, 2015, in U.S. Appl. No. 13/697,060.
Notice of Allowance dated Aug. 3, 2016, in U.S. Appl. No. 14/853,048.
Notice of Allowance dated Sep. 26, 2016, in U.S. Appl. No. 14/770,206.
Non-Final Office Action dated Aug. 4, 2015, for U.S. Appl. No. 13/697,060.
Non-Final Office Action dated Mar. 21, 2016, for U.S. Appl. No. 14/653,048.
Non-Final Office Action dated May 5, 2016, for U.S. Appl. No. 14/770,206.
Non-Final Office Action dated Jun. 10, 2016, for U.S. Appl. No. 14/770,200.
Non-Final Office Action dated Jul. 11, 2016, for U.S. Appl. No. 15/068,926.
Non-Final Office Action dated Aug. 11, 2016, for U.S. Appl. No. 14/906,991.
Final Office Action dated Nov. 30, 2016, for U.S. Appl. No. 14/770,200.
Office Action dated Apr. 3, 2018 in U.S. Appl. No. 14/906,957.
Office Action dated Dec. 27, 2018, in U.S. Appl. No. 14/906,957.
T-C Chou et al. Theoretical Basis, Experimental Design, and Computerized Simulation of Synergism and Antagonism in Drug Combination Studies. *Pharmacological Reviews*, vol. 58, pp. 621-681, 2006.

CYCLOHEXYLAMINE DERIVATIVES HAVING β2 ADRENERGIC AGONIST AND M3 MUSCARINIC ANTAGONIST ACTIVITIES

This application is a continuation of application Ser. No. 14/956,767, which is a continuation of application Ser. No. 14/357,344, filed May 9, 2014, which is a national stage filing under 35 U.S.C. § 371 of International Application No. PCT/EP2012/072309, filed Nov. 9, 2012, which claims priority to European Application No. 11382344.7, filed Nov. 11, 2011, and U.S. Provisional Application No. 61/563,907, filed Nov. 28, 2011. The contents of all four applications are incorporated herein by reference.

FIELD OF THE INVENTION

The present invention relates to novel compounds having β2 adrenergic agonist and M3 muscarinic antagonist dual activity. This invention also relates to pharmaceutical compositions containing them, process for their preparation and their use in respiratory therapies.

BACKGROUND OF THE INVENTION

Bronchodilator agents play an outstanding role in the treatment of respiratory disorders such as COPD and asthma. Beta-adrenergic agonists and cholinergic muscarinic antagonists are well established bronchodilator agents in widespread clinical use. Beta-adrenergic agonists currently used by the inhaled route include short-acting agents such as salbutamol (qid) or terbutaline (tid) and long-acting agents such as salmeterol and formoterol (bid). These agents produce bronchodilation through stimulation of adrenergic receptors on airway smooth muscle, reversing the bronchoconstrictor responses to a variety of mediators, such as acetylcholine. Inhaled muscarinic antagonists currently used include the short-acting ipratropium bromide or oxitropium bromide (qid) and the long-acting tiotropium (qd). These agents produce bronchodilation by reducing vagal cholinergic tone of airway smooth muscle. In addition to improve lung function, these agents also improve quality of life and reduce exacerbations. There are in the clinical literature a number of studies strongly demonstrating that the administration of a combination of a beta-2 agonist and a M3 antagonist is more efficacious for the treatment of COPD than either of the components alone (for example, van Noord, J. A., et al., Eur.Respir.J., 2005; 26: 214-222). Pharmaceutical compositions containing a combination of both types of bronchodilator agents are also known in the art for use in respiratory therapy. As an example, WO2009013244 discloses a medical composition containing salmeterol as beta-adrenergic agonist agent and tiotropium as antimuscarinic agent.

The class of beta2 adrenergic is well known and widely used by the persons skilled in the art, such as physicians, pharmacists or pharmacologists, for the treatment of respiratory disease, in particular asthma and chronic obstructive pulmonary disease (COPD) (Paul A. Glossop et al., Annual Reports in Medicinal Chemistry, 2007, 41, 237-248). Most of the beta2 adrenergic agonists are derivatives of natural catecholamines (e.g. epinephrine and norepinephrine) with which they share some common structural features, which are responsible for the similar interaction of these compounds with the beta 2 receptors ("Goodman & Gilman's The Pharmacological Basis of Therapeutics", 10th edition, chapter 10, pages 215-233, Textbook of respiratory medicine, third edition, Chapter 11, p. 267-272). In fact, most of the beta2 adrenergic agonist compounds have a general structure type that is present in the catechol (epinephrine and isoproterenol), namely an aminoethanol core flanked by an aryl group (J. R. Jacobsen, Future Medicinal Chemistry, 2011, 3 (13), 1607-1622). Examples of the aryl group that afford beta2 potency are but not limited to catechol, saligenin, formamide and 8-carbostyril groups (Paul A. Glossop et al., Annual Reports in Medicinal Chemistry, 2007, 41, 237-248).

Dual-pharmacology muscarinic antagonists-beta2 agonist (MABA) molecules present an exciting new approach to the treatment of respiratory disease by combining muscarinic antagonism and beta2 agonisn in a single entity. In the literature there have been disclosed various compounds having both muscarinic receptor antagonist and beta2-agonist activity (A. D. Hughes et al., Future Medicinal Chemistry, 2011, 3(13), 1585-1605). All of these molecules possess a great variety of covalent linker fragments between the M3 antagonist and the beta2 agonist moieties, indicating that the structure of the linker radical is not critical to preserve both activities, although such linker fragments has showed to be an important tool for modulating physical properties and potency at each target.

A single molecule possessing dual activity at muscarinic M3 and adrenergic β2 receptors (MABA) would therefore be desirable both in terms of efficacy and side-effects in the treatment of COPD. It would show also a relevant advantage in terms of formulation compared with the two-component combination. It also would be easier to co-formulate with other therapeutic agents such as inhaled anti-inflammatories to create triple therapy combinations. Thus there is a need for new compounds having both beta2 receptor agonist and muscarinic receptor antagonist activity and being suitable for the treatment of respiratory diseases, such as asthma and COPD.

SUMMARY OF THE INVENTION

The invention provides novel compounds that possess both β2 adrenergic receptor agonist and muscarinic receptor antagonist activities. Accordingly, there is provided a compound of formula (I), or pharmaceutically acceptable salts or N-oxides or solvates or deuterated derivatives thereof:

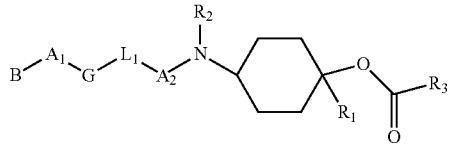

Formula (I)

Wherein

B is a moiety having a beta2-adrenergic binding activity, $R_1$ and $R_2$ independently are selected from the group consisting of a hydrogen atom and a linear or branched $C_{1-4}$ alkyl group, $R_3$ represents a group of formula:

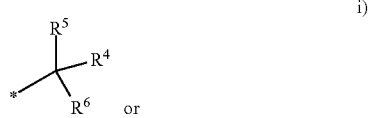

i)

or

-continued

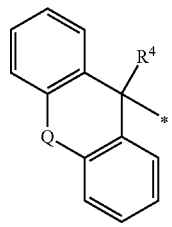

ii)

wherein:
- $R^4$ represents a hydrogen atom, a hydroxy group, a hydroxymethyl group or a linear or branched $C_{1-4}$ alkyl group,
- $R^5$ represents a saturated or unsaturated $C_{3-8}$ cycloalkyl group, a $C_{5-6}$ aryl group, a 5- to 6-membered heteroaryl group containing at least one heteroatom selected from N, S, and O; a $(C_{1-4}$ alkyl)-$(C_{5-6}$ aryl) group, a $(C_{1-4}$ alkyl)-$(C_{3-8}$ cycloalkyl) group or a $(C_{1-4}$ alkyl)-(5- to 6-membered heteroaryl group containing at least one heteroatom selected from N, S, and O) group, which groups independently are optionally substituted by one or more substituents $R^a$,
- $R^6$ represents a $C_{5-6}$ aryl group, a 5- to 6-membered heteroaryl group containing at least one heteroatom selected from N, S, and O, a saturated or unsaturated $C_{3-8}$ cycloalkyl group, a $C_{1-8}$ alkyl group, a $C_{2-8}$ alkenyl group, a $C_{2-8}$ alkynyl group, a $(C_{1-4}$ alkyl)-$(C_{5-6}$ aryl) group, a $(C_{1-4}$ alkyl)-$(C_{3-8}$ cycloalkyl) group or a $(C_{1-4}$ alkyl)-(5- to 6-membered heteroaryl group containing at least one heteroatom selected from N, S, and O) group, which groups independently are optionally substituted by one or more substituents $R^b$,
- $R^a$ and $R^b$ independently represent a halogen atom, a hydroxy group, $C_{1-4}$ alkyl group, $C_{1-4}$ alkoxy group, —SH, a $C_{1-4}$ alkylthio group, a nitro group, a cyano group, —CO$_2$R', —NR'R", —C(O)NR'R", —N(R''')C(O)—R', —N(R''')—C(O)NR'R", wherein R', R" and R''' each independently represents a hydrogen atom or a $C_{1-4}$ alkyl group, or R' and R" together with the nitrogen atom to which they are attached from a 3 to 6 membered heterocyclic ring.
- Q represents a direct bond, —CH$_2$—, —CH$_2$—CH$_2$—, —O—, —O—CH$_2$—, —S—, —S—CH$_2$—, —NH—, —NH—CH$_2$— or —CH=CH—,
- * represents the point of attachment of $R_3$ to the remainder of the molecule of formula (I),
- $A_1$ and $A_2$ independently are selected from the group consisting of a $C_{1-10}$ alkylene group, a $C_{2-10}$ alkenylene group and a $C_{2-10}$ alkynylene group, wherein said groups are optionally substituted with one or more substituents selected from a halogen atom, a hydroxy group, a linear or branched $C_{1-4}$ alkyl group, a linear or branched a $C_{1-4}$ alkoxy group, a $C_{5-6}$ aryl group and a $C_{3-7}$ cycloalkyl group,
- $L_1$ is selected from a direct bond, —O—, —NR$^c$—, —S—, —S(O)—, —SO$_2$—, —NR$^c$(CO)—, —(CO)NR$^c$—, —NR$^c$(CO)(CH$_2$)$_q$O—, —O(CH$_2$)$_q$(CO)NR$^c$—, —NR$^c$(CH$_2$)$_q$O—, —O(CH$_2$)$_q$NR$^c$—, —NR$^c$(CO)NR$^d$—, —C(O)—, —C(O)O—, —OC(O)—, —S(O)$_2$NR$^c$—, —NR$^c$S(O)$_2$—, —NR$^c$S(O)$_2$NR$^d$—, —C(O)NR$^c$S(O)$_2$— and —S(O)$_2$NR$^c$C(O)—, wherein $R^c$ and $R^d$ are independently selected form a hydrogen atom and a linear or branched $C_{1-4}$ alkyl group and q has a value of 0, 1 or 2,
- G is selected from the group consisting of a $C_{3-10}$ mono- or bicyclic cycloalkyl group, a $C_5$-$C_{14}$ mono- or bicyclic aryl group, a 3- to 14-membered saturated or unsaturated mono- or bicyclic heterocyclyl group having one or more heteroatoms selected from N, S and O, a 5- to 14-membered mono- or bicyclic heteroaryl group having one or more heteroatoms selected from N, S and O and a bicyclic ring system consisting of two monocyclic ring systems which are linked between each other by a covalent bond wherein said monocyclic ring systems are independently selected from a $C_{3-8}$ cycloalkyl group, a $C_5$-$C_6$ aryl group, a 3- to 8-membered saturated or unsaturated heterocyclyl group having one or more heteroatoms selected from N, S and O and a 5- to 6-membered heteroaryl group having one or more heteroatoms selected from N, S and O, wherein the cyclic groups independently are optionally substituted with one or more substituents selected from a halogen atom, a $C_{1-4}$ alkyl group, a $C_{1-4}$ alkoxy group, a carboxy, group, a cyano group, a nitro group, a hydroxy group, an oxo group, a trifluoromethyl group and a trifluoromethoxy group, with the proviso that when G is a phenyl group, $L_1$ is not one of the group selected from a direct bond, —O—, —NHC(O)—, —C(O)NH— and —NH(CO)O— group.

The invention also provides synthetic processes and intermediates described herein, which are useful for preparing compounds of the invention.

The invention further provides a pharmaceutical composition comprising at least a compound of the invention and a pharmaceutically-acceptable carrier.

The invention also provides a compound of the invention as described herein for use in the treatment of human or animal body by therapy.

The invention is also directed to the compounds as described herein, for use in the treatment of a pathological condition or disease associated with dual β2 adrenergic receptor and muscarinic receptor activities in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis, preferably asthma and chronic obstructive pulmonary disease.

The invention also provides the use of the compounds of the invention as described herein, for the manufacture of a medicament for the treatment of a pathological condition or disease associated with dual β2 adrenergic receptor and muscarinic receptor activities, in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis, preferably asthma and chronic obstructive pulmonary disease.

The invention is also directed to a method of treatment of a pathological condition or disease associated with dual β2 adrenergic receptor and muscarinic receptor activities, in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis, preferably asthma and chronic obstructive pulmonary disease, comprising administering a therapeutically effective amount of the compounds of the invention or a pharmaceutical composition of the invention to a subject in need of such treatment.

The invention also provides a combination product comprising (i) at least a compound of the invention as described herein; and (ii) one or more active ingredients selected from the group consisting of a corticosteroid and/or a PDE4 inhibitor, for simultaneous, separate or sequential use in the treatment of the human or animal body.

DETAILED DESCRIPTION OF THE INVENTION

When describing the compounds, compositions and methods of the invention, the following terms have the following meanings, unless otherwise indicated.

As used herein the term $C_1$-$C_4$ alkyl embraces linear or branched radicals having 1 to 4 carbon atoms. Examples include methyl, ethyl, n-propyl, i-propyl, n-butyl, sec-butyl and t-butyl radicals.

As used herein, the term $C_1$-$C_{10}$ alkylene embraces divalent alkyl moieties typically having from 1 to 10 carbon atoms. Examples of $C_1$-$C_{10}$ alkylene radicals include methylene, ethylene, propylene, butylene, pentylene and hexylene radicals.

As used herein, the term $C_2$-$C_{10}$ alkenylene embraces divalent alkenyl moieties typically having from 2 to 10 carbon atoms. Examples of $C_2$-$C_{10}$ alkenylene radicals include vinylene, propenylene, butenylene, pentenylene, hexenylene, heptenylene, octenylenyl radicals.

As used herein, the term $C_2$-$C_{10}$ alkynylene embraces divalent alkynyl moieties having 2 to 10 carbon atoms. Examples include propynylene, butynylene, heptynylene, octynylene.

As used herein, the term $C_1$-$C_4$ alkoxy (or alkyloxy) embraces optionally substituted, linear or branched oxy-containing radicals each having alkyl portions of 1 to 4 carbon atoms. Examples include methoxy, ethoxy, n-propoxy, i-propoxy, n-butoxy, sec-butoxy and t-butoxy.

As used herein, the term $C_1$-$C_4$ alkylthio embraces radicals containing a linear or branched alkyl radicals of 1 to 4 carbon atoms attached to a divalent —S— radical.

Examples include methylthio, ethylthio, n-propylthio, i-propylthio, n-butylthio, sec-butylthio and t-butylthio.

As used herein, the term $C_3$-$C_{10}$ cycloalkyl radical embraces saturated monocyclic carbocyclic radicals having from 3 to 10 carbon atoms. Examples of monocyclic cycloalkyl groups include cyclobutyl, cyclopentyl and cyclohexyl group.

As used herein, the term $C_5$-$C_{14}$ aryl radical embraces typically a $C_5$-$C_{14}$, preferably a $C_6$-$C_{14}$, more preferably a $C_6$-$C_{10}$ monocyclic or polycyclic aryl radical. Examples of aryl radicals include phenyl, naphthyl, naphthalenyl, anthranyl and phenanthryl.

As used herein, the term 5- to 14-membered heteroaryl radical embraces typically a 5- to 14-membered ring system comprising at least one heteroaromatic ring and containing at least one heteroatom selected from O, S and N. A 5- to 14-membered heteroaryl radical may be a single ring or two or more fused rings wherein at least one ring contains a heteroatom.

Examples include pyridyl, pyrazinyl, pyrimidinyl, pyridazinyl, furyl, benzofuranyl, oxadiazolyl, oxazolyl, isoxazolyl, benzoxazolyl, imidazolyl, benzimidazolyl, thiazolyl, thiadiazolyl, thienyl, pyrrolyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d] pyrimidinyl, thieno[2,3-d] pyrimidinyl and the various pyrrolopyridyl radicals.

As used herein, the term 3- to 14-membered heterocyclyl radical embraces typically a non-aromatic, saturated or unsaturated $C_3$-$C_{14}$ carbocyclic ring system in which one or more, for example 1, 2, 3 or 4 of the carbon atoms preferably 1 or 2 of the carbon atoms are replaced by a heteroatom selected from N, O and S. A heterocyclic radical may be a single ring or two or more fused rings wherein at least one ring contains a heteroatom, and may have one or more double bonds Examples of 3 to 14-membered heterocyclic radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, imidazolidinyl, imidazolyl, oxiranyl, thiaranyl, aziridinyl, oxetanyl, thiatanyl, azetidinyl, 4,5-dihydro-oxazolyl, 2-benzofuran-1 (3H)-one, 1,3-dioxol-2-one, tetrahydrofuranyl, 3-aza-tetrahydrofuranyl, tetrahydrothiophenyl, tetrahydropyranyl, tetrahydrothiopyranyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiezepanyl, 1,4-diazepanyl, tropanyl, (1 S,5R)-3-aza-bicyclo[3.1.0]hexyl, 3,4-dihydro-2H-pyranyl, 5,6-dihydro-2H-pyranyl, 2H-pyranyl, 2,3-hydrobenzofuranyl, 1,2,3,4-tetrahydropyridinyl, 1,2,5,6-tetrahydropyridinyl, isoindolinyl and indolinyl.

As used herein, the term halogen atom embraces chlorine, fluorine, bromine or iodine atoms. A halogen atom is typically a fluorine, chlorine or bromine atom. The term halo when used as a prefix has the same meaning.

Also included within the scope of the invention are the isomers, polymorphs, pharmaceutically acceptable salts, N-oxides, isotopes, solvates and prodrugs of the compounds of formula (I). Any reference to a compound of formula (I) throughout the present specification includes a reference to any isomer, polymorph, pharmaceutically acceptable salt, N-oxide, isotope, solvate or prodrug of such compound of formula (I).

Isomers

Compounds containing one or more chiral centre may be used in enantiomerically or diastereoisomerically pure form, in the form of racemic mixtures and in the form of mixtures enriched in one or more stereoisomer. The compounds of the present invention as described and claimed encompass the racemic forms of the compounds as well as the individual enantiomers, diastereomers, and stereoisomer-enriched mixtures.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomehc mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g. "Stereochemistry of Organic Compounds" by Ernest L. Eliel (Wiley, New York, 1994).

The compounds of Formula (I) may exhibit the phenomena of tautomerism and structural isomerism. Tautomers exist as mixtures of a tautomeric set in solution. In solid form, usually one tautomer predominates. Even though one tautomer may be described, the present invention includes all tautomers of the compounds of Formula (I).

Polymorphs

The compounds of the present invention may exist in different physical forms, i.e. amorphous and crystalline forms.

Moreover, the compounds of the invention may have the ability to crystallize in more than one form, a characteristic which is known as polymorphism. Polymorphs can be distinguished by various physical properties well known in the art such as X-ray diffraction pattern, melting point or solubility. All physical forms of the compounds of the present invention, including all polymorphic forms ("polymorphs") thereof, are included within the scope of the invention.

Salts

As used herein, the term pharmaceutically acceptable salt refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid; and organic acids, for example citric, fumaric, gluconic, glutamic, lactic, maleic, malic, mandelic, mucic, ascorbic, oxalic, pantothenic, succinic, tartaric, benzoic, acetic, methanesulphonic, ethanesulphonic, benzenesulphonic, p-toluenesulphonic acid, xinafoic (1-hydroxy-2-naphthoic acid), napadisilic (1,5-naphthalenedisulfonic acid) and the like. Particularly preferred are salts derived from fumaric, hydrobromic, hydrochloric, acetic, sulfuric, methanesulfonic, xinafoic, and tartaric acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts.

Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to the invention are quaternary ammonium compounds wherein an equivalent of an anion ($X^-$) is associated with the positive charge of the N atom. $X^-$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. $X^-$ is preferably an anion selected from chloride, bromide, iodide, sulphate, nitrate, acetate, maleate, oxalate, succinate or trifluoroacetate. More preferably $X^-$ is chloride, bromide, trifluoroacetate or methanesulphonate.

N-oxides

As used herein, an N-oxide is formed from the tertiary basic amines or imines present in the molecule, using a convenient oxidising agent.

Isotopes

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Preferred isotopically-labeled compounds include deuterated derivatives of the compounds of the invention. As used herein, the term deuterated derivative embraces compounds of the invention where in a particular position at least one hydrogen atom is replaced by deuterium. Deuterium (D or $^2H$) is present at a natural abundance of 0.015 molar %.

Solvates

The compounds of the invention may exist in both unsolvated and solvated forms. The term solvate is used herein to describe a molecular complex comprising a compound of the invention and an amount of one or more pharmaceutically acceptable solvent molecules. The term hydrate is employed when said solvent is water. Examples of solvate forms include, but are not limited to, compounds of the invention in association with water, acetone, dichloromethane, 2-propanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate.

Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-solvate form of the compounds.

Prodrugs

Prodrugs of the compounds described herein are also within the scope of the invention. Thus certain derivatives of the compounds of the present invention, which derivatives may have little or no pharmacological activity themselves, when administered into or onto the body may be converted into compounds of the present invention having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of the present invention with certain moieties known to those skilled in the art as 'promoieties' as described, for example, in Design of Prodrugs by H. Bundgaard (Elsevier, 1985).

Typically G is selected from the group consisting of a $C_5$-$C_6$ aryl group, a 8- to 10-membered saturated or unsaturated bicyclic heterocyclyl group having one or more heteroatoms selected from N, S and O, a 8- to 10-membered bicyclic heteroaryl group having one or more heteroatoms selected from N, S and O and a $C_5$-$C_6$ aryl group linked to a ring system selected from a $C_{5-6}$ aryl group, a $C_{3-7}$ cycloalkyl group and a 5- to 6-membered heteroaryl group having two or three heteroatoms selected from N, S and O, wherein the cyclic groups independently are optionally substituted with one or more substituents selected from a halogen atom, a $C_{1-4}$ alkyl group, a $C_{1-4}$ alkoxy group, a cyano group, a nitro group, a hydroxy group and an oxo group.

Preferably, G is selected from a phenyl group, a 9- to 10-membered unsaturated bicyclic heterocyclyl group having one or more heteroatoms selected from N, S and O, a 9- to 10-membered bicyclic heteroaryl group having one or more heteroatoms selected from N, S and O and a $C_5$-$C_6$ aryl group linked to a ring system selected from a $C_{5-6}$ aryl group and a 5- to 6-membered heteroaryl group having two or three heteroatoms selected from N, S and O, wherein the cyclic groups independently are optionally substituted with one or two substituents selected from a halogen atom, a methyl group, a methoxy group, a cyano group, a hydroxy group and an oxo group.

Typically, $L_1$ is selected from the group consisting of direct bond, —$NR^c$—, —S—, —$SO_2$—, —C(O)—, —C(O)O—, —S(O)$_2$$NR^c$—, —$NR^c$S(O)$_2$—, —$NR^c$(CO)(CH$_2$)O—, —O(CH$_2$)(CO)$NR^c$—, —$NR^c$(CO)$NR^d$— and —CONR$^c$S(O)$_2$—, wherein $R^c$ and $R^d$ independently are selected from a hydrogen atom and a methyl group.

Preferably $L_1$ is selected from a direct bond, —NH—, —S—, —SO$_2$—, —C(O)—, —$NR^c$(CO)$NR^c$— and —O(CH$_2$)(CO)$NR^c$—, more preferably $L_1$ is selected from a direct bond, —NH—, —SO$_2$—, —NH(CO)NH— and —O(CH$_2$)(CO)$NR^c$—, being most preferably a direct bond or —O(CH$_2$)(CO)$NR^c$—.

In a preferred embodiment of the present invention, -G-$L_1$- has the following formula:

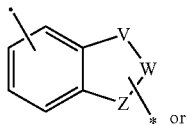

Formula (Iwa)

or

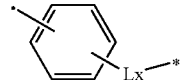

Formula (Iwb)

wherein

V, W and Z are independently selected from a —N—, —C—, —S—, —O— and —C(O)—

Lx represents a 5 to 6 membered heteroaryl group having at least one heteroatom selected from N, S and O, or Lx represents a —O—CH$_2$—CO—NR$^d$—, wherein R$^d$ represents a hydrogen atom or a methyl group.

\* represents the point of attachment with A$_2$ and

● represents the point of attachment with A$_1$.

In a preferred embodiment of the present invention, -G-$L_1$- has the following formula (Iwa):

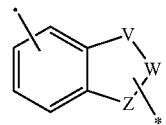

Formula (Iwa)

wherein V, W and Z are as defined above.

In a still preferred embodiment,

Z is a nitrogen atom,

V represents a nitrogen atom, an oxygen atom, a carbon atom or a sulphur atom and, W represents a nitrogen atom, a carbon atom or a carbonyl atom.

More preferably, G-$L_1$- has the following formula (Iwaa):

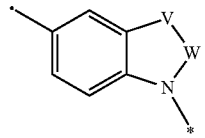

Formula (Iwaa)

wherein V and W are as defined above.

Typically R³ represents a group of formula:

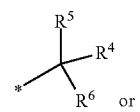

i)

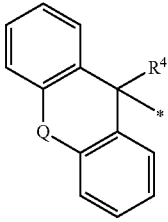

ii)

wherein:
R⁴ represents a hydrogen atom, a hydroxy group, a hydroxymethyl group or a linear or branched $C_{1-4}$ alkyl group,
R⁵ and R⁶ independently represent $C_{5-6}$ aryl group, a 5- to 6-membered heteroaryl group containing at least one heteroatom selected from N, S, and O; ($C_{1-4}$ alkyl)-($C_{5-6}$ aryl) group, a $C_{3-8}$ cycloalkyl group,
Q represents a direct bond or a —CH₂—, —CH₂—CH₂—, —O—, —O—CH₂—, —S—, —S—CH₂—, or —CH═CH—,
* represents the point of attachment of R₃ to the remainder of the molecule of formula (I), More preferably R³ represents a group of formula i) or ii), wherein:
R⁴ represents a hydrogen atom, a hydroxy group, a hydroxymethyl group or a linear or branched $C_{1-4}$ alkyl group,
R⁵ and R⁶ independently represents a thienyl group, a phenyl group, a benzyl group or a $C_{4-6}$ cycloalkyl group,
Q represents a direct bond or an oxygen atom,
* represents the point of attachment of R₃ to the remainder of the molecule of formula (I), In another embodiment, compounds of the present invention have the following formula (IA):

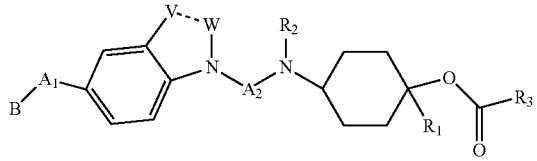

Formula (IA)

wherein R₁, R₂, R₃, A₁, A₂, V, W and B are as defined above.
Typically, A₁ and A₂ independently are selected from the group consisting of a $C_{1-6}$ alkylene group, $C_{2-6}$ alkenylene group and $C_{2-6}$ alkynylene group, wherein said groups are optionally substituted with one or more substituents selected from halogen atom, a hydroxy group, a $C_{1-2}$ alkyl group, a $C_{1-2}$ alkoxy group, a $C_{5-6}$ aryl group and a $C_{3-6}$ cycloalkyl group.
Preferably, A₁ and A₂ independently represent a $C_{1-6}$ alkylene group optionally substituted with one or more substituents selected from a $C_{1-2}$ alkyl group, a $C_{1-2}$ alkoxy group and a phenyl group, preferably substituted with one or two substituents selected from a methyl group and a methoxy group, more preferably a methyl group.
Typically B is a moiety having a beta2-adrenergic binding activity such that the $IC_{50}$ of the compound is 1 mM or less, preferably 100 μM or less, more preferably 10 μM or less, more preferably 1 μM or less, more preferably 500 nM or less, most preferably 250 nM or less, as measured in a beta2-adrenergic binding assay.
Typically said beta2-adrenergic binding assay comprises:
a) providing a membrane suspension comprising Sf9 cells in an assay buffer
b) incubating with 3H-CGP12177 in plates previously treated with assay buffer containing a coating agent
c) measuring binding of test compound in the presence of propanolol
d) maintaining incubation
e) terminating the binding reactions
f) determining the affinity of the test compound for the receptor by repeating steps a) to e) using multiple different test compound concentrations.
g) calculating an $IC_{50}$ using the four parameters-log equation.
Typically B represents a group of formula (IB):

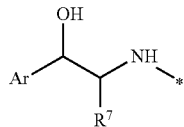

Formula (IB)

wherein:
R⁷ is selected from the group consisting of a hydrogen atom, a linear or branched $C_{1-4}$ alkyl group and a linear or branched $C_{1-4}$ alkoxy group,
Ar is selected from the group consisting of a $C_{3-10}$ saturated or unsaturated, mono- or bicyclic cycloalkyl group, a $C_5$-$C_{14}$ mono- or bicyclic aryl group, a 3 to 14-membered saturated or unsaturated mono- or bicyclic heterocyclyl group having one or more heteroatoms selected from N, S and O, a 5- to 14-membered mono- or bicyclic heteroaryl group having one or more heteroatoms selected from N, S and O and wherein the cyclic groups independently are optionally substituted with one or more substituents selected from a halogen atom, a cyano group, a nitro group, an oxo group, a carboxy group, a $C_{1-4}$ alkyl group, a $C_{1-4}$ alkoxy group, —CF₃, —OCF₃, —NR$^e$R$^f$, —(CH₂)$_p$—OH, —NR$^e$(CO)R$^f$, —NR$^e$—SO₂—R$^g$, —SO₂NR$^e$R$^f$, —OC(O)R$^h$, and —NR$^e$(CH₂)$_{(0-2)}$—R$^i$, wherein p has a value of 0, 1 or 2 and wherein:
R$^e$ and R$^f$ independently represent a hydrogen atom or a linear or branched $C_{1-4}$ alkyl group,
R$^g$ is selected from the group consisting of a linear or branched $C_{1-4}$ alkyl group, a $C_{6-5}$ aryl group, a saturated or unsaturated $C_{3-8}$ cycloalkyl, wherein the cyclic groups independently are optionally substituted with one or more substituents selected from a halogen atom, a $C_{1-4}$ alkyl group and a $C_{1-4}$ alkoxy group,
R$^h$ is selected from a hydrogen atom, —NR$^e$R$^f$ and a $C_{5-6}$ aryl group which is optionally substituted with one or more substituents selected from a $C_{1-4}$ alkyl group and a $C_{1-4}$ alkoxy group,
R$^i$ is selected from the group consisting of a $C_{5-6}$ aryl group, $C_{3-8}$ cycloalkyl group and a 3- to 8-membered saturated or unsaturated heterocyclyl group, which groups independently are optionally substituted with one or more substituents selected from a halogen atom, a $C_{1-4}$ alkyl group and a $C_{1-4}$ alkoxy group.

Preferably, Ar represents a group of formula:

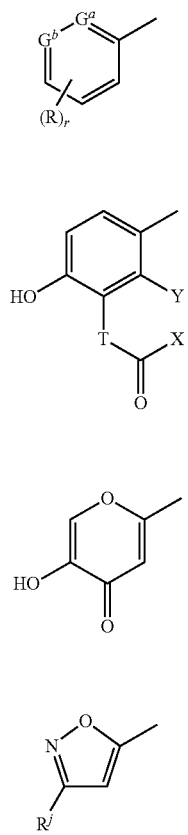

wherein

G$^a$ and G$^b$ independently are selected from a nitrogen atom and a carbon atom, r has a value of 0, 1, 2 or 3 and R is selected from the group consisting of a halogen atom, an amino group, a cyano group, a nitro group, an oxo group, a carboxy group, a $C_{1-4}$ alkyl group, a $C_{1-4}$ alkoxy group, —CF$_3$, —OCF$_3$, —(CH$_2$)$_p$—OH, —NH(CO)H, —NH—SO$_2$—R$^9$, —SO$_2$NH$_2$, —OC(O)H, —O(CO)-(4-methyl)phenyl, —O(CO)—N(CH$_3$)$_2$, —OC(O)NH$_2$ and —NH(CH$_2$)$_{(1-2)}$—R$^i$, group, wherein p is as defined above and R$^g$ and R$^i$ independently are selected from a phenyl group optionally substituted with a substituent selected from a methyl group or a methoxy group.

R$^j$ represents a halogen atom,

T is selected from the group consisting of —CH$_2$— and —NH—,

Both X and Y represent a hydrogen atom or X together with Y form the group —CH$_2$—CH$_2$—, —CH═CH—, —CH$_2$—O— or —S—, wherein in the case of —CH$_2$—O— the methylene group is bound to the carbonyl group holding X and the oxygen atom is bound to the carbon atom in the phenyl ring holding Y.

Preferably, Ar represents a compound of formula (a) or (b) wherein:

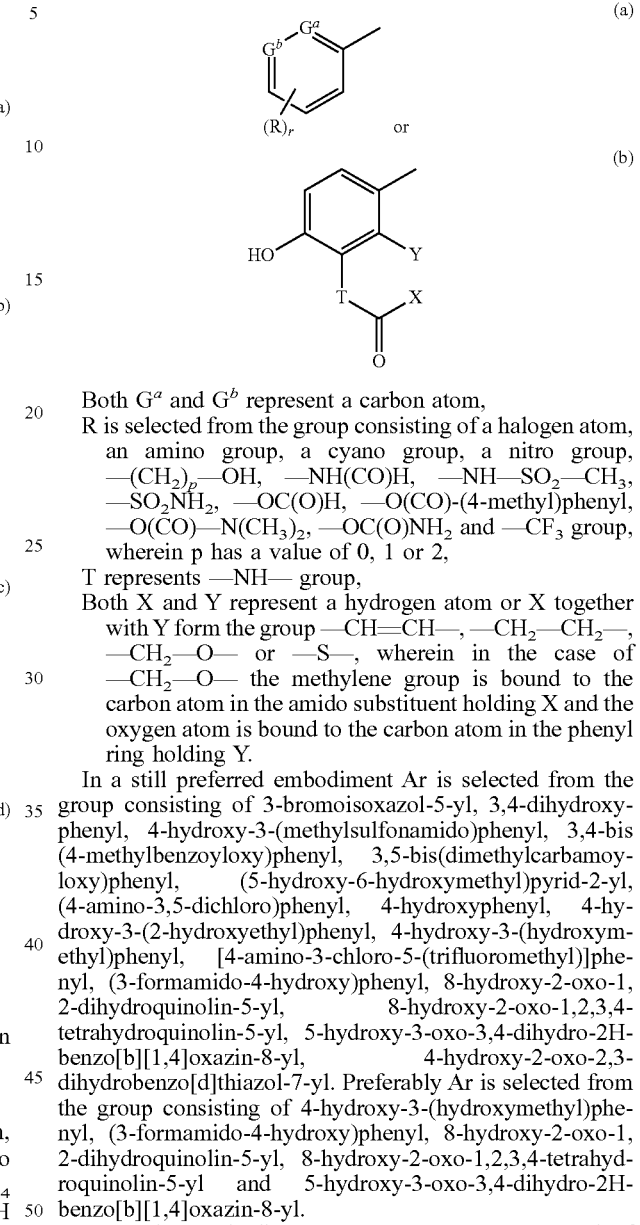

Both G$^a$ and G$^b$ represent a carbon atom,

R is selected from the group consisting of a halogen atom, an amino group, a cyano group, a nitro group, —(CH$_2$)$_p$—OH, —NH(CO)H, —NH—SO$_2$—CH$_3$, —SO$_2$NH$_2$, —OC(O)H, —O(CO)-(4-methyl)phenyl, —O(CO)—N(CH$_3$)$_2$, —OC(O)NH$_2$ and —CF$_3$ group, wherein p has a value of 0, 1 or 2, T represents —NH— group, Both X and Y represent a hydrogen atom or X together with Y form the group —CH═CH—, —CH$_2$—CH$_2$—, —CH$_2$—O— or —S—, wherein in the case of —CH$_2$—O— the methylene group is bound to the carbon atom in the amido substituent holding X and the oxygen atom is bound to the carbon atom in the phenyl ring holding Y.

In a still preferred embodiment Ar is selected from the group consisting of 3-bromoisoxazol-5-yl, 3,4-dihydroxyphenyl, 4-hydroxy-3-(methylsulfonamido)phenyl, 3,4-bis(4-methylbenzoyloxy)phenyl, 3,5-bis(dimethylcarbamoyloxy)phenyl, (5-hydroxy-6-hydroxymethyl)pyrid-2-yl, (4-amino-3,5-dichloro)phenyl, 4-hydroxyphenyl, 4-hydroxy-3-(2-hydroxyethyl)phenyl, 4-hydroxy-3-(hydroxymethyl)phenyl, [4-amino-3-chloro-5-(trifluoromethyl)]phenyl, (3-formamido-4-hydroxy)phenyl, 8-hydroxy-2-oxo-1,2-dihydroquinolin-5-yl, 8-hydroxy-2-oxo-1,2,3,4-tetrahydroquinolin-5-yl, 5-hydroxy-3-oxo-3,4-dihydro-2H-benzo[b][1,4]oxazin-8-yl, 4-hydroxy-2-oxo-2,3-dihydrobenzo[d]thiazol-7-yl. Preferably Ar is selected from the group consisting of 4-hydroxy-3-(hydroxymethyl)phenyl, (3-formamido-4-hydroxy)phenyl, 8-hydroxy-2-oxo-1,2-dihydroquinolin-5-yl, 8-hydroxy-2-oxo-1,2,3,4-tetrahydroquinolin-5-yl and 5-hydroxy-3-oxo-3,4-dihydro-2H-benzo[b][1,4]oxazin-8-yl.

In another embodiment Ar represents a compound of formula (b) wherein X and Y are as defined above and T represents a —NH— group.

Still in another embodiment of the present invention, compounds of the present invention have the following formula (IC):

Formula (IC)

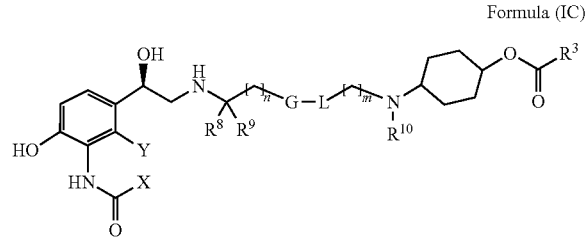

Wherein:
R³ represents a group of formula:

i)

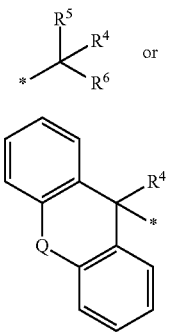

or ii)

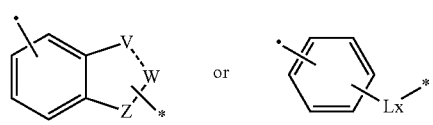

wherein:
- R⁴ represents a hydrogen atom, a hydroxy group, a hydroxymethyl group or a linear or branched $C_{1-4}$ alkyl group,
- R⁵ and R⁶ independently represent $C_{5-6}$ aryl group, a 5- to 6-membered heteroaryl group containing at least one heteroatom selected from N, S, and O; ($C_{1-4}$ alkyl)-($C_{5-6}$ aryl) group, a $C_{3-8}$ cycloalkyl group,
- Q represents a direct bond or a —CH₂—, —CH₂—CH₂—, —O—, —O—CH₂—, —S—, —S—CH₂—, or —CH=CH—,
- * represents the point of attachment of R₃ to the remainder of the molecule of formula (I),
- Both X and Y represent a hydrogen atom or X together with Y form the group —CH=CH—, —CH₂—CH₂—, —CH₂—O— or —S—, wherein in the case of —CH₂—O— the methylene group is bound to the carbon atom in the amido substituent holding X and the oxygen atom is bound to the carbon atom in the phenyl ring holding Y,
- n has a value of 0, 1 or 2,
- m has a value of 2, 3 or 4,
- R⁸, R⁹ and R¹⁰ independently represent a hydrogen atom or a linear or branched $C_{1-4}$ alkyl group,
- -G-L₁- represents a group of formula (IG):

Formula (Iw)

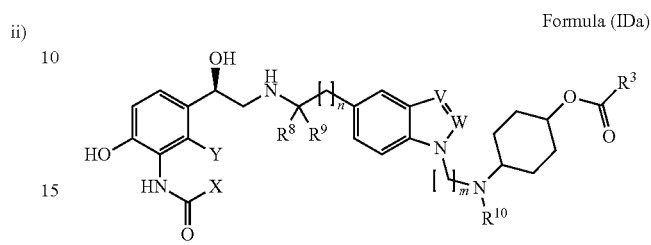

wherein
- V, W and Z are independently selected from a —N—, —C—, —S—, —O— and —C(O)—
- Lx represents a 5 to 6 membered heteroaryl group having at least one heteroatom selected from N, S and O, or Lx represents a —O—CH₂—CO—NR$^d$—, wherein R$^d$ represents a hydrogen atom or a methyl group.
- * represents the point of attachment with the moiety containing the cyclohexyl group and
- ● represents the point of attachment with the moiety containing the aminoethylphenol moiety, In a still preferred embodiment, Lx represents a 5 to 6 membered heteroaryl group having at least one heteroatom selected from N, S and O, preferably Lx is selected from a pyridyl, a pyrazinyl, a furyl, an oxadiazolyl, a imidazolyl, a thiazolyl and a thienyl group, more preferably, Lx represents a pyridyl, an oxadiazolyl, a imidazolyl or a thiazolyl group, being most preferably an oxadiazolyl group.

In a preferred embodiment, compounds of the present invention have the following formula (IDa):

Formula (IDa)

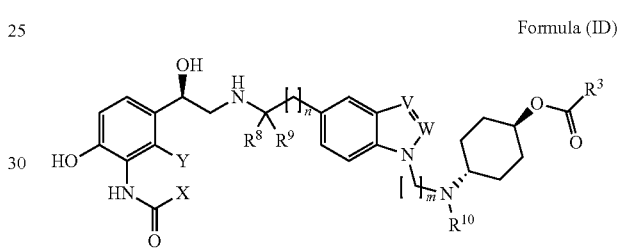

wherein V, W, X, Y, R⁸, R⁹, R¹⁰, n and m are as defined above.

In a still preferred embodiment, compounds of the present invention have the following formula (ID):

Formula (ID)

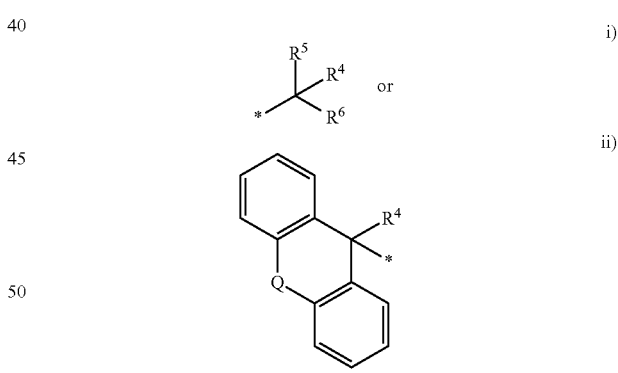

Wherein:
V, W, X, Y, R⁸, R⁹, R¹⁰, n and m are as defined above,
R³ represents a group of formula:

i)

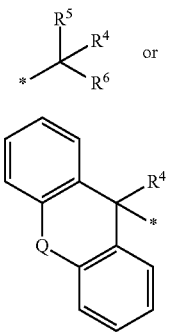

or ii)

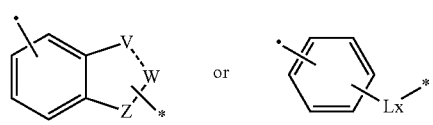

wherein:
- R⁴ represents a hydrogen atom, a hydroxy group, a hydroxymethyl group or a linear or branched $C_{1-4}$ alkyl group,
- R⁵ and R⁶ independently represents a thienyl group, a phenyl group, a benzyl group or a $C_{4-6}$ cycloalkyl group,
- Q represents a direct bond or an oxygen atom,
- * represents the point of attachment of R₃ to the remainder of the molecule of formula (I), Typically, X together with Y form the group —CH=CH— or —CH₂—O—. Preferably, X together with Y form the group —CH=CH—.

Typically W represents a nitrogen atom or a carbonyl group, preferably W represents a nitrogen atom.

Typically, V represents a nitrogen atom, an oxygen atom or a sulphur atom, preferably V is a nitrogen atom or an oxygen atom.

In a preferred embodiment V represents a nitrogen atom or an oxygen atom while W represents a carbonyl group.

In another preferred embodiment both V and W represent a nitrogen atom.

Typically, n has a value 0.

Typically, m has a value of 3.

Typically $R^{10}$ represents a hydrogen atom or a methyl group, preferably a methyl group.

Typically, $R^8$ and $R^9$ independently represent a hydrogen atom or a methyl group, preferably both $R^8$ and $R^9$ represent a hydrogen atom.

Typically, $R_3$ represents a group of formula ii), wherein Q is an oxygen atom and $R^4$ is selected from a hydrogen atom, a hydroxy group and a methyl group. Preferably $R^4$ represents a hydroxy group or a methyl group, more preferably a methyl group.

Typically, $R_3$ represents a group of formula i) wherein:
$R^4$ represents a hydrogen atom, a methyl group or a hydroxy group, preferably $R^4$ represents a hydroxy group,
$R^5$ and $R^6$ independently represent a thienyl group, a cyclopentyl group or a benzyl group, preferably both $R^5$ and $R^6$ are thienyl groups.

In one embodiment of the present invention, in compounds of formula (IC)

-G-$L_1$- represents a group of formula:

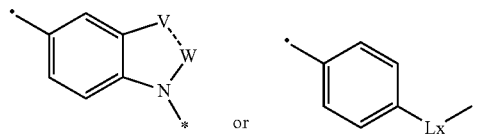

Wherein
V is selected from —N—, —C—, —S— and —O—,
W is selected from —N—, —C—, and —C(O)—,
Lx represents an oxadiazolyl group or —O—$CH_2$—CO—$NR^d$—, wherein $R^d$ represents a hydrogen atom or a methyl group.
* represents the point of attachment with the moiety containing the cyclohexyl group and
● represents the point of attachment with the moiety containing the aminoethylphenol fragment,
$R^8$ and $R^9$ independently are selected from a hydrogen atom and a methyl group,
$R^{10}$ represents a methyl group,
n has a value of 0 or 1,
m has a value of 2, 3 or 4,
Both X and Y represents a hydrogen atom or X together with Y form —CH=CH—, —$CH_2$—O—, or —S— group,
$R_3$ represents a group of formula:

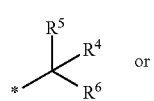

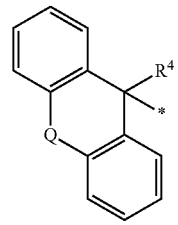

wherein:
$R^4$ represents a methyl group or a hydroxy group,
$R^5$ and $R^6$ independently represents a thienyl group, a phenyl group, benzyl group or a cyclopentyl group,
Q represents a direct bond or an oxygen atom,
* represents the point of attachment of $R^3$ to the remainder of the molecule of formula (I).

Preferably,
-G-$L_1$- represents a group of formula:

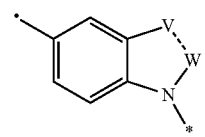

Wherein
W represents a nitrogen atom or a carbonyl group,
V represents a nitrogen or an oxygen atom,
Both $R^8$ and $R^9$ represents a hydrogen atom,
X together with Y form —CH=CH—,
$R_3$ represents a group of formula i) wherein $R^4$ represents a hydroxy group and both $R^5$ and $R^6$ represent a thienyl group.

Particular individual compounds of the invention include:
Trans-4-[{3-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}(methyl)amino]-cyclohexyl hydroxy(di-2-thienyl)acetate, dihydrofluoride,
trans-4-[{3-[5-({[(2R)-2-hydroxy-2-(8-hydroxy-2-oxo-1,2-dihydroquinolin-5-yl)ethyl]amino}methyl)-2-oxo-2,3-dihydro-1H-benzimidazol-1-yl]propyl}(methyl)amino]cyclohexyl hydroxy(di-2-thienyl)acetate dihydrofluoride,
Trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexylhydroxy(di-2-thienyl)acetate dihydrofluoride,
Trans-4-[{3-[5-({[(2R)-2-hydroxy-2-(8-hydroxy-2-oxo-1,2-dihydroquinolin-5-yl)ethyl]amino}methyl)-1H-indol-1-yl]propyl}(methyl)amino]cyclohexylhydroxy (di-2-thienyl)acetate dihydrofluoride,
Trans-4-[{3-[5-({[(2R)-2-hydroxy-2-(8-hydroxy-2-oxo-1,2-dihydroquinolin-5-yl)ethyl]amino}methyl)-1H-benzimidazol-1-yl]propyl}(methyl)amino]cyclohexyl hydroxy (di-2-thienyl)acetate,
Trans-4-[{3-[5-({[(2R)-2-hydroxy-2-(8-hydroxy-2-oxo-1,2-dihydroquinolin-5-yl) ethyl]amino}methyl)-1H-indazol-1-yl]propyl}(methyl)amino]cyclohexylhydroxy(di-2-thienyl)acetate,
Trans-4-[{3-[6-({[(2R)-2-hydroxy-2-(8-hydroxy-2-oxo-1,2-di hydroquinolin-5-yl)ethyl]amino}methyl)-2-oxo-1,3-benzothiazol-3(2H)-yl]propyl}(methyl)amino]cyclohexyl hydroxy(di-2-thienyl)acetate, Trans-4-[(3-{5-[({(2R)-2-[3-(formylamino)-4-hydroxyphenyl]-2-hydroxyethyl}amino)methyl]-1H-1,2,3-benzotriazol-1-yl}propyl)(methyl)amino]cyclohexyl hydroxy(di-2-thienyl)acetate, Trans-4-[{3-[5-({[(2R)-2-hydroxy-2-(4-hydroxy-2-oxo-2,3-dihydro-1,3-benzothiazol-7-yl)ethyl]amino}methyl)-1H-1,2,3-benzotriazol-1-yl]propyl}(methyl) amino]cyclohexyl hydroxy(di-2-thienyl)acetate, Trans-4-[{3-[6-(2-{[(2R)-2-hydroxy-2-(8-hydroxy-2-methylene-1,2-dihydroquinolin-5-yl)ethyl]amino}ethyl)-2-oxo-1,3-benzoxazol-3(2H)-yl]propyl}(methyl)amino]cyclohexyl hydroxy(di-2-thienyl)acetate, Trans-4-[{2-[6-({[(2R)-2-hydroxy-2-(8-hydroxy-2-oxo-1,2-di hydroquinolin-5-yl)ethyl]amino}methyl)-2-oxo-1,3-benzoxazol-3(2H)-yl]ethyl}(methyl)amino]cyclohexyl hydroxy(di-2-thienyl)acetate, Trans-4-[{4-[6-({[(2R)-2-hydroxy-2-(8-hydroxy-2-oxo-1,2-di hydroquinolin-5-yl)ethyl]amino}methyl)-2-oxo-1,3-benzoxazol-3(2H)-yl]butyl}(methyl)amino]cyclohexyl hydroxy(di-2-thienyl)acetate, Trans-4-[{3-[5-({[(2R)-2-hydroxy-2-(8-hydroxy-2-oxo-1,2-di hydroquinolin-5-yl)ethyl]amino}methyl)-1H-1,2,3-benzotriazol-1-yl]propyl}(methyl)amino]cyclohexylcyclopentyl(hydroxy)2-thienylacetate, Trans-4-[{3-[6-({[(2R)-2-hydroxy-2-(8-hydroxy-2-oxo-1,2-di hydroquinolin-5-yl)ethyl]amino}methyl)-2-oxo-1,3-benzoxazol-3(2H)-yl]propyl}(methyl)amino]cyclohexyl-9-methyl-9H-xanthene-9-carboxylate, Trans-4-[{3-[6-({[(2R)-2-hydroxy-2-(5-hydroxy-3-oxo-3,4-dihydro-2H-1,4-benzoxazin-8-yl)ethyl]amino}methyl)-2-oxo-1,3-benzothiazol-3(2H)-yl]propyl}(methyl)amino]cyclohexyl hydroxy(di-2-thienyl)acetate, Trans-4-[(2-{5-[({(2R)-2-[3-(formylamino)-4-hydroxyphenyl]-2-hydroxyethyl}amino)methyl]-1H-indol-1-yl}ethyl)(methyl)amino]cyclohexyl 9H-fluorene-9-carboxylate, Trans-4-[(3-{5-[({(2R)-2-[3-(formylamino)-4-hydroxyphenyl]-2-hydroxyethyl}amino)methyl]-1H-indol-1-yl}propyl)(methyl)amino]cyclohexyl 2-hydroxy-3-phenyl-2-(2-thienyl)propanoate, Trans-4-[{3-[5-(2-{[(2R)-2-hydroxy-2-(8-hydroxy-2-oxo-1,2-dihydroquinolin-5-yl)ethyl]amino}-2-methylpropyl)-2-oxo-2,3-dihydro-1H-benzimidazol-1-yl]propyl}(methyl) amino]cyclohexyl 2,2-diphenylpropanoate, Trans-4-[{2-[5-(2-{[(2R)-2-hydroxy-2-(8-hydroxy-2-oxo-1,2-dihydroquinolin-5-yl) ethyl]amino}-2-methylpropyl)-1H-indazol-1-yl]ethyl}(methyl)amino]cyclohexyl 2-phenyl-2-(2-thienyl)propanoate, Trans-4-[{3-[6-(2-{[(2R)-2-hydroxy-2-(8-hydroxy-2-methylene-1,2-dihydroquinolin-5-yl)ethyl]amino}propyl)-2-oxo-1,3-benzoxazol-3(2H)-yl]propyl}(methyl)amino]cyclohexyl hydroxy(di-2-thienyl)acetate, Trans-4-[(3-{3-[4-({[(2R)-2-hydroxy-2-(8-hydroxy-2-oxo-1,2-dihydroquinolin-5-yl)ethyl]amino}methyl)phenyl]-1,2,4-oxadiazol-5-yl}propyl)(methyl)amino]cyclohexyl hydroxy(di-2-thienyl)acetate, Trans-4-[{2-[{[4-({[(2R)-2-hydroxy-2-(8-hydroxy-2-oxo-1,2-dihydroquinolin-5-yl)ethyl]amino}methyl)phenoxy]acetyl}(methyl)amino]ethyl}(methyl)amino]cyclohexyl hydroxy(di-2-thienyl)acetate, Trans-4-[[2-({[4-({[(2R)-2-hydroxy-2-(8-hydroxy-2-oxo-1,2-dihydroquinolin-5-yl)ethyl]amino}methyl)phenoxy]acetyl}amino)ethyl](methyl)amino]cyclohexyl hydroxy(di-2-thienyl)acetate, Trans-4-[(3-{3-[2-chloro-4-({[(2R)-2-hydroxy-2-(8-hydroxy-2-oxo-1,2-dihydroquinolin-5-yl)ethyl]amino}methyl)-5-methoxyphenyl]-1,2,4-oxadiazol-5-yl}propyl)(methyl)amino]cyclohexyl hydroxy(di-2-thienyl)acetate and Trans-4-[{2-[{[2-chloro-4-({[(2R)-2-hydroxy-2-(8-hydroxy-2-oxo-1,2-dihydroquinolin-5-yl)ethyl]amino}methyl)-5-methoxyphenoxy]acetyl}(methyl)amino]ethyl}(methyl) amino]cyclohexyl hydroxy(di-2-thienyl)acetate, trans-4-[{3-[1-(2-{[(2R)-2-hydroxy-2-(8-hydroxy-2-oxo-1,2-dihydroquinolin-5-yl)ethyl]amino}ethyl)-1H-indol-3-yl]propyl}(methyl)amino]cyclohexyl hydroxy(di-2-thienyl)acetate dihydrofluoride, trans-4-[(3-{5-[({(2R)-2-[3-(acetylamino)-4-hydroxyphenyl]-2-hydroxyethyl}amino) methyl]-2-oxo-2,3-dihydro-1H-benzimidazol-1-yl}propyl)(methyl)amino]cyclohexyl hydroxy(di-2-thienyl)acetate dihydrofluoride, trans-4-[{3-[6-[({(2R)-2-[3-(formylamino)-4-hydroxyphenyl]-2-hydroxyethyl}amino) methyl]-2-oxo-1,3-benzoxazo-3(2H)-yl]propyl}(methyl)amino]cyclohexyl 9-methyl-9H-xanthene-9-carboxylate dihydrofluoride trans-4-[{3-[5-({[(2R)-2-hydroxy-2-(5-hydroxy-3-oxo-3,4-dihydro-2H-1,4-benzoxazin-8-yl)ethyl]amino}methyl)-1H-1,2,3-benzotriazol-1-yl]propyl}(methyl)amino]cyclohexyl (2S)-cyclopentyl(hydroxy)2-thienylacetate dihydrofluoride, trans-4-{[2-({2-[4-(2-{[(2R)-2-hydroxy-2-(8-hydroxy-2-oxo-1,2-dihydroquinolin-5-yl)ethyl]amino}propyl)phenoxy]acetyl}amino)ethyl]amino}cyclohexyl hydroxy(di-2-thienyl)acetate dihydrofluoride, and trans-4-[{3-[5-({[(2R)-2-hydroxy-2-(4-hydroxy-2-oxo-2,3-dihydro-1,3-benzothiazol-7-yl)ethyl]amino}methyl)-1H-1,2,3-benzotriazol-1-yl]propyl}(methyl)amino]cyclohexyl (2S)-cyclopentyl(hydroxy)2-thienylacetate or pharmaceutically acceptable salts or N-oxides or solvates or deuterated derivative thereof:

Of particular interest are the compounds:

Trans-4-[{3-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}(methyl)amino]-cyclohexyl hydroxy(di-2-thienyl)acetate, dihydrofluoride, trans-4-[{3-[5-({[(2R)-2-hydroxy-2-(8-hydroxy-2-oxo-1,2-dihydroquinolin-5-yl)ethyl]amino}methyl)-2-oxo-2,3-dihydro-1H-benzimidazol-1-yl]propyl}(methyl)amino]cyclohexyl hydroxy(di-2-thienyl)acetate dihydrofluoride, Trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexylhydroxy(di-2-thienyl)acetate dihydrofluoride, Trans-4-[{3-[5-({[(2R)-2-hydroxy-2-(8-hydroxy-2-oxo-1,2-dihydroquinolin-5-yl)ethyl]amino}methyl)-1H-indol-1-yl]propyl}(methyl)amino]cyclohexylhydroxy (di-2-thienyl)acetate dihydrofluoride, Trans-4-[{3-[6-({[(2R)-2-hydroxy-2-(8-hydroxy-2-oxo-1,2-dihydroquinolin-5-yl)ethyl]amino}methyl)-2-oxo-1,3-benzothiazol-3(2H)-yl]propyl}(methyl)amino]cyclohexyl hydroxy(di-2-thienyl)acetate, Trans-4-[(3-{5-[({(2R)-2-[3-(formylamino)-4-hydroxyphenyl]-2-hydroxyethyl}amino)methyl]-1H-1,2,3-benzotriazol-1-yl}propyl)(methyl)amino]cyclohexyl hydroxy(di-2-thienyl)acetate, Trans-4-[{3-[5-({[(2R)-2-hydroxy-2-(4-hydroxy-2-oxo-2,3-dihydro-1,3-benzothiazol-7-yl)ethyl]amino}methyl)-1H-1,2,3-benzotriazol-1-yl]propyl}(methyl) amino]cyclohexyl hydroxy(di-2-thienyl)acetate, Trans-4-[{2-[6-({[(2R)-2-hydroxy-2-(8-hydroxy-2-oxo-1,2-dihydroquinolin-5-yl)ethyl]amino}methyl)-2-oxo-1,3- benzoxazol-3(2H)-yl]ethyl}(methyl)amino]cyclohexyl-hydroxy(di-2-thienyl)acetate, Trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexylcyclopentyl(hydroxy)2-thienylacetate, Trans-4-[{3-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}(methyl)amino]cyclohexyl-9-methyl-9H-xanthene-9-carboxylate, Trans-4-[{2-[{4-({[(2R)-2-hydroxy-2-(8-hydroxy-2-oxo-1,2-dihydroquinolin-5-yl)ethyl]amino}methyl)phenoxy]acetyl}(methyl)amino]ethyl}(methyl)amino]cyclohexyl hydroxy(di-2-thienyl)acetate, Trans-4-[[2-({[4-({[(2R)-2-hydroxy-2-(8-hydroxy-2-oxo-1,2-dihydroquinolin-5-yl)ethyl]amino}methyl)phenoxy]acetyl}amino)ethyl](methyl)amino]cyclohexyl hydroxy(di-2-thienyl)acetate, Trans-4-[(3-{3-[2-chloro-4-({[(2R)-2-hydroxy-2-(8-hydroxy-2-oxo-1,2-dihydro-quinolin-5-yl)ethyl]amino}methyl)-5-methoxyphenyl]-1, 2,4-oxadiazol-5-yl}propyl)(methyl)amino]cyclohexyl hydroxy(di-2-thienyl)acetate, and Trans-4-[{3-[5-({[(2R)-2-hydroxy-2-(5-hydroxy-3-oxo-3,4-dihydro-2H-1,4-benzoxazin-8-yl)ethyl]amino}methyl)-1H-1,2,3-benzotriazol-1-yl]propyl}(methyl)amino]-cyclohexyl (2S)-cyclopentyl(hydroxy)2-thienylacetate dihydrofluoride or pharmaceutically acceptable salts or N-oxides or solvates or deuterated derivative thereof:

The invention is also directed to a compound of the invention as described herein for use in the treatment of the human or animal body by therapy.

According to another embodiment the present invention covers pharmaceutical compositions comprising at least a compound of the invention, as hereinabove described, in admixture with pharmaceutically acceptable diluents or carriers.

In an embodiment of the present invention the pharmaceutical composition further comprises a therapeutically effective amount of one or more other therapeutic agents, in particular one or more drugs selected from the group consisting of corticosteroids, and PDE4 inhibitors.

It is also an embodiment of the present invention that the pharmaceutical composition is formulated for administration by inhalation.

The compounds of the present invention as hereinabove defined may also be combined with one or more other therapeutic agents, in particular one or more drugs selected from the group consisting of corticosteroids and PDE4 inhibitors, for simultaneous, separate or sequential use in the treatment of the human or animal body.

The invention is also directed to compounds of the present invention for use in the treatment of a pathological condition or disease associated with both β2 adrenergic receptor and muscarinic receptor activities such as a pulmonary disease. In particular the pulmonary disease is asthma or chronic obstructive pulmonary disease.

The pathological condition or disease can also be applied within the scope of the present invention to the treatment of a disease or condition selected from the group consisting of pre-term labor, glaucoma, neurological disorders, cardiac disorders, and inflammation, urological disorders such as urinary incontinence and gastrointestinal disorders such as irritable bowel syndrome or spastic colitis.

The invention is also directed to the use of compounds of the present invention for the manufacture of a medicament for the treatment of pathological condition or disease associated with one or both β2 adrenergic receptor and muscarinic receptor activities such as a pulmonary disease, in particular asthma or chronic obstructive pulmonary disease, pre-term labor, glaucoma, neurological disorders, cardiac disorders, inflammation, urological disorders and gastrointestinal disorders, preferably asthma and chronic obstructive pulmonary disease.

The invention is also directed to a method of treating these diseases, which comprises administering a therapeutically effective amount of a pharmaceutical composition comprising a dual β2 adrenergic receptor agonists and muscarinic receptor antagonists according to the present invention. The method further comprises administering a therapeutically effective amount of one or more other therapeutic agent selected from the group consisting of a corticosteroid and a PDE4 inhibitor.

The invention is also directed to a method of modulating the activity of a β2 adrenergic and/or a M3 receptor, the method comprising stimulating a β2 adrenergic receptor and/or blocking a M3 receptor with a modulatory amount of compounds of the present invention.

The term "therapeutically effective amount" refers to an amount sufficient to effect treatment when administered to a patient in need of treatment.

The term "treatment" as used herein refers to the treatment of a disease or medical condition in a human patient which includes:
(a) preventing the disease or medical condition from occurring, i.e., prophylactic treatment of a patient;
(b) ameliorating the disease or medical condition, i.e., causing regression of the disease or medical condition in a patient;
(c) suppressing the disease or medical condition, i.e., slowing the development of the disease or medical condition in a patient; or
(d) alleviating the symptoms of the disease or medical condition in a patient.

The phrase "disease or condition associated with β2 adrenergic receptor and muscarinic activities" includes all disease states and/or conditions that are acknowledged now, or that are found in the future, to be associated with both β2 adrenergic receptor and muscarinic receptor activity. Such disease states include, but are not limited to, pulmonary diseases, such as asthma and chronic obstructive pulmonary disease (including chronic bronchitis and emphysema), as well as neurological disorders and cardiac disorders. β2 adrenergic receptor activity is also known to be associated with pre-term labor (see International Patent Application Publication Number WO 98/09632), glaucoma and some types of inflammation (see International Patent Application Publication Number WO 99/30703 and Patent Application Publication Number EP 1 078 629).

On the other hand M3 receptor activity is associated with gastrointestinal-tract disorders such as Irritable bowel syndrome (IBS) (see, for ex., U.S. Pat. No. 5,397,800), GI ulcers, spastic colitis (see, for ex., U.S. Pat. No. 4,556,653); urinary-tract disorders such as urinary incontinence (see, for ex., J.Med.Chem., 2005, 48, 6597-6606), pollakiuria; motion sickness and vagally induced sinus bradycardia.

General Synthetic Procedures

The compounds of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal are described in T. W. Greene and G. M. Wuts, Protecting Groups in Organic Synthesis, Third Edition, Wiley, New York, 1999, and references cited therein.

The term "amino-protecting group" refers to a protecting group suitable for preventing undesired reactions at amino nitrogen. Representative amino-protecting groups include, but are not limited to, formyl; acyl groups, for example alkanoyl groups such as acetyl; alkoxycarbonyl groups such as tert-butoxycarbonyl (Boc); arylmethoxycarbonyl groups such as benzyloxycarbonyl (Cbz) and 9-fluorenylmethoxycarbonyl (Fmoc); arylmethyl groups such as benzyl (Bn), trityl (Tr), and 1,1-di-(4'-methoxyphenyl)methyl; silyl groups such as trimethylsilyl (TMS) and tert-butyldimethylsilyl (TBS); and the like.

The term "hydroxy-protecting group" refers to a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Processes for preparing compounds of the invention are provided as further embodiments of the invention and are illustrated by the procedures below.

One of the most convenient synthetic route for the preparation of compounds of formula (ID) is depicted in Scheme 1.

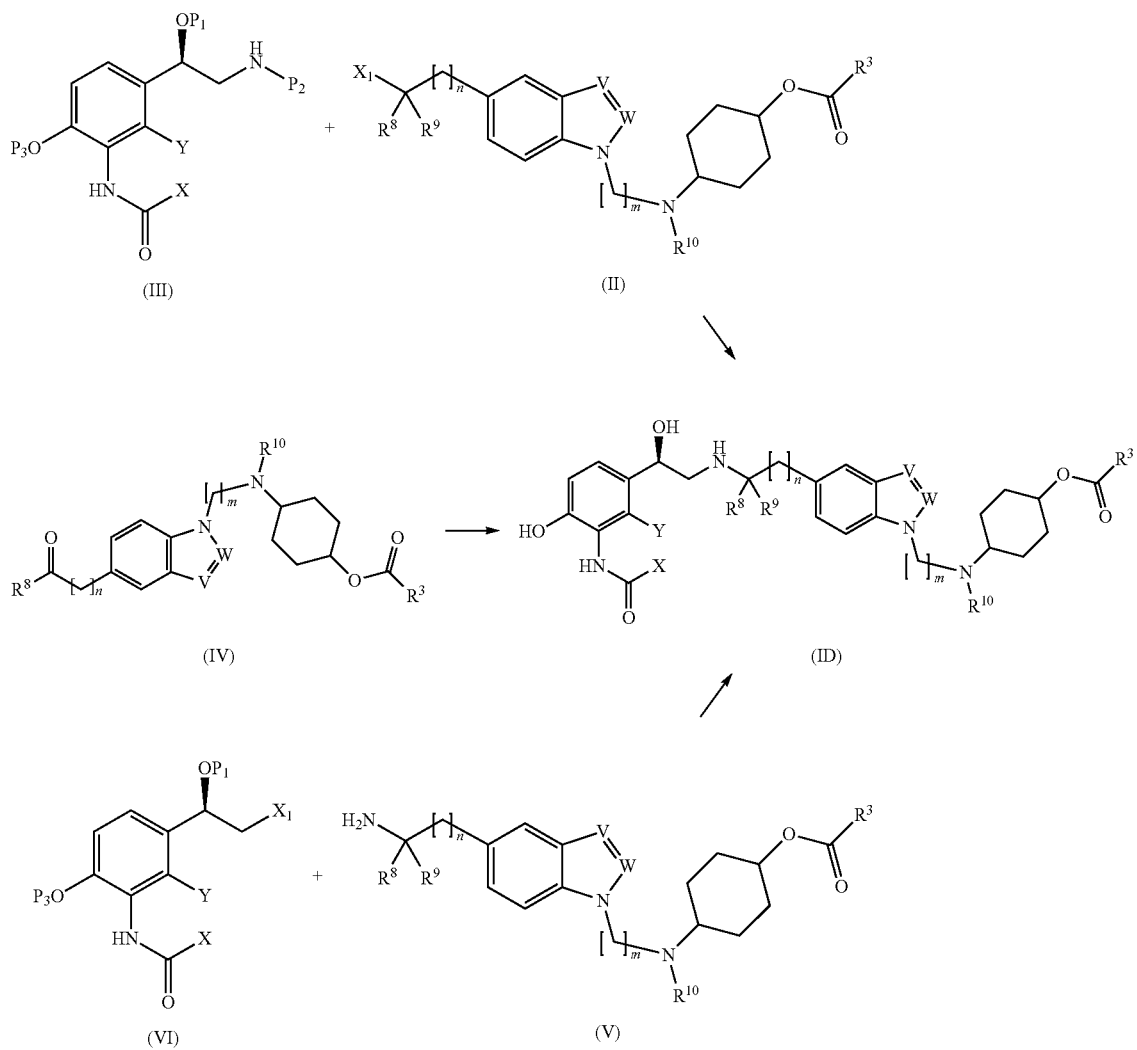

Scheme 1

Compounds of formula (ID) may be prepared by reacting Intermediates of formula (II), wherein $X_1$ represents a leaving group such as a halogen atom or an active ester as mesylate or tosylate, with intermediates of formula (III), wherein $P_1$ and $P_3$ independently represent a hydrogen atom or an oxygen-protecting group such as a silyl or benzyl ether and $P_2$ represents a hydrogen atom or a nitrogen-protecting group such as for example a benzyl group. This reaction is best carried out in an aprotic polar solvent such as dimethylformamide (DMF), 1-methyl-2-pyrrolidone or dimethylsulfoxide (DMSO) in a range of temperatures between room temperature and 200° C., in the presence of an acid scavenger such as sodium hydrogen carbonate or a tertiary amine.

Alternatively, compounds of formula (ID) may be prepared by reacting intermediates of formula (V) with intermediates of formula (VI) wherein $X_1$, $P_1$ and $P_3$ have the same meaning as disclosed above, following the same synthetic procedure disclosed above; and subsequently removing whichever protecting group present in the intermediate to provide a compound of formula (ID). Such deprotection processes involve, for example, a desilylation process, by using triethylamine trihydrofluoride, TBAF, hydrogen chloride or other acidic reagents in an inert solvent like THF in a range of temperatures between 0° C. and 50° C. The deprotection could also be carried out by a debenzylation process, for example, by hydrogenating the compound in the presence of a catalyst such as palladium on charcoal in an inert solvent like ethanol or THF or a mixture of solvents. This reaction is typically carried out at a hydrogen pressure between 10 and 60 psi and in a range of temperatures between room temperature and 50° C.

In another alternative way, compounds of formula (ID) with $R^9$=H may also be prepared by reacting intermediates of formula (IV) with intermediates of formula (III). This reaction is best carried out in a solvent or mixture of solvents like THF, methanol, dichloromethane or DMSO at a temperature between 0° C. and 60° C. using a hydride like sodium borohydride or sodium triacetoxyborohydride as reducing agent.

Intermediates of formula (II) may be prepared from commercially available starting materials and reagents using well known procedures, as depicted in Scheme 2.

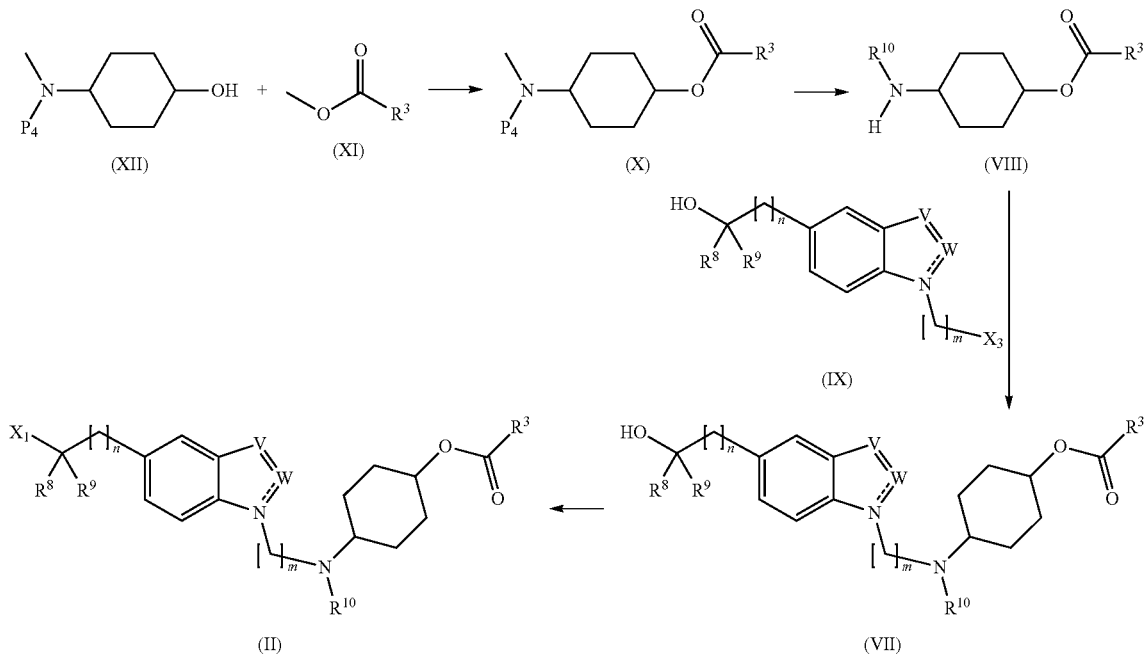

Intermediates of formula (II) may be prepared from alcohol derivatives of formula (VII) via acylation with sulphonyl halides in the presence of an acid scavenger or by halogenation with a variety of halogenating agents.

Intermediates of formula (VII) may be prepared by direct alkylation of an amine of formula (VIII) with the corresponding alkylating fragment (IX) wherein $X_3$ represents a leaving group such as a halogen atom or an active ester as mesylate or tosylate, in the presence of an acid scavenger such as a tertiary amine.

The amino-ester derivatives of formula (VIII) may be prepared by deprotecting compounds of formula (X), wherein $P_4$ represents a protecting group, for example, by removing tert-butoxycarbonyl group (BOC) in the presence of acidic media such as hydrogen chloride in THF.

Intermediates of formula (X) may be prepared by a transesterification process starting from literature-known aminoalcohol derivatives of formula (XII) and methyl esters derivative of formula (XI), typically in the presence of a base as sodium hydride and and by displacing the equilibrium by distillation of a solvent like toluene.

Intermediates of formula (III) are widely described in the literature (see, for example, US2004242622 example 6; WO2008149110 intermediate 65; US2007249674 example 3B), and may be prepared following the same synthetic procedure described therein.

Intermediates of formula (IV) may be prepared from commercially available starting materials and reagents using well known procedures, as depicted in Scheme 3.

Scheme 3

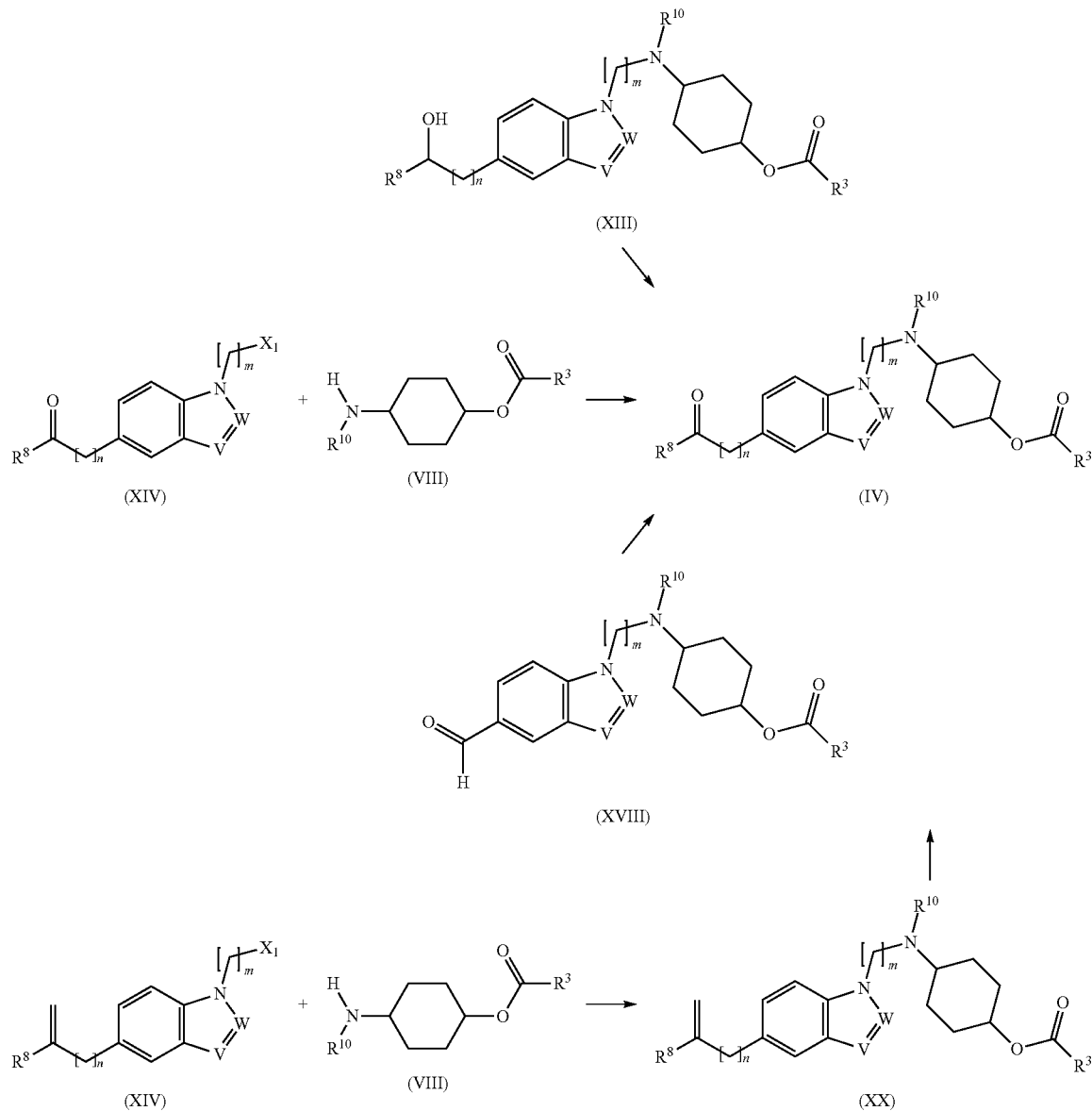

Intermediates of formula (IV) may be prepared either by oxidation of intermediates of formula (XIII) with an oxidizing agent such as manganese dioxide or Dess-Martin reagent or by direct alkylation of an intermediate of formula (VIII) with an alkylating agent of formula (XIV) in the presence of an acid scavenger.

Compounds (IV) wherein n=1 are also available by homologation of aldehydes (XVIII) through reaction with methoxymethyltriphenylphosphine in the presence of a base such as lithium bis(trimethylsilyl)amide and subsequent acidic hydrolysis of the intermediate enolic ether or by oxidation of the vinyl derivatives (XX), prepared in turn by alkylation of (VIII) with intermediates (XIX). This oxidation can be accomplished with a variety of agents, such as osmium tetroxide in the presence of N-methylmorpholine N-oxide.

Intermediates of formula (V) may be prepared from their N-protected homologues (XV) by a specific deprotecting process such as the treatment of N—BOC derivative with acidic media like hydrogen chloride in THF, as depicted in Scheme 4.

Scheme 4

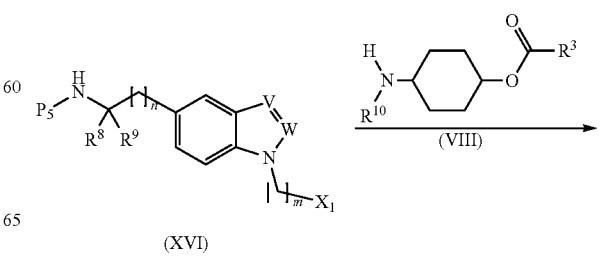

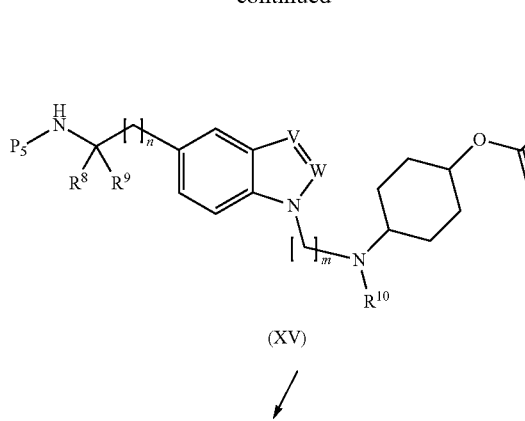

(XV)

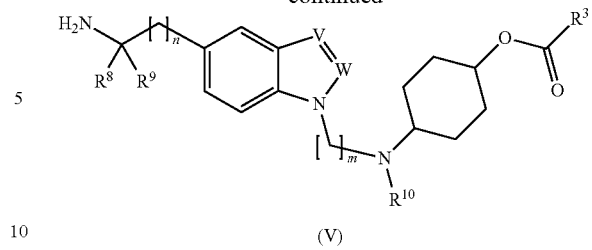

(V)

Intermediates of formula (XV) are in turn prepared from intermediates of formula (VIII) by procedures well known in the art, such as alkylation procedures with intermediates of formula (XVI) in the presence of an acid scavenger such as a tertiary amine.

Intermediates (XVIII) are obtained from known compounds as depicted in Scheme 5.

Scheme 5

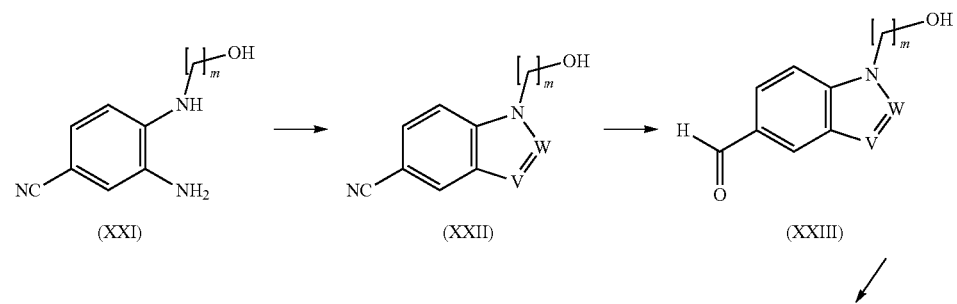

(XXI)  (XXII)  (XXIII)

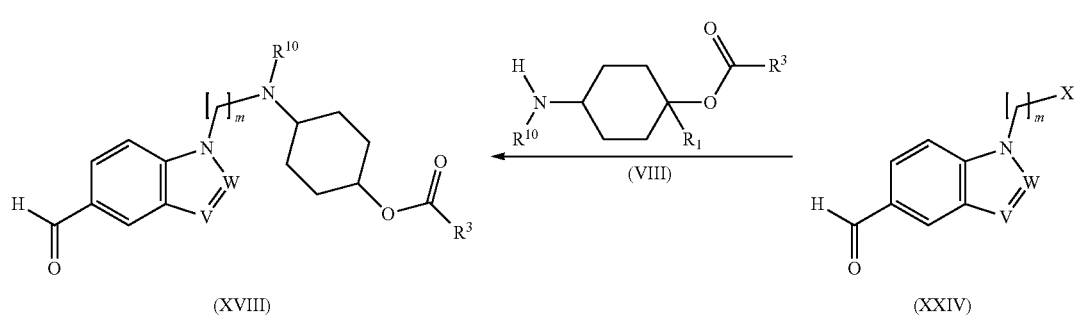

(XVIII)  (VIII)  (XXIV)

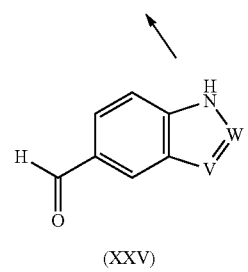

(XXV)

Compounds of formula (XXI) are transformed into the corresponding benzoimidazolones (XXII) (wherein W represents a —CO— and V represents a —NH—) by treatment with carbonylimidazole or triphosgene, or alternatively are transformed into the corresponding benzotriazoles (XXII) (wherein both W and V are —N—) by treatment with sodium nitrite in an acidic medium. Reduction of intermediate nitriles (XXII) with NiAl alloy in formic acid give raise to the intermediate aldehydes (XXIII), which in turn are transformed into the alkylating agents (XXIV) (X represents halide or active ester) and finally reacted with intermediate (VIII) to give intermediates (XVIII). Intermediates (XXIV) wherein W represents —CO— and V represent an oxygen atom, can also be obtained by direct N-alkylation of intermediates (XXV) with an α,ω-dihaloalkane in the presence of an acid scavenger.

When the linker of the compounds of the present invention is other than the benzoheterocyclic moiety, the same general synthetic scheme applies for the preparation of final compounds, as depicted in Scheme 6:

Synthetic scheme depicted in Scheme 6 is homologous to that depicted in Scheme 1 and represents the most convenient routes for the synthesis of compounds (XXIX) starting from the same synthons (III) and (VI) shown in scheme 1 and involving very similar chemical synthetic steps as described there. The definitions of the groups $X_1$, $A_1$, G, $L_1$, $A_2$ and R' are the same given above, whilst $A_3$ denotes a carbon chain with one less carbon atom than the chain $A_1$.

The preparation of the corresponding intermediates (XXVI) and (XXVII) is shown in the synthetic scheme represented in Scheme 7, being the synthetic steps close analogous of that shown in Schemes 2 and 3. The group $A_3$ in the general structure (XXVII) denotes a carbon chain with one carbon atom less than the $A_1$ group. P corresponds to an oxygen-protecting group.

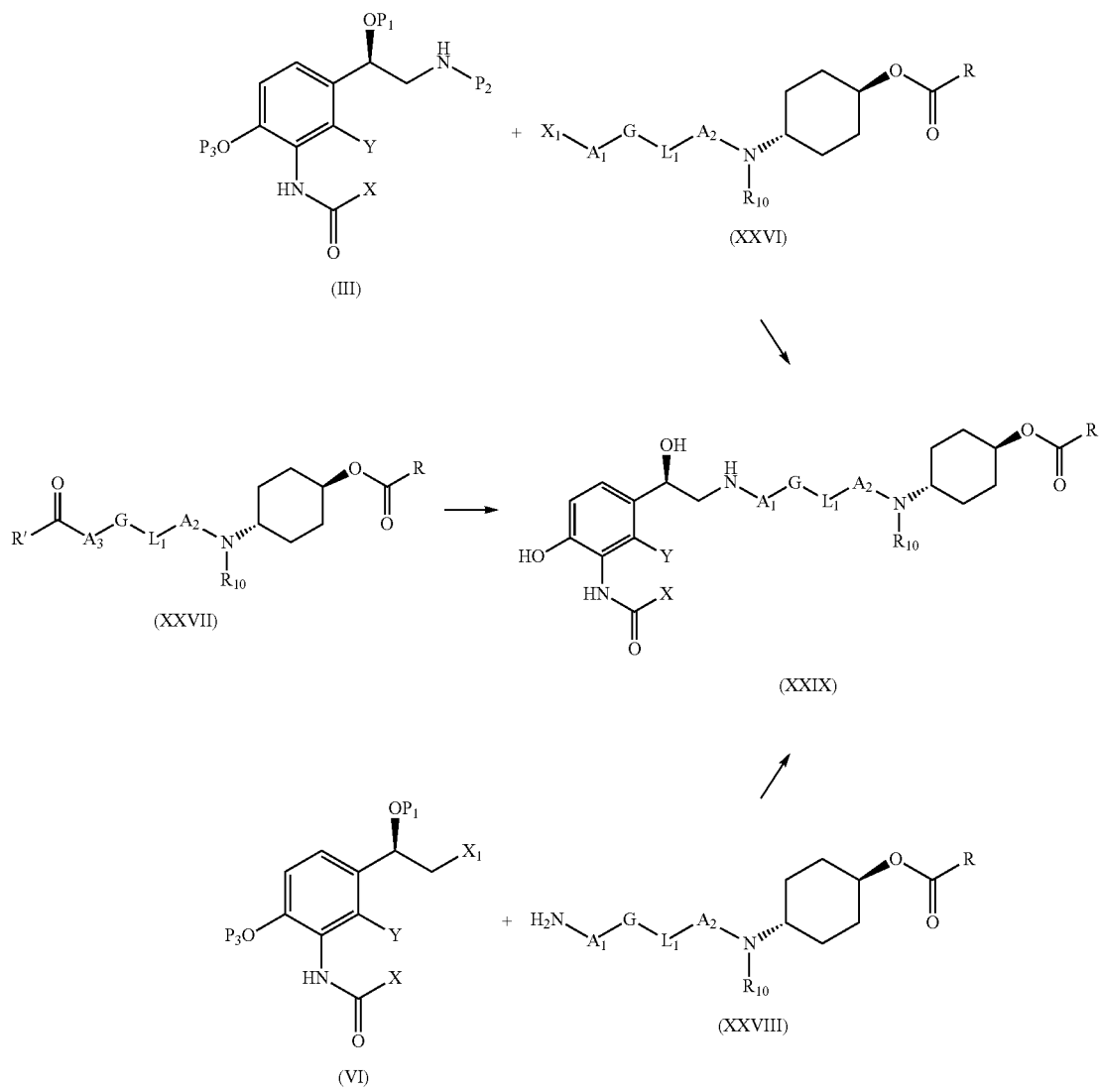

Scheme 6

Scheme 7

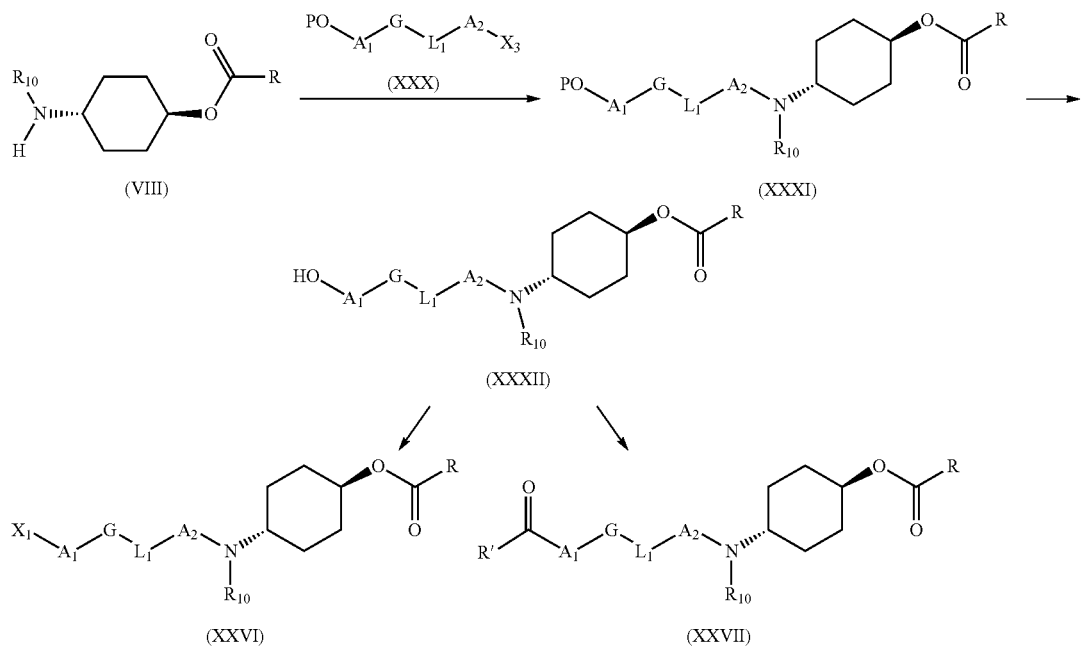

In the particular case of the group $L_1$ being defined as —CONR$^d$— the specific (XXXI) compounds (XXXVII) (being R$_d$ as defined above) may be prepared by the route shown in Scheme 8:

Scheme 8

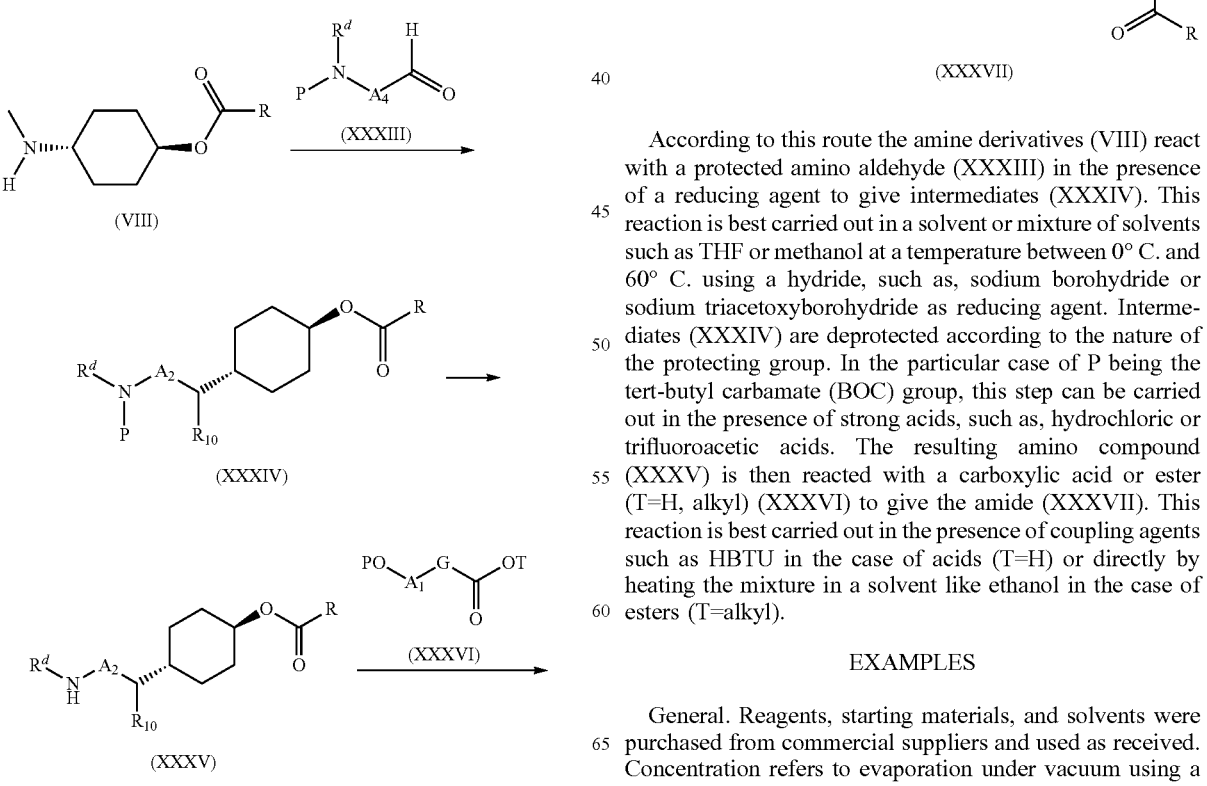

According to this route the amine derivatives (VIII) react with a protected amino aldehyde (XXXIII) in the presence of a reducing agent to give intermediates (XXXIV). This reaction is best carried out in a solvent or mixture of solvents such as THF or methanol at a temperature between 0° C. and 60° C. using a hydride, such as, sodium borohydride or sodium triacetoxyborohydride as reducing agent. Intermediates (XXXIV) are deprotected according to the nature of the protecting group. In the particular case of P being the tert-butyl carbamate (BOC) group, this step can be carried out in the presence of strong acids, such as, hydrochloric or trifluoroacetic acids. The resulting amino compound (XXXV) is then reacted with a carboxylic acid or ester (T=H, alkyl) (XXXVI) to give the amide (XXXVII). This reaction is best carried out in the presence of coupling agents such as HBTU in the case of acids (T=H) or directly by heating the mixture in a solvent like ethanol in the case of esters (T=alkyl).

EXAMPLES

General. Reagents, starting materials, and solvents were purchased from commercial suppliers and used as received. Concentration refers to evaporation under vacuum using a Büchi rotatory evaporator. Reaction products were purified, when necessary, by flash chromatography on silica gel (40-63 μm) with the solvent system indicated or using preparative HPLC conditions (see bellow description of two systems used). Spectroscopic data were recorded on a Varian Gemini 300 spectrometer. HPLC-MS were performed on a Gilson instrument equipped with a Gilson piston pump 321, a Gilson 864 vacuum degasser, a Gilson liquid handler 215, a Gilson 189 injection module, a Gilson Valvemate 7000, a 1/1000 splitter, a Gilson 307 make-up pump, a Gilson 170 diode array detector, and a Thermoquest Finnigan aQa detector.

HPLC System 1:

C-18 reversed phase column silica from MERCK, water/acetonitrile as eluents [0.1% v/v ammonium formate buffered] using a gradient from 0% to 100%.

HPLC System 2:

C-18 reversed phase column silica from MERCK, water/acetonitrile (without buffer) as eluents using a gradient from 0% to 100%.

Intermediate 1 tert-butyl (trans-4-hydroxycyclohexyl)carbamate

To a solution of (1R,4R)-4-aminocyclohexanol (15 g, 0.13 mol) in acetonitrile (240 mL) was added in portions di-tert-butyl dicarbonate (31.2 g, 0.14 mol). The mixture was stirred overnight at room temperature. The precipitate obtained was washed with hexane/ethyl acetate (3:1) and hexane giving the title compound as a white solid (83%).

$^1$H NMR (300 MHz, CHLOROFORM-d) δ ppm 1.17 (br. s., 2 H) 1.44 (br. s., 9 H) 1.32-1.40 (m, 2 H) 1.99 (br. s., 4 H) 3.44 (br. s., 1 H) 3.61 (br. s., 1H) 4.38 (br. s., 1 H)

Intermediate 2 trans-4-(Methylamino)cyclohexanol

To a mixture of lithium aluminium hydride (9 g, 0.23 mol) in tetrahydrofuran (425 mL) was added slowly tert-butyl (trans-4-hydroxycyclohexyl)carbamate (intermediate 1, 10 g, 0.046 mol). The mixture was refluxed overnight. Once the mixture was cooled to room temperature, 9 ml of water, 9 ml of 4N NaOH solution and 18 ml of water were carefully and successively dropped. The organic solvent was removed under reduced pressure and the crude obtained was dissolved with chloroform and dried over magnesium sulphate. The filtrate was evaporated to dryness and co evaporated with hexane to give the title compound as a white solid (89%). This intermediate is also described in *JMC*, 1987, 30(2), p313.

$^1$H NMR (300 MHz, CHLOROFORM-d) δ ppm 1.04-1.20 (m, 2 H) 1.25-1.40 (m, 2 H) 1.97 (br. s., 4 H) 2.27-2.40 (m, 1 H) 3.57-3.70 (m, 1 H)

Intermediate 3 tert-butyl (trans-4-hydroxycyclohexyl)methylcarbamate

To a solution of trans-4-(methylamino)cyclohexanol (intermediate 2, 5.3 g, 0.04 mol) in acetonitrile (92 mL) was added in portions di-tert-butyl dicarbonate (9.9 g, 0.04 mol). The mixture was stirred overnight at room temperature. The solvent was removed under reduced pressure and the crude was purified by column chromatography with silica gel, eluting with a mixture of chloroform/methanol (from 75:1 to 4:1)) to give the title compound as a colourless oil (87%).

$^1$H NMR (300 MHz, CHLOROFORM-d) δ □□ ppm 1.34-1.43 (m, 2 H) 1.46 (s, 9 H) 1.49-1.57 (m, 2 H) 1.70 (d, J=9.89 Hz, 2 H) 2.03 (br. s., 3 H) 2.71 (br. s., 3 H) 3.57 (br. s., 1 H)

Intermediate 4 trans-4-[(tert-butoxycarbonyl)(methyl)amino]cyclohexyl hydroxy(di-2-thienyl)-acetate To a solution of methyl hydroxy(di-2-thienyl)acetate (5.8 g, 0.02 mol) (prepared according to *Acta Chemica Scandinavica* 24 (1970) 1590-1596) in anhydrous toluene (95 mL) was first added a solution of tert-butyl (trans-4-hydroxycyclohexyl)-methylcarbamate (intermediate 3; 6 g, 0.02 mol) in anhydrous toluene (95 mL) and secondly sodium hydride (60%, 0.45 g, 0.01 mol). After few minutes the mixture was warmed to 155° C. and the solvent was distilled and simultaneously replaced. This procedure was carried on during 1 hour and a half. The mixture was cooled to room temperature and diluted with ether (300 mL). The organic layer was washed with sodium bicarbonate 4% (2×200 mL) and brine, dried, filtered and evaporated over reduced pressure giving the title compound as a yellow solid (69%), which was used in the next step without further purification.

LRMS (m/z): 452 (M+1)$^+$.

Intermediate 5 trans-4-(methylamino)cyclohexyl hydroxy(di-2-thienyl)acetate

To a solution of trans-4-[(tert-butoxycarbonyl)(methyl) amino]cyclohexyl hydroxy(di-2-thienyl)acetate (intermediate 4; 8.1 g, 0.01 mol) in dioxane (13.5 mL) was added hydrogen chloride 4M in dioxane (27 mL). The mixture was stirred at room temperature for 24 hours. The precipitate obtained was filtrated and washed with ether. The crude was dissolved in water and potassium carbonate was added until pH=8-9. The product was extracted with ethyl acetate and the organic layer was washed with brine, dried and evaporated to dryness giving the title compound as a white solid (78%).

LRMS (m/z): 352 (M+1)$^+$.

$^1$H NMR (300 MHz, CHLOROFORM-d) δ ppm 1.14-1.30 (m, 2 H) 1.42-1.57 (m, 2 H) 1.88-2.11 (m, 4 H) 2.36-2.48 (m, 1 H) 3.71 (s, 3 H) 4.82-4.95 (m, 1 H) 6.94-7.00 (m, 2 H) 7.14-7.19 (m, 2 H) 7.25-7.30 (m, 2 H)

Intermediate 6

2-oxo-2,3-dihydro-1,3-benzoxazole-6-carbonitrile

A mixture of 6-bromo-1,3-benzoxazol-2(3H)-one (2 g; 9.34 mmol) and copper (I) cyanide (1.42 g; 15.86 mmol) in 6 ml DMF is heated at 150° C. under nitrogen atmosphere for 22 hr. After cooling to room temperature, a solution of 1.55 g (31.6 mmol) of sodium cyanide in 32 ml water is added followed by 1 hr stirring. The system is extracted thoroughly with ethyl acetate, washed with brine, dried and concentrated in vacuo to provide 1.5 g (93% yield) of the title compound enough pure as to prosecute the syntesis.

Intermediate 7

2-oxo-2,3-dihydro-1,3-benzoxazole-6-carbaldehyde

A mixture of 2-oxo-2,3-dihydro-1,3-benzoxazole-6-carbonitrile (Intermediate 6, 220 mg; 1.37 mmol) and aluminium/nickel 1:1 alloy (223.6 mg; 2.61 mmol) in 2.25 ml of formic acid and 0.75 ml of water is stirred at 90° C. for 24 hr. The solid is filtered and washed with ethanol. The filtrate is concentrated in vacuo and dried overnight at 45° C. in a vacuum dessicator. The solid obtained (219 mg; 97% yield) is pure enough as to prosecute with the synthesis.

Intermediate 8

3-(3-bromopropyl)-2-oxo-2,3-dihydro-1,3-benzoxazole-6-carbaldehyde

A mixture of 290 mg (1.64 mmol) of 2-oxo-2,3-dihydro-1,3-benzoxazole-6-carbaldehyde (Intermediate 7), 272.8 mg (1.96 mmol) of 3-bromo-propan-1-ol, 514 mg (1.96 mmol) of triphenylphospine and 0.855 ml (1.96 mmol) of 40% toluene solution of DEAD in 7 ml THF is stirred overnight. After concentration in vacuo the residue is chromatographically purified over silicagel eluting with hexane/ethyl ether (100/0 to 0/100), obtaining 423 mg of the title product (58% purity; 52% total yield) that is used per se in the next synthetic step.

Intermediate 9 trans-4-[[3-(6-formyl-2-oxo-1,3-benzoxazol-3(2H)-yl)propyl](methyl)amino]cyclohexyl hydroxy(di-2-thienyl)acetate A solution of 418 mg (0.85 mmol) of 58% pure 3-(3-bromopropyl)-2-oxo-2,3-dihydro-1,3-benzoxazole-6-carbaldehyde (Intermediate 8), 250 mg (0.71 mmol) of trans-4-(methylamino)cyclohexyl hydroxy(di-2-thienyl)acetate (Intermediate 5) and 0.14 ml (1.01 mmol) of triethylamine in 8 ml acetonitrile and 6 ml THF is heated to 90° C. under argon atmosphere for 44 hr. After concentration in vacuo the residue is chromatographically purified over silicagel eluting with dichloromethane/EtOH (from 100/0 to 80/20), obtaining 376 mg of the title product (51% purity; 48% total yield) that is used per se in the next synthetic step.

Intermediate 10 trans-4-[{3-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]propyl}(methyl)amino]cyclohexyl hydroxy(di-2-thienyl)acetate A mixture of 370 mg (0.34 mmol) of 51% pure trans-4-[[3-(6-formyl-2-oxo-1,3-benzoxazol-3(2H)-yl)propyl](methyl)amino]cyclohexylhydroxy(di-2-thienyl)acetate (Intermediate 9), 167 mg (0.42 mmol) of 5-((1 R)-2-amino-1-{[tert-butyl(dimethyl)-silyl]oxy}ethyl)-8-hydroxyquinolin-2(1H)-one acetate (prepared according to preparation 8 from US20060035931), 0.075 ml (0.43 mmol) of diisopropilethylamine and 379 mg (1.79 mmol) of sodium triacetoxyborohydride in 2 ml MeOH and 1 ml THF is stirred under argon atmosphere for 24 hr at room temperature. After adding 20 ml of 4% aqueous solution of sodium hydrogen carbonate the system is extracted thrice with ethyl acetate and the organic solution washed thoroughly with 4% aqueous sodium hydrogen carbonate. After drying and concentrating, the residue is chromatographically purified over silicagel eluting with chloroform/EtOH (100/0 to 0/100). 133 mg of 88% pure title compound are obtained (39% yield).

Example 1 trans-4-[{3-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}(methyl)amino]cyclohexyl hydroxy(di-2-thienyl)acetate, dihydrofluoride 115 mg (0.12 mmol) of 88% pure trans-4-[{3-[6-({[(2R)-2-{[tert-butyl(dimethyl)silyl]oxy}-2-(8-hydroxy-2-oxo-1,2-dihydroquinolin-5-yl)ethyl]amino}methyl)-2-oxo-1,3-benzoxazol-3(2H)-yl]propyl}(methyl)amino]cyclohexyl hydroxy(di-2-thienyl)acetate (Intermediate 10) are dissolved in 3 ml THF. 0.075 ml (0.46 mmol) of triethylamine trihydrofluoride are added and the system stirred overnight at room temperature. The supernatant is discarded and the residue is washed (ultrasound bath) with 5 additional ml of THF and the supernatant is again discarded. Acetonitrile (5 ml) is added to the residue and after some stirring the solid is filtered and washed with acetonitrile and ethyl ether. 87 mg (94% yield) of pure title compound are obtained.

LRMS (m/z): 759 (M+1)$^+$.

$^1$H NMR (400 MHz, DMSO-$d_6$) δ ppm: 1.34 (m. 4H); 1.61-1.72 (b.s. 2H); 1.80 (t. 2H); 1.85-1.96 (b.s. 2H); 2.11 (s. 3H); 2.32-2.51 (b.s. 3H); 2.66-2.76 (b.s. 2H); 3.77-3.90 (c.s. 5H); 4.62-4.74 (b.s. 1H); 5.09-5.17 (b.s. 1H); 6.47 (d. J=12 Hz 1H); 6.89-7.01 (c.s. 3H); 7.04-7.09 (c.s. 3H); 7.19-7.29 (c.s. 4H); 7.36 (s. 1H); 7.44-7.49 (m. 2H); 8.13 (d. J=12 Hz 2H); 10.21-10.54 (b.s. 1H).

Intermediate 11

4-[(3-hydroxypropyl)amino]-3-nitrobenzonitrile

A mixture of 4-fluoro-3-nitrobenzonitrile (1.0 g; 6.02 mmol), 0.502 ml (6.62 mmol) of 3-amino-propan-1-ol and 1.15 ml (6.62 mmol) of diisopropylethylamine in 5 ml THF is stirred at rt for 1 hr (temperature raises somewhat at the beginning). After concentration in vacuo the residue is dissolved in 50 ml of ethyl acetate, washed with 50 ml of 4% aqueous sodium hydrogen carbonate and brine, dried and concentrated. 1.32 g of pure title compound as a solid are thus obtained (99% yield).

Intermediate 12

3-amino-4-[(3-hydroxypropyl)amino]benzonitrile

A mixture of 1.12 g (5.06 mmol) of 4-[(3-hydroxypropyl)amino]-3-nitrobenzonitrile (Intermediate 11) and 26.94 mg of 10% Pd on charcoal in 39 ml of EtOH is shaken in an hydrogen atmosphere (14 psi) for 20 hr at rt. After filtration and evaporation 1.012 g of the pure title compound are obtained.

Intermediate 13

1-(3-hydroxypropyl)-2-oxo-2,3-dihydro-1H-benzimidazole-5-carbonitrile 100 mg (0.52 mmol) of 3-amino-4-[(3-hydroxypropyl) amino]benzonitrile (Intermediate 12) are dissolved in 2.5 ml of 2N aqueous HCl and 1.5 ml of toluene are added. 150 mg (0.51 mmol) of triphosgene are added and the system is stirred at rt for 18 hr. After adding 75 additional mg of triphosgene and prosecuting the stirring for 1 hour 5 ml of brine and 25 ml of ethyl acetate are added and the system is stirred for 10 minutes. The organic layer is isolated and the aqueous one is extracted with 4×10 ml of ethyl acetate. The combined organic phases are washed with brine, dried and concentrated to give 106 mg (93% yield) of 100 pure (UPLC) title compound.

Intermediate 14

1-(3-hydroxypropyl)-2-oxo-2,3-dihydro-1H-benzimidazole-5-carbaldehyde

A mixture of 930 mg (4.28 mmol) of 1-(3-hydroxypropyl)-2-oxo-2,3-dihydro-1H-benzimidazole-5-carbonitrile (Intermediate 13) and 949 mg of Ni—Al alloy 1:1 in 7.3 ml of 75% formic acid in water is stirred at 90° C. for 6.5 hr. After filtration, the residue is again dissolved in 7.3 ml of 75% formic acid, 949 mg of Ni—Al alloy are added and the system is stirred at 90° C. for 1 hr. After filtration, 5 ml of 2N NaOH and 5 ml of EtOH are added and the system is stirred at rt overnight. The pH is made 6-7 by addition of 2N HCl and the solution is concentrated. The residue is chromatographically purified over silicagel eluting with hexane/EtOH (100/0 to 0/100). 0.91 g of pure title compound are obtained (96% yield).

Intermediate 15

1-(3-bromopropyl)-2-oxo-2,3-dihydro-1H-benzimidazole-5-carbaldehyde 1185 mg (5.38 mmol) of 1-(3-hydroxypropyl)-2-oxo-2,3-dihydro-1H-benzimidazole-5-carbaldehyde (Intermediate 14) are suspended in 56 ml of dichloromethane. 2285 mg (6.89 mmol) of carbon tetrabromide and then 6890 mg of polymer-supported triphenyl phosphine (1 mmol/g; 6.89 mmol) are added. The mixture is shaken at rt for 24 hr. The polymer is filtered and sequentially washed with dichloromethane, EtOH and MeOH. The filtrates are concentrated and the residue (2.2 g) is chromatographically purified over silicagel eluting with chloroform/EtOH (100/0 to 90/10). 0.3 g of pure title compound are obtained (20% yield).

Intermediate 16 trans-4-[[3-(5-formyl-2-oxo-2,3-dihydro-1H-benzimidazol-1-yl)propyl](methyl) amino]cyclohexyl hydroxy(di-2-thienyl)acetate A mixture of 179 mg (0.56 mmol) of 1-(3-bromopropyl)-2-oxo-2,3-dihydro-1H-benzimidazole-5-carbaldehyde (Intermediate 15), 163 mg (0.46 mmol) of trans-4-(methylamino)cyclohexyl hydroxy(di-2-thienyl)acetate (Intermediate 5) and 0.09 ml (0.65 mmol) of triethylamine in 6 ml acetonitrile and 4 ml THF is stirred at 90° C. overnight. After concentration the residue (325 mg) is chromatographically purified over silicagel eluting with hexane to ethyl ether/EtOH 90/10 and again with C-18 reversed phase column silica from MERCK, using water to acetonitrile/MeOH as eluents with a gradient from 0% to 100%. 94 mg of pure title compound are thus obtained (36% yield).

Intermediate 17 trans-4-[{3-[5-({[(2R)-2-{[tert-butyl(dimethyl)silyl]oxy}-2-(8-hydroxy-2-oxo-1,2-dihydroquinolin-5-yl)ethyl]amino}methyl)-2-oxo-2,3-dihydro-1H-benzimidazol-1-yl]propyl}(methyl)amino]cyclohexyl hydroxy(di-2-thienyl)acetate 85 mg (0.15 mmol) of trans-4-[[3-(5-formyl-2-oxo-2,3-dihydro-1H-benzimidazol-1-yl)propyl](methyl) amino]cyclohexyl hydroxy(di-2-thienyl)acetate (Intermediate 16) and 80 mg (0.20 mmol) of 5-((1 R)-2-amino-1-{[tert-butyl(dimethyl)-silyl]oxy}ethyl)-8-hydroxyquinolin-2(1H)-one acetate (prepared according to preparation 8 from US20060035931) are dissolved in 2 ml MeOH and 1 ml THF. After adding 0.04 ml (0.23 mmol) of diisopropylethylamine and 100 mg (0.47 mmol) of sodium triacetoxyborohydride the mixture is stirred overnight under argon atmosphere at rt. After adding 100 mg more of sodium triacetoxyborohydride the stirring is prosecuted for 48 hr. After concentrating in vacuo the residue is partitioned in ethyl acetate/4% aqueous sodium hydrogen carbonate solution. A yellowish solid is filtered, dissolved in chloroform and washed with 4% NaHCO3. The combined organic phases are dried and concentrated. The residue is chromatographically purified over silicagel eluting with chloroform/EtOH/Et3N (100/0/0.1 to 0/100/0.1). 96 mg of 71% pure title compound are obtained (51% yield) and used per se in the next synthetic step.

Example 2 trans-4-[{3-[5-({[(2R)-2-hydroxy-2-(8-hydroxy-2-oxo-1,2-dihydroquinolin-5-yl)ethyl]amino}methyl)-2-oxo-2,3-dihydro-1H-benzimidazol-1-yl]propyl}(methyl)amino]cyclohexyl hydroxy(di-2-thienyl) acetate dihydrofluoride 95 mg (0.12 mmol) of 71% pure trans-4-[{3-[5-({[(2R)-2-{[tert-butyl(dimethyl)silyl]oxy}-2-(8-hydroxy-2-oxo-1,2-dihydroquinolin-5-yl)ethyl]amino}methyl)-2-oxo-2,3-dihydro-1H-benzimidazol-1-yl]propyl}(methyl)amino]cyclohexyl hydroxy(di-2-thienyl)acetate (Intermediate 17) are dissolved in 2 ml THF. 0.05 ml (0.31 mmol) of triethylamine trihydrofluoride are added and the system stirred overnight at room temperature. The supernatant is discarded and the residue is washed with 2×10 additional ml of THF and the supernatant is again discarded. Acetonitrile (5 ml) is added to the residue and the solid is stirred for 2 hr, aged overnight, filtered and washed with acetonitrile. The residue is chromatographically purified with C-18 reversed phase column silica from MERCK, using water to acetonitrile/MeOH as eluents with a gradient from 0% to 100%. 31.8 mg of pure title compound are thus obtained (51% yield).

LRMS (m/z): 758 (M+1)$^+$.

$^1$H NMR (400 MHz, DMSO-d$_6$) δ ppm: 1.35 (m. 6H); 1.61-1.77 (b.s. 5H); 1.85-1.97 (b.s. 2H); 2.12 (s. 3H); 2.32-2.45 (b.s. 4H); 2.68-2.74 (b.s. 2H); 3.72-3.86 (c.s. 3H); 4.62-4.73 (b.s. 1H); 5.06-5.14 (b.s. 1H); 6.47 (d. J=12 Hz 1H); 6.90 (d. J=6 Hz 1H); 6.95-7.09 (c.s. 8H); 7.23-7.30 (b.s.

1H); 7.47 (d. J=6 Hz 1H); 8.06 (d. J=12 Hz 1H); 10.26-10.49 (b.s. 1H); 10.80-10.88 (b.s. 1H).

Intermediate 18

1-(3-hydroxypropyl)-1H-1,2,3-benzotriazole-5-carbonitrile 100 mg (0.52 mmol) of 3-amino-4-[(3-hydroxypropyl)amino]benzonitrile (Intermediate 12) are suspended in 0.5 ml of 5N aqueous HCl. After cooling externally with an ice/water bath, a solution of 54.12 mg (0.78 mmol) of sodium nitrite in 0.4 ml water is added dropwise with stirring. After 3.5 hr excess water is added and the solid is extracted with dichloromethane, washed with water, dried and concentrated to give 104 mg of pure title compound (96% yield).

Intermediate 19

1-(3-hydroxypropyl)-1H-1,2,3-benzotriazole-5-carbaldehyde

A mixture of 500 mg (2.47 mmol) of 1-(3-hydroxypropyl)-1H-1,2,3-benzotriazole-5-carbonitrile (Intermediate 18) and 550 mg of Ni—Al alloy 1:1 in 5.55 ml of 75% formic acid in water is stirred at 90° C. for 2.5 hr. After filtration and evaporation 10 ml of 2N NaOH and 10 ml of EtOH are added to the residue and the system is stirred at rt for 1.5 hr. The pH is made 6-7 by addition of 2N HCl and the system is extracted thoroughly with ethyl acetate. After washing with water, drying and concentrating, 0.35 g of 80% pure title compound (55% yield).

Intermediate 20

1-(3-bromopropyl)-1H-1,2,3-benzotriazole-5-carbaldehyde 200 mg (0.975 mmol) of 1-(3-bromopropyl)-1H-1,2,3-benzotriazole-5-carbaldehyde (Intermediate 19) are dissolved in 10.5 ml of dichloromethane. 388 mg (1.17 mmol) of carbon tetrabromide are added and the solution cooled externally with an ice/water bath. 307 mg (1.17 mmol) of triphenylphosphine are slowly added and the system is stirred for 20 min with external cooling and 2 hr at rt. After addition of 0.5 more equivalents of both carbon tetrabromide and triphenylphosphine and additional stirring for 10 min with the external cooling and 1 hr at rt the solvents are eliminated in vacuo and the residue is chromatographically purified over silicagel eluting with hexane/ethyl ether (100/0 to 0/100). 195 mg of pure title compound are obtained (74% yield).

Intermediate 21 trans-4-[[3-(5-formyl-1H-1,2,3-benzotriazol-1-yl)propyl](methyl)amino]cyclohexyl hydroxy(di-2-thienyl)acetate A mixture of 152.56 mg (0.57 mmol) of 1-(3-bromopropyl)-1H-1,2,3-benzotriazole-5-carbaldehyde (Intermediate 20), 200 mg (0.57 mmol) of trans-4-(methylamino) cyclohexyl hydroxy(di-2-thienyl)acetate (Intermediate 5) and 0.138 ml 0.80 mmol) of diisopropylethylamine in 25 ml acetonitrile was stirred under argon at 75° C. for 17 hr and at 90° C. for 24 hr. After concentration in vacuo, the residue is chromatographically purified over silicagel eluting with chloroform/EtOH (100/0 to 90/10) to give 157 mg of pure title compound (51% yield).

Intermediate 22 trans-4-[{3-[5-({[(2R)-2-{[tert-butyl(dimethyl)silyl]oxy}-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate 132 mg (0.245 mmol) of trans-4-[[3-(5-formyl-1H-1,2,3-benzotriazol-1-yl)propyl](methyl)amino]cyclohexyl hydroxy(di-2-thienyl)acetate (Intermediate 21) and 106.3 mg (0.269 mmol) of 5-((1 R)-2-amino-1-{[tert-butyl(dimethyl)-silyl]oxy}ethyl)-8-hydroxyquinolin-2(1H)-one acetate (prepared according to preparation 8 from US20060035931) are dissolved in 1.6 ml MeOH and 0.8 ml THF. After adding 0.05 ml (0.29 mmol) of diisopropylethylamine and 76.9 mg (0.36 mmol) of sodium triacetoxyborohydride the mixture is stirred overnight under argon atmosphere at rt. After successive addition of 230 additional mg (1.08 mmol) of reducing agent, stirring for 3 hr and 76.9 mg (0.36 mmol) more and stirring for 2 hr the solvents are eliminated in vacuo and the residue (0.57 g) is stirred with chloroform, filtered and the solid discarded. The filtrate is concentrated and partitioned between 50 ml of ethyl acetate and 10 ml of 4% solution of sodium hydrogen carbonate. The organic solution is washed again with NaHCO3 solution, dried and concentrated to give 210 mg of 91% pure title compound (yield 91%) that is used per se in the next synthetic step.

Example 3 trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate dihydrofluoride 205 mg (0.218 mmol) of 91% pure trans-4-[{3-[5-({[(2R)-2-{[tert-butyl(dimethyl) silyl]oxy}-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl) acetate (Intermediate 22) are dissolved in 2 ml THF. 0.145 ml (0.89 mmol) of triethylamine trihydrofluoride are added and the system stirred overnight at room temperature. The supernatant is discarded and the residue is washed with 2×3 additional ml of THF and the supernatant is again discarded. Acetonitrile (4 ml) is added to the residue and the solid is stirred for 30 min, filtered and washed with more acetonitrile. After drying overnight at 40° C. 164 mg of pure title compound are thus obtained (96% yield).

LRMS (m/z): 743 (M+1)$^+$.

$^1$H NMR (400 MHz, DMSO-d$_6$) δ ppm: 1.32 (m. 5H); 1.59-1.69 (b.s. 3H); 1.84-1.94 (b.s. 2H); 2.01 (m. 2H); 2.11 (s. 3H); 2.26-2.40 (c.s. 4H); 2.60-2.75 (c.s. 2H); 3.90 (s. 2H); 4.34-4.42 (b.s. 1H); 4.67 (m. 4H); 5.04-5.11 (m. 1H); 5.28-5.46 (b.s. 1H); 6.40 (d. J=12 Hz 1H); 6.86-6.93 (c.s. 1H); 6.94-7.00 (c.s. 2H); 7.03-7.10 (c.s. 4H); 7.19-7.34 (b.s. 1H); 7.44-7.48 (m. 2H); 7.49-7.54 (m. 1H); 7.74-7.80 (m. 1H); 7.92 (s. 1H); 8.10 (d. J=12 Hz 1H); 10.10-10.51 (b.s. 1H).

Intermediate 23

1-(3-bromopropyl)-1H-indole-5-carbaldehyde 0.70 g (30.31 mmol) of 60% sodium hydride suspension are added to 14 ml of anhydrous DMF and a solution of 2.40 g (16.53 mmol) of 1H-indole-3-carbaldehyde in 10 ml of DMF added dropwise. After 45 min of stirring at room temperature the solution is cooled externally with an ice/water bath and a solution of 2.52 ml (5.01 g; 24.80 mmol) of 1,3-dibromopropane in 6 ml of DMF added dropwise. The solution is stirred at room temperature for 2 hr before adding 10 ml of water and 10 ml of 2N HCl. The suspension is extracted thrice with ethyl ether, washed with water, dried and concentrated in vacuo. The residue is chromatographically purified (hexane to hexane/EtAcO 4:1) to give 1.4 g of the pure title compound (33% yield).

Intermediate 24 trans-4-[[3-(5-formyl-1H-indol-1-yl)propyl](methyl)amino]cyclohexyl hydroxy(di-2-thienyl)acetate A mixture of 1.27 g (4.78 mmol) of 1-(3-bromopropyl)-1H-indole-5-carbaldehyde (intermediate 23), 1.40 g (3.98 mmol) of trans-4-(methylamino)cyclohexyl hydroxy(di-2-thienyl)acetate (intermediate 5) and 0.77 ml (0.56 g; 5.5 mmol) of triethylamine in 6 ml MeCN and 6 ml THF is stirred at 90° C. overnight under argon. After concentrating in vacuo the residue is chromatographically purified eluting with $Cl_3CH$ to $Cl_3CH/MeOH$ 95:5 to give 1.6 g (75% yield) of pure title compound.

Intermediate 25 trans-4-[{3-[5-({[(2R)-2-{[tert-butyl(dimethyl)silyl]oxy}-2-(8-hydroxy-2-oxo-1,2-dihydroquinolin-5-yl)ethyl]amino}methyl)-1H-indol-1-yl]propyl}(methyl)amino]cyclohexyl hydroxy(di-2-thienyl)acetate A mixture of 190 mg (0.35 mmol) of trans-4-[[3-(5-formyl-1H-indol-1-yl)propyl](methyl)amino]cyclohexyl hydroxy(di-2-thienyl)acetate (intermediate 24), 174. 59 mg (0.44 mmol) of 5-((1 R)-2-amino-1-{[tert-butyl(dimethyl)silyl]oxy}ethyl)-8-hydroxyquinolin-2(1H)-one acetate (prepared according to preparation 8 from US20060035931), 0.077 ml (0.44 mmol) of diisopropilethylamine and 243.8 mg (1.15 mmol) of sodium triacetoxyborohydride in 2 ml of MeOH and 1 ml THF is stirred under argon atmosphere for 2.5 hr at room temperature. After adding 25 ml of 4% aqueous solution of sodium hydrogen carbonate the system is extracted thrice with ethyl acetate and the organic solution washed thoroughly with 4% aqueous sodium hydrogen carbonate. After drying and concentrating, the residue is chromatographically purified over silicagel eluting with chloroform/EtOH (100/0 to 90/10). 177 mg of 94% pure title compound are obtained (55% yield).

Example 4 trans-4-[{3-[5-({[(2R)-2-hydroxy-2-(8-hydroxy-2-oxo-1,2-dihydroquinolin-5-yl)ethyl]amino}methyl)-1H-indol-1-yl]propyl}(methyl)amino]cyclohexyl hydroxy(di-2-thienyl)acetate dihydrofluoride 170 mg (0.20 mmol) of 91% pure trans-4-[{3-[5-({[(2R)-2-{[tert-butyl(dimethyl)silyl]oxy}-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate (Intermediate 22) are dissolved in 7 ml THF. 0.08 ml (0.78 mmol) of triethylamine trihydrofluoride are added and the system stirred overnight at room temperature. The supernatant is discarded and the residue is washed with $2 \times^3$ additional ml of THF and the supernatant is again discarded. Acetonitrile (4 ml) is added to the residue and the solid is stirred for 30 min, filtered and washed with more acetonitrile. After drying overnight at rt 146 mg of 98% pure title compound are thus obtained (92% yield).

LRMS (m/z): 741 (M+1)+.

$^1$H NMR (400 MHz, DMSO-d6) δ ppm: 1.35 (m. 5H); 1.60-1.73 (b.s. 3H); 1.79-1.95 (m. 5H); 2.00-2.16 (c.s. 4H); 2.27-2.41 (b.s. 2H); 2.66-2.83 (b.s. 3H); 3.53-3.65 (c.s. 1H); 4.00 (s. 2H); 4.15 (m. 2H); 4.66 (m. 1H); 5.17 (m. 1H); 6.40 (b.s. 2H); 6.90 (m. 1H); 6.98 (m. 1H); 7.07 (b.s. 3H); 7.14-7.49 (c.s. 6H); 7.55 (s. 1H); 8.02 (d. J=12 Hz 1H); 9.10-10.70 (b.s. 1H).

Intermediate 26

4-[(tetrahydro-2H-pyran-2-yloxy)methyl]benzonitrile

To a solution of 4-(hydroxymethyl)benzonitrile (1 g, 7.51 mmol) in dry $CH_2Cl_2$ (25 mL) under argon was added PPTs (190 mg, 0.76 mmol) and 3,4-dihydro-2H-pyran (0.824 mL, 9.01 mmol). The reaction was stirred at room temperature under argon for 4h. The reaction mixture was evaporated and the residue treated with water (80 mL) and Et20 (150 mL). The organic layer was separated and the aqueous layer was extracted with Et20 (2×100 mL). The combined organic layers were washed with brine and dried over sodium sulphate. Removal of the solvent under reduced pressure afforded 1.86 g of a colourless oil. The crude obtained was purified by column chromatography with n-Hexane (A) and EtOAc (B) as eluents (0% to 25%). The appropriate fractions were collected and the solvent removed afford the title compound (1.53 g, 91%) as colourless oil.

LRMS (m/z): 218 (M+1)$^+$.

Intermediate 27

N-hydroxy-4-[(tetrahydro-2H-pyran-2-yloxy)methyl]benzenecarboximidamide

To a suspension of hydroxylamine hydrochloride (365 mg, 5.25 mmol) in EtOH (3 mL) was added $Et_3N$ (0.78 mL, 5.6 mmol) at room temperature under argon. A white precipitate formed. It was stirred at that temperature for 40 minutes. Then 4-[(tetrahydro-2H-pyran-2-yloxy)methyl]benzonitrile (Intermediate 26; 0.76 g, 3.5 mmol) in EtOH (2 mL) was added dropwise; the reaction mixture became clear. It was stirred at RT overnight. The crude obtained was purified by column chromatography with $CH_2Cl_2$ (A) and $CH_2Cl_2$/MeOH (95:5) (B) as eluents (0% to 80% B). The appropriate fractions were collected and the solvent removed to afford 1.25 g of sticky oil with some solids. It was dissolved in EtOAc/$H_2O$ (1:1, 150 mL). The organic layer was washed again with $H_2O$ (50 mL) and brine. It was dried over sodium sulphate, filtered and evaporated to afford the title compound (840 mg, 95%) as sticky oil.

LRMS (m/z): 251 (M+1)$^+$.

Intermediate 28

5-(3-bromopropyl)-3-{4-[(tetrahydro-2H-pyran-2-yloxy)methyl]phenyl}-1,2,4-oxadiazole To a solution of N-hydroxy-4-[(tetrahydro-2H-pyran-2-yloxy)methyl]benzene-carboximidamide (Intermediate 27; 211 mg, 0.84 mmol) in DCM (3 mL) was added DIEA (0.176 mL, 1.01 mmol). The mixture was cooled to 0° C. and a solution of 4-bromobutanoyl chloride (0.108 mL, 0.88 mmol) in DCM (1 mL) was added dropwise. The mixture was stirred overnight at room temperature. The solvent was removed under reduced pressure and the crude obtained was purified by column chromatography with silica gel, eluting with a mixture of Hexane: ether give the title compound as a solid (198 mg, 53%).
LRMS (m/z): 382 (M+1)$^+$

Intermediate 29 trans-4-{methyl[3-(3-{4-[(tetrahydro-2H-pyran-2-yloxy)methyl]phenyl}-1,2,4-oxadiazol-5-yl)propyl]amino}cyclohexyl hydroxy(di-2-thienyl)acetate Obtained as a solid (152 mg, 42%) from 5-(3-bromopropyl)-3-{4-[(tetrahydro-2H-pyran-2-yloxy)methyl]phenyl}-1,2,4-oxadiazole (Intermediate 28; 195 mg, 0.51 mmol), trans-4-(methylamino)cyclohexyl hydroxy(di-2-thienyl)acetate (Intermediate 5; 209 mg, 0.51 mmol) and Et$_3$N (0.178 mL, 1.02 mmol) following the experimental procedure as described for Intermediate 9 and the crude obtained was purified by column chromatography with silica gel, eluting with a mixture of Chloroform: Ethanol.
LRMS (m/z): 652 (M+1)$^+$

Intermediate 30 trans-4-[(3-{3-[4-(hydroxymethyl)phenyl]-1,2,4-oxadiazol-5-yl}propyl)(methyl)amino]cyclohexyl hydroxy(di-2-thienyl)acetate To a solution of trans-4-{methyl[3-(3-{4-[(tetrahydro-2H-pyran-2-yloxy)methyl]phenyl}-1,2,4-oxadiazol-5-yl)propyl]amino}cyclohexyl hydroxy(di-2-thienyl)acetate (Intermediate 29; 147 mg, 0.21 mmol) in anh tetrahydrofurane (3.5 mL) was added hydrochloric acid (1M, 0.627 mL). The mixture was stirred overnight at room temperature. A solution of saturated bicarbonate was added into the mixture and then extracted with ethyl acetate. The organics layers were combined, washed with brine, dried, filtered and the organic solvent was removed under reduced pressure. The crude obtained was purified by column chromatography with silica gel, eluting with a mixture of Chloroform: Ethanol to give the title compound (89 mg, 75%)
LRMS (m/z): 568 (M+1)$^+$

Intermediate 31 trans-4-[{3-[3-(4-formylphenyl)-1,2,4-oxadiazol-5-yl]propyl}(methyl)amino]cyclohexyl hydroxy(di-2-thienyl)acetate To a solution of trans-4-[(3-{3-[4-(hydroxymethyl)phenyl]-1,2,4-oxadiazol-5-yl}propyl)(methyl)amino]cyclohexyl hydroxy(di-2-thienyl)acetate (Intermediate 30; 78 mg, 0.14 mmol) in CHCl$_3$ (2 mL, amylene stabilized) was added portion wise manganese oxide (132 mg, 1.52 mmol). The reaction mixture was stirred at 45° C. for 4h. The cooled reaction mixture was filtered through a syringe filtered, washed with more CHCl$_3$ (20 mL) and the solvent was removed under reduced pressure to afford the title compound (78 mg, 98%) as a light-brown oil. The compound was used in the next step without further purification.
LRMS (m/z): 566 (M+1)$^+$

Intermediate 32 trans-4-[(3-{3-[4-({[(2R)-2-{[tert-butyl(di methyl)silyl]oxy}-2-(8-hydroxy-2-oxo-1,2-dihydroquinolin-5-yl)ethyl]amino}methyl)phenyl]-1,2,4-oxadiazol-5-yl}propyl)(methyl)amino]cyclohexyl hydroxy(di-2-thienyl)acetate Obtained as a off-white solid (35 mg, 29%) from trans-4-[{3-[3-(4-formylphenyl)-1,2,4-oxadiazol-5-yl]propyl}(methyl)amino]cyclohexyl hydroxy(di-2-thienyl)acetate (74 mg, 0.13 mmol), 5-((1 R)-2-amino-1-{[tert-butyl(dimethyl)-silyl]oxy}ethyl)-8-hydroxyquinolin-2(1H)-one acetate (prepared according to preparation 8 from US20060035931; 62 mg, 0.16 mmol), DIEA (28 μL, 0.16 mmol) and sodium triacetoxyborohydride (62 mg, 0.28 mmol) following the procedure as described for Intermediate 10 and the crude obtained was purified by C-18 reversed phase column silica, using water to acetonitrile/MeOH as eluents with a gradient from 0% to 100%.
LRMS (m/z): 885 (M+1)$^+$

Example 5 trans-4-[(3-{3-[4-({[(2R)-2-hydroxy-2-(8-hydroxy-2-oxo-1,2-dihydroquinolin-5-yl)ethyl]amino}methyl)phenyl]-1,2,4-oxadiazol-5-yl}propyl)(methyl)amino]cyclohexyl hydroxy(di-2-thienyl)acetate dihydrofluoride Obtained as a white solid (28 mg, 85%) from trans-4-[(3-{3-[4-({[(2R)-2-{[tert-butyl(dimethyl)silyl]oxy}-2-(8-hydroxy-2-oxo-1,2-dihydroquinolin-5-yl)ethyl]amino}-methyl)phenyl]-1,2,4-oxadiazol-5-yl}propyl)(methyl)amino]cyclohexyl hydroxy(di-2-thienyl)acetate (35 mg, 0.04 mmol) and triethylamine trihydrofluoride (30 μL, 0.19 mmol) following the experimental procedure as described for Example 1.
LRMS (m/z): 770 (M+1)$^+$
$^1$H NMR (300 MHz, dmso) δ 8.13 (d, J=10.1 Hz, 1H), 7.94 (d, J=8.2 Hz, 2H), 7.49 (dd, J=17.2, 6.5 Hz, 3H), 7.25 (s, 1H), 7.07 (d, J=8.3 Hz, 3H), 7.02-6.85 (m, 3H), 6.47 (d, J=10.0 Hz, 1H), 5.12 (bs, 1H), 4.67 (bs, 1H), 3.88 (s, 2H), 2.98 (bs, 2H), 2.72 (bs, 2H), 2.44-2.30 (m, 2H), 2.15 (s, 3H), 1.91 (bs, 4H), 1.69 (bs, 2H), 1.36 (bs, 4H).

Intermediate 33

Ethyl[4-(hydroxymethyl)phenoxy]acetate

A solution of 4-(hydroxymethyl)phenol (400 mg, 3.19 mmol) in CH$_3$CN (4 mL) was placed in a sealed tube, then potassium carbonate (550 mg, 3.98 mmol) and ethyl bromoacetate (0.365 mL, 3.23 mmol) were added and purged with argon. The reaction mixture was stirred at reflux (90° C.) for 20h. The cooled reaction mixture was filtered through sintered glass (pore no 4) and the solvent removed to obtain light-yellow oil. The crude was purified by column chromatography with nHexane and Et$_2$O as eluents (0% to 100%

B in 20 column volumes and 100% for 10 CV, 18 mL/min). The appropriate fractions were collected and the solvent removed to afford the title compound (446 mg, 62%) as colourless solid.

LRMS (m/z): 211 (M+1)$^+$

Intermediate 34 tert-butyl methyl(2-oxoethyl)carbamate

To an ice-cooled solution of tert-butyl 2-hydroxyethyl (methyl)carbamate (300 mg, 1.71 mmol)) in dry $CH_2Cl_2$ (8.5 mL) under argon was added portion wise Dess-Martin periodinane (762 mg, 1.8 mmol). Once finished the addition, the reaction mixture was stirred at room temperature for 3h. The mixture was poured into saturated solutions of $NaHCO_3$ (50 mL) and $Na_2S_2O_3$ (50 mL) and more $CH_2Cl_2$ (100 mL). It was well-stirred at room temperature for 30 minutes. The organic phase was separated and washed with sat. aq. $NaHCO_3$ (1×20 mL). It was dried over magnesium sulphate and concentrated to afford the title compound (370 mg, 98%) as colourless oil together with a yellow solid, which was used in the next step without further purification.

$^1$H NMR (300 MHz, cdcl3) δ 9.61 (s, 1H), 3.98 (d, J=33.9 Hz, 2H), 2.94 (t, J=10.8 Hz, 3H), 1.46 (dd, J=8.2, 6.3 Hz, 9H).

Intermediate 35 trans-4-[{2-[(tert-butoxycarbonyl)(methyl)amino] ethyl}(methyl)amino]cyclohexyl hydroxy(di-2-thienyl)acetate To a solution of tert-butyl methyl(2-oxoethyl)carbamate in DCE (3 mL) under argon was added trans-4-(methylamino)cyclohexyl hydroxy(di-2-thienyl)acetate (Intermediate 5; 150 mg, 0.43 mmol) and $NaBH(OAc)_3$ (136 mg, 0.64 mmol). The reaction mixture was stirred at room temperature under argon for 3h. The solvent was removed under reduced pressure and the residue poured into sat. aq. $NaHCO_3$ (20 mL). It was extracted with EtOAc (2×50 mL), the combined organic layers were dried over sodium sulphate and the solvent removed to afford 290 mg of brown oil. The sample was purified by column chromatography with $CH_2Cl_2$ and EtOH (95:5) as eluents (0% to 100%). The appropriate fractions were collected and the solvent removed to afford the title compound (203 mg, 92%) as brownish oil.

LRMS (m/z): 509 (M+1)$^+$

Intermediate 36 trans-4-{methyl[2-(methylamino)ethyl] amino}cyclohexyl hydroxy(di-2-thienyl)acetate To a solution of trans-4-[{2-[(tert-butoxycarbonyl) (methyl)amino]ethyl}(methyl)amino]-cyclohexyl hydroxy (di-2-thienyl)acetate (198 mg, 0.39 mmol) in THF (6.5 mL) under argon was added 1M aq. HCl (1.17 mL) and the mixture was stirred at RT for 18h. More 1M HCl (0.8 mL, 2 eq.) was added and the reaction mixture was stirred at 70° C. for 4 hours. The reaction mixture was basified with sat. aq. $NaHCO_3$ (20 mL). It was extracted with EtOAc (3×50 mL), the combined organic layers were dried over sodium sulphate and the solvent removed to afford brown oil. The crude material was injected into a C18 silica column. The gradient used was H2O and acetonitrile/MeOH (1:1). The appropriate fractions were collected and all the solvents evaporated under reduced pressure to afford the title compound (90 mg, 54%) as light-brown oil.

LRMS (m/z): 409 (M+1)$^+$

Intermediate 37 trans-4-[{2-[{[4-(hydroxymethyl)phenoxy]acetyl} (methyl)amino]ethyl}(methyl)amino]cyclohexyl hydroxy(di-2-thienyl)acetate trans-4-{methyl[2-(methylamino)ethyl] amino}cyclohexyl hydroxy(di-2-thienyl)acetate (Intermediate 36; 85 mg, 0.21 mmol) and ethyl[4-(hydroxymethyl) phenoxy]acetate (Intermediate 33; 65 mg, 0.31 mmol) were dissolved in EtOH (0.65 mL) and heated in a PLS at 75° C. for 48h. More Intermediate 33 (15 mg, 0.3 eq) and $MgSO_4$ (50 mg) were added and the reaction mixture was stirred at 75° C. for another 50 h. The sample was purified by column with $CHCl_3$ and EtOH as eluents (0% to 100% B). The appropriate fractions were collected and the solvent removed to afford crude of 18 mg of blue oil. It was repurified with $CH_2Cl_2$ and $CH_2Cl_2$/MeOH (9:1) as eluents (0% to 100% B). The appropriate fractions were collected and the solvent removed to give the title compound (10 mg; 7.6%) as a sticky solid.

LRMS (m/z): 573 (M+1)$^+$

Intermediate 38 trans-4-[{2-[[(4-formylphenoxy)acetyl](methyl) amino]ethyl}(methyl)amino]cyclohexyl hydroxy(di-2-thienyl)acetate Obtained as an oil (27 mg, 66%) from trans-4-[{2-[{[4-(hydroxymethyl)phenoxy]-acetyl}-(methyl)amino]ethyl} (methyl)amino]cyclohexyl hydroxy(di-2-thienyl)acetate (Intermediate 37; 40 mg, 0.07 mmol) and manganese oxide (61 mg, 0.7 mmol) following the experimental procedure as descried for Intermediate 31 and the crude obtained was used in the next step without further purification.

LRMS (m/z): 571 (M+1)$^+$

Intermediate 39 trans-4-[{2-[{[4-({[(2R)-2-{[tert-butyl(dimethyl) silyl]oxy}-2-(8-hydroxy-2-oxo-1,2-dihydroquinolin-5-yl)ethyl]amino}methyl)phenoxy]acetyl}(methyl) amino]ethyl}(methyl)amino]cyclohexyl hydroxy(di-2-thienyl)acetate Obtained as a yellow foam (81 mg, 66%) from trans-4-[{2-[[(4-formylphenoxy)-acetyl](methyl)amino]ethyl} (methyl)amino]cyclohexyl hydroxy(di-2-thienyl)acetate (Intermediate 38; 73 mg, 0.13 mmol), 5-((1 R)-2-amino-1-{[tert-butyl(dimethyl)-silyl]oxy}ethyl)-8-hydroxyquinolin-2(1H)-one acetate (prepared according to preparation 8 from US20060035931; 56 mg, 0.14 mmol), DIEA (29 µL, 0.17 mmol) and sodium triacetoxyborohydride (81 mg, 0.38 mmol) following the procedure as described for Intermediate 10 and the crude obtained was purified over silica gel eluting with Chloroform/Methanol (100/0 to 0/100).

LRMS (m/z): 890 (M+1)$^+$

Example 6 trans-4-[{2-[{[4-({[(2R)-2-hydroxy-2-(8-hydroxy-2-oxo-1,2-dihydroquinolin-5-yl)ethyl]amino}methyl)phenoxy]acetyl}(methyl)amino]ethyl}(methyl)amino]cyclohexyl hydroxy(di-2-thienyl)acetate dihydrofluoride Obtained as a white solid (90 mg, 72%) from trans-4-[{2-[{[4-({[(2R)-2-{[tert-butyl(dimethyl)silyl]oxy}-2-(8-hydroxy-2-oxo-1,2-dihydroquinolin-5-yl)ethyl]amino}methyl)phenoxy]acetyl}(methyl)amino]ethyl}(methyl)amino]cyclohexyl hydroxy(di-2-thienyl)acetate (Intermediate 39; 135 mg, 0.15 mmol) and triethylamine trihydrofluoride (97 µL, 0.60 mmol) following the experimental procedure as described for Example 1.

LRMS (m/z): 775 (M+1)$^+$ $^1$H NMR (300 MHz, dmso) δ 8.14 (d, J=10.0 Hz, 1H), 7.50 (d, J=5.0 Hz, 1H), 7.29 (d, J=8.1 Hz, 2H), 7.14-7.05 (m, 3H), 7.05-6.99 (m, 2H), 6.95 (d, J=8.1 Hz, 2H), 6.89 (d, J=8.5 Hz, 2H), 6.53 (d, J=9.8 Hz, 1H), 5.16 (s, 1H), 4.83 (d, J=20.7 Hz, 2H), 4.72 (s, 1H), 3.82 (bs, 2H), 2.86 (bs, 2H), 2.77 (s 3H), 2.50 (s, 3H), 2.23 (d, J=18.1 Hz, 2H), 1.94 (bs, 2H), 1.74 (bs, 2H), 1.39 (bs, 2H), 1.08 (bs, 4H).

Intermediate 40

3-[1-(2-{[tert-butyl(dimethyl)silyl]oxy}ethyl)-1H-indol-3-yl]propanoic acid

To a solution of 3-(1H-indol-3-yl)propanoic acid (5 g, 0.026 mol) in DMF (20 mL) was added at 0° C. sodium hydride (2.11 g, 0.088 mol), the mixture was stirred some minutes at 0° C. and (2-bromoethoxy)(tert-butyl)dimethylsilane (5.67 mL, 0.026 mol) was added. The reaction mixture was stirred overnight at room temperature. The crude mixture was poured into a sodium sulphate saturate solution and extracted with ethyl acetate. The solvent was removed under reduced pressure and the crude obtained was purified over silica gel eluting with hexane:ether (100/0 to 0/100) to obtain the title compound (4 g, 43%).

LRMS (m/z): 348 (M+1)$^+$

Intermediate 41

3-[1-(2-{[tert-butyl(dimethyl)silyl]oxy}ethyl)-1H-indol-3-yl]propan-1-ol

To a solution of lithium aluminium hydride (0.44 g, 0.011 mol) in diethyl ether (10 mL) was added dropwise at 0° C. solution of 3-[1-(2-{[tert-butyl(dimethyl)silyl]oxy}ethyl)-1H-indol-3-yl]propanoic acid (Intermediate 40; 2 g, 0.011 mol) in ethyl ether (10 mL). The reaction mixture was stirred at room temperature for 45 minutes. Saturated sodium bicarbonate was added into the mixture at 0° C. The organic phase was extracted and the solvent was removed under reduced pressure giving the title compound (3.2 g, 83%), which was used in the next step without further purification.

LRMS (m/z): 334 (M+1)$^+$

Intermediate 42

3-[1-(2-{[tert-butyl(dimethyl)silyl]oxy}ethyl)-1H-indol-3-yl]propyl methanesulfonate To a solution of 3-[1-(2-{[tert-butyl(dimethyl)silyl]oxy}ethyl)-1H-indol-3-yl]propan-1-ol (Intermediate 41; 3.2 g, 0.009 mol) in CH$_2$Cl$_2$ (25 mL) was added at −40° C. methanesulfonyl bromide (0.93 mL, 0.011 mol) and triethylamine (1.74 mL, 0.012 mol). The reaction mixture was stirred for 5 minutes. More CH$_2$Cl$_2$ was added into the mixture and the organic layer was washed with water. The solvent was removed under reduced pressure giving the title compound (3.5 g, 88%), which was used in the next step without further purification.

LRMS (m/z): 412 (M+1)$^+$

Intermediate 43

1-(2-{[tert-butyl(di methyl)silyl]oxy}ethyl)-3-(3-iodopropyl)-1H-indole

To a solution of 3-[1-(2-{[tert-butyl(dimethyl)silyl]oxy}ethyl)-1H-indol-3-yl]propyl methanesulfonate (Intermediate 42; 3.5 g, 8.5 mmol) in ketone (20 mL) was added sodium iodide (2.55 g, 17 mmol). The reaction mixture was stirred overnight at 50° C. The crude reaction was filtered and the solvent was removed under reduced pressure. The crude obtained was purified over silica gel eluting with hexane:ether (100/0 to 0/100) to obtain the title compound (2.7 g, 71%).

LRMS (m/z): 444 (M+1)$^+$

Intermediate 44 trans-4-[{3-[1-(2-{[tert-butyl(dimethyl)silyl]oxy}ethyl)-1H-indol-3-yl]propyl}(methyl)amino]cyclohexyl hydroxy(di-2-thienyl)acetate Obtained as an oil (750 mg, 70%) from 1-(2-{[tert-butyl(dimethyl)silyl]oxy}ethyl)-3-(3-iodopropyl)-1H-indole (Intermediate 43; 630 mg, 1.42 mmol), trans-4-(methylamino)cyclohexyl hydroxy(di-2-thienyl)acetate (Intermediate 5; 450 mg, 1.28 mmol) and Et$_3$N (0.2 mL, 1.43 mmol) following the experimental procedure as described for Intermediate 9 and the crude obtained was used in the next step without further purification.

LRMS (m/z): 668 (M+1)+

Intermediate 45 trans-4-[{3-[1-(2-hydroxyethyl)-1H-indol-3-yl]propyl}(methyl)amino]cyclohexyl hydroxy(di-2-thienyl)acetate To a solution of trans-4-[{3-[1-(2-{[tert-butyl(dimethyl)silyl]oxy}ethyl)-1H-indol-3-yl]propyl}(methyl)amino]cyclohexyl hydroxy(di-2-thienyl)acetate (Intermediate 44; 19 g, 2.85 mmol) in THF (20 mL) was added hydrochloric acid (8.55 mL, 1M). The reaction mixture was stirred overnight at room temperature. Ethyl Acetate was poured into the mixture and the organic layer was washed with water and sodium bicarbonate, dried, filtered and the solvent was removed under reduced pressure. The crude obtained was purified over silica gel eluting with chloroform:ethanol (100/0 to 0/100) to obtain the title compound (940 mg, 59%).

LRMS (m/z): 553 (M+1)$^+$

Intermediate 46 trans-4-(methyl{3-[1-(2-{[(4-methylphenyl)sulfonyl]oxy}ethyl)-1H-indol-3-yl]propyl}amino)cyclohexyl hydroxy(di-2-thienyl)acetate To a solution of trans-4-[{3-[1-(2-hydroxyethyl)-1H-indol-3-yl]propyl}(methyl)amino]cyclohexyl hydroxy(di-2- thienyl)acetate (Intermediate 45; 140 mg, 0.25 mmol) in CH$_2$Cl$_2$ (10 mL) was added triethylamine (46 μL, 0.33 mmol) and dimethylaminopyridine (31 mg, 0.25 mmol). The reaction mixture was stirred overnight at room temperature. The solvent was removed under reduced pressure and the crude obtained was purified over silica gel eluting with ethyl ether to obtain the title compound (110 mg, 61%).

LRMS (m/z): 707 (M+1)$^+$

Intermediate 47 trans-4-[{3-[1-(2-{[(2R)-2-{[tert-butyl(di methyl) silyl]oxy}-2-(8-hydroxy-2-oxo-1,2-dihydroquinolin-5-yl)ethyl]amino}ethyl)-1H-indol-3-yl]propyl} (methyl)amino]cyclohexyl hydroxy(di-2-thienyl) acetate To a solution of trans-4-(methyl{3-[1-(2-{[(4-methylphenyl)sulfonyl]oxy}ethyl)-1H-indol-3-yl]propyl}amino)cyclohexyl hydroxy(di-2-thienyl)acetate (Intermediate 46; 310 mg, 0.44 mmol) in N,N-dimethylacetamide anhydrous (1.5 mL) was added 5-((1R)-2-amino-1-{[tert-butyl(dimethyl)silyl]oxy}ethyl)-8-hydroxyquinolin-2(1H)-one free base (prepared according to preparation 8 from US20060035931; 146 mg, 0.44 mmol) and sodium bicarbonate (73 mg, 0.87 mmol). The reaction mixture was stirred overnight at 70° C. Water was poured into the mixture and the precipitate was filtered. The crude was purified over silica gel eluting with chloroform/ethanol to obtain the title compound as a solid (20 mg, 5%).

LRMS (m/z): 870 (M+1)+

Example 7 trans-4-[{3-[1-(2-{[(2R)-2-hydroxy-2-(8-hydroxy-2-oxo-1,2-dihydroquinolin-5-yl)ethyl]amino}ethyl)-1H-indol-3-yl]propyl}(methyl)amino]cyclohexyl hydroxy(di-2-thienyl)acetate dihydrofluoride Obtained as a white solid (11 mg, 63%) from trans-4-[{3-[1-(2-{[(2R)-2-{[tert-butyl(dimethyl)silyl]oxy}-2-(8-hydroxy-2-oxo-1,2-dihydroquinolin-5-yl)ethyl]amino}ethyl)-1H-indol-3-yl]propyl}(methyl)amino]cyclohexyl hydroxy (di-2-thienyl)acetate (Intermediate 47; 20 mg, 0.02 mmol) and triethylamine trihydrofluoride (15 μL, 0.09 mmol) following the experimental procedure as described for Example 1.

LRMS (m/z): 755 (M+1)+

$^1$H NMR (600 MHz, dmso) δ 10.46 (s, 1H), 8.26 (bs, 2H), 7.59-7.38 (m, 4H), 7.31 (bs, 2H), 7.19-6.84 (m, 6H), 6.49 (t, J=17.6 Hz, 1H), 5.34 (s, 1H), 4.71 (bs, 1H), 4.45 (bs, 2H), 3.24 (bs, 2H), 2.98 (dd, J=57.9, 20.5 Hz, 5H), 2.65 (d, J=35.8 Hz, 3H), 2.10-1.80 (m, 4H), 1.53 (bs, 4H), 1.46-1.33 (m, 4H).

Intermediate 48 trans-4-[{2-[(tert-butoxycarbonyl)amino]ethyl} (methyl)amino]cyclohexyl hydroxy(di-2-thienyl) acetate Obtained as a solid (281 mg, 40%) from tert-butyl 2-bromoethylcarbamate (385 mg, 1.72 mmol), trans-4-(methylamino)cyclohexyl hydroxy(di-2-thienyl)acetate (Intermediate 5; 500 mg, 1.42 mmol) and Et$_3$N (0.3 mL, 2.15 mmol) following the experimental procedure as described for Intermediate 9 and the crude obtained was purified over silica gel eluting with CH$_2$Cl$_2$:EtOH.

LRMS (m/z): 495 (M+1)$^+$

Intermediate 49 trans-4-[(2-aminoethyl)(methyl)amino]cyclohexyl hydroxy(di-2-thienyl)acetate

To a solution of trans-4-[{2-[(tert-butoxycarbonyl)amino] ethyl}(methyl)amino]cyclohexyl hydroxy(di-2-thienyl)acetate (Intermediate 48; 281 mg, 0.57 mmol) in dioxane (3.5 mL) was added hydrochloric acid (4M in dioxane, 1.5 mL). The reaction mixture was stirred overnight at room temperature. The crude reaction was washed with sodium bicarbonate and the crude was extracted with THF. The solvent was removed under reduced pressure giving the title compound (266 mg, 95%), which was used in the next step without further purification.

LRMS (m/z): 395 (M+1)$^+$

Intermediate 50

[4-(hydroxymethyl)phenoxy]acetic acid

To a solution of trans-4-[(2-aminoethyl)(methyl)amino] cyclohexyl hydroxy(di-2-thienyl)acetate (312 mg, 1.48 mmol) in THF (12 mL) and water (8 mL) was added a solution of lithium hydroxide (109 mg, 4.46 mmol) in water (4 mL). It was stirred at room temperature for 2h. The THF was removed under vacuum and the aqueous solution was acidified with 5N HCl until pH=2. It was extracted with EtOAc (3×20 mL). The combined organic layers were washed with brine (1×20 mL), dried over sodium sulphate and the solvent evaporated to afford the title compound (248 mg, 89%) as a white solid, which was used in the next step without further purification.

LRMS (m/z): 183 (M+1)$^+$

Intermediate 51 trans-4-[[2-({[4-(hydroxymethyl)phenoxy] acetyl}amino)ethyl](methyl)amino]cyclohexyl hydroxy(di-2-thienyl)acetate To a solution of [4-(hydroxymethyl)phenoxy]acetic acid (Intermediate 50; 99 mg, 0.54 mmol) in DMF (4.5 mL) was added trans-4-[(2-aminoethyl)(methyl)amino]cyclohexyl hydroxy(di-2-thienyl)acetate (Intermediate 49; 215 mg, 0.54 mmol), HBTU (316 mg, 0.83 mmol) and DIEA (0.38 mL, 2.19 mmol). The reaction mixture was stirred overnight at room temperature. The solvent was removed and the crude was partitioned between ethyl acetate and sodium bicarbonate 4%. The organic layer was washed with water, brine, dried, filtered and the solvent was removed to give crude, which was purified over silica gel eluting with CHCl$_3$:Hexane to give the title compound (152 mg, 47%)

LRMS (m/z): 559 (M+1)$^+$

Intermediate 52 trans-4-[(2-{[(4-formylphenoxy)acetyl]amino}ethyl) (methyl)amino]cyclohexyl hydroxy(di-2-thienyl) acetate Obtained as a solid (130 mg, 85%) from trans-4-[[2-({ [4-(hydroxymethyl)phenoxy]acetyl}amino)ethyl](methyl)

amino]cyclohexyl hydroxy(di-2-thienyl)acetate (Intermediate 51; 152 mg, 0.27 mmol) and manganese oxide (236 mg, 2.71 mmol) following the experimental procedure as described for Intermediate 31 and the crude obtained was used in the next step without further purification.
LRMS (m/z): 557 (M+1)+

Intermediate 53 trans-4-[[2-({[4-({[(2R)-2-{[tert-butyl (dimethyl) silyl]oxy}-2-(8-hydroxy-2-oxo-1,2-dihydroquinolin-5-yl)ethyl]amino}methyl)phenoxy]acetyl}amino) ethyl](methyl)amino]cyclohexyl hydroxy(di-2-thienyl)acetate Obtained as a yellow foam (176 mg, 86%) from trans-4-[(2-{[(4-formylphenoxy)acetyl]amino}ethyl)(methyl) amino]cyclohexyl hydroxy(di-2-thienyl)-acetate (Intermediate 52; 130 mg, 0.23 mmol), 5-((1 R)-2-amino-1-{[tert-butyl (dimethyl)-silyl]oxy}ethyl)-8-hydroxyquinolin-2(1H)-one acetate (prepared according to preparation 8 from US20060035931; 99 mg, 0.25 mmol), DIEA (53 µL, 0.3 mmol) and sodium triacetoxyborohydride (148 mg, 0.7 mmol) following the procedure as described for Intermediate 10 and the crude obtained was purified over silica gel eluting with Chloroform/Methanol (100/0 to 0/100).
LRMS (m/z): 876 (M+1)+

Example 8 trans-4-[[2-({[4-({[(2R)-2-hydroxy-2-(8-hydroxy-2-oxo-1,2-dihydroquinolin-5-yl)ethyl]amino}methyl) phenoxy]acetyl}amino)ethyl](methyl)amino]cyclohexyl hydroxy(di-2-thienyl)acetate dihydrofluoride Obtained as a white solid (89 mg, 57%) from trans-4-[[2-({[4-({[(2R)-2-{[tert-butyl(dimethyl)silyl]oxy}-2-(8-hydroxy-2-oxo-1,2-dihydroquinolin-5-yl)ethyl]amino}-methyl)phenoxy]acetyl}amino)ethyl](methyl)amino] cyclohexyl hydroxy(di-2-thienyl)-acetate (Intermediate 53; 176 mg, 0.2 mmol) and triethylamine trihydrofluoride (131 µL, 0.8 mmol) following the experimental procedure as described for Example 1.
LRMS (m/z): 761 (M+1)+
$^1$H NMR (300 MHz, dmso) δ 8.15 (d, J=9.9 Hz, 1H), 7.87 (bs, 1H), 7.50 (d, J=5.1 Hz, 1H), 7.31 (d, J=8.3 Hz, 2H), 7.14-7.06 (m, 4H), 7.05-6.99 (m, 2H), 6.94 (dd, J=8.2, 4.0 Hz, 2H), 6.53 (d, J=9.8 Hz, 1H), 5.14 (bs, 1H), 4.71 (bs, 1H), 4.48 (bs, 2H), 3.79 (bs, 2H), 2.73 (bs, 2H), 2.48 (s, 3H), 2.43-2.29 (m, 2H), 2.19 (bs, 2H), 1.93 (s, 3H), 1.37 (bs, 4H), 1.08 (d, J=6.1 Hz, 2H).

Intermediate 54

5-chloro-4-cyano-2-methoxybenzoic acid

To a solution of 4-amino-5-chloro-2-methoxybenzoic acid (4 g, 0.019 mol) in water (60 mL) was added hydrochloric acid (35%, 0.63 mL) and the mixture was stirred vigorously and cooled to 5° C. Then a solution of sodium nitrite (1.92 g, 0.027 mol) in water (6 mL) was added dropwise. The mixture was stirred for some minutes and then a previously formed solution of copper cyanide (2.32 g, 0.026 mol) and sodium cyanide (3.65 g, 0.074 mol) in water (20 mL) was added dropwise maintaining a low temperature. Once the addition was finished the reaction mixture was stirred 1 hour at room temperature. The pH of the aqueous phase was adjusted to 3 and ethyl acetate was added into the mixture and the organic layer was washed with water, dried, filtered and the solvent was removed under reduced pressure giving the title compound (2.93 g, 62%).
LRMS (m/z): 212 (M+1)+

Intermediate 55

2-chloro-4-(hydroxymethyl)-5-methoxybenzonitrile

To a solution of 5-chloro-4-cyano-2-methoxybenzoic acid (Intermediate 54; 2.93 g, 0.013 mol) in anh THF (50 mL) was added portion wise at 0° C. borane-methyl sulphide complex (2M in THF, 2.63 mL, 0.027 mol). The reaction mixture was stirred 3 hours at room temperature. 5.5 mL of water was added into the mixture and with ethyl the crude was extracted. The solvent was removed under reduced pressure and the crude obtained was purified over silica gel eluting with Chloroform/Methanol (100/0 to 0/100) to give the title compound as a solid (2.13 g, 77%)
LRMS (m/z): 198 (M+1)+

Intermediate 56

2-chloro-5-methoxy-4-[(tetrahydro-2H-pyran-2-yloxy)methyl]benzonitrile

To a solution of 2-chloro-4-(hydroxymethyl)-5-methoxybenzonitrile (Intermediate 55; 800 mg, 4.05 mmol) in dichloromethane/THF (28 mL/12 mL) was added under nitrogen atmosphere 3,4-dihydro-2H-pyran (0.444 mL, 4.86 mmol) and pyridinium p-toluene sulfonate (100 mg, 0.4 mmol). The reaction mixture was stirred for 48 hours at room temperature. The solvent was removed under reduced pressure and the crude obtained was partitioned between ether and water. The organic layer was dried, filtered and the solvent removed giving a crude which was purified over silica gel eluting with Chloroform/Hexane (100/0 to 0/100) to give the title compound an oil (1.1 g, 98%)
LRMS (m/z): 282 (M+1)+

Intermediate 57

2-chloro-N-hydroxy-5-methoxy-4-[(tetrahydro-2H-pyran-2-yloxy)methyl]benzenecarboximidamide To a solution of Hydroxylamine hydrochloride (1.28 g, 0.018 mol) in ethanol (10 mL) was added Et$_3$N (2.74 mL, 0.019 mol). The reaction mixture was stirred at 0° C. and then a solution of 2-chloro-5-methoxy-4-[(tetrahydro-2H-pyran-2-yloxy)methyl]benzonitrile (Intermediate 56; 1.1 g, 4.11 mmol) in ethanol (20 mL) was added. The mixture was stirred for 5 hours at 65° C. The solvent was removed under reduced pressure and the crude obtained was purified over silica gel eluting with Chloroform/Hexane (100/0 to 0/100) to give the title compound oil (796 mg, 60%)
LRMS (m/z): 315 (M+1)+

Intermediate 58

5-(3-bromopropyl)-3-{2-chloro-5-methoxy-4-[(tetrahydro-2H-pyran-2-yloxy)methyl]phenyl}-1,2,4-oxadiazole To a solution of 2-chloro-N-hydroxy-5-methoxy-4-[(tetrahydro-2H-pyran-2-yloxy)methyl]benzenecarboximidamide (Intermediate 57; 796 mg, 2.53 mmol) and DIEA (551

μL, 3.15 mmol) in dichloromethane (18 mL) was added dropwise 4-bromobutanoyl chloride (324 μL, 2.8 mmol) in dichloromethane (3 mL). The reaction mixture was stirred 20 hours at room temperature. The mixture was diluted with dichloromethane and the organic layer was washed with sodium bicarbonate and brine. The solvent was removed under reduced pressure giving an oil, which was used to cyclize without further manipulation. The crude obtained was dissolved in toluene and refluxed for 2 hours. The solvent was removed under reduced pressure and the crude obtained was purified over silica gel eluting with Ethyl acetate/Hexane (100/0 to 0/100) to give the title compound an oil (487 mg, 37%)

LRMS (m/z): 446 (M+1)$^+$

Intermediate 59 trans-4-[[3-(3-{2-chloro-5-methoxy-4-[(tetrahydro-2H-pyran-2-yloxy)methyl]phenyl}-1,2,4-oxadiazol-5-yl)propyl](methyl)amino]cyclohexyl hydroxy(di-2-thienyl)acetate Obtained as an oil (585 mg, 84%) from 5-(3-bromopropyl)-3-{2-chloro-5-methoxy-4-[(tetrahydro-2H-pyran-2-yloxy)methyl]phenyl}-1,2,4-oxadiazole (Intermediate 58; 486 mg, 0.95 mmol), trans-4-(methylamino)cyclohexyl hydroxy(di-2-thienyl)acetate (Intermediate 5; 386 mg, 1.1 mmol) and DIEA (0.38 mL, 2.18 mmol) following the experimental procedure as described for Intermediate 9 and the crude obtained was purified over silica gel eluting with $CH_2Cl_2$:EtOH.

LRMS (m/z): 717 (M+1)$^+$

Intermediate 60 trans-4-[(3-{3-[2-chloro-4-(hydroxymethyl)-5-methoxyphenyl]-1,2,4-oxadiazol-5-yl}propyl)(methyl)amino]cyclohexyl hydroxy(di-2-thienyl)acetate Obtained as a yellow oil (378 mg, 74%) from trans-4-[[3-(3-{2-chloro-5-methoxy-4-[(tetrahydro-2H-pyran-2-yloxy)methyl]phenyl}-1,2,4-oxadiazol-5-yl)propyl](methyl)-amino]cyclohexyl hydroxy(di-2-thienyl)acetate (Intermediate 59; 579 mg, 0.81 mmol) and hydrochloric acid (1M, 2.43 mL) following the experimental procedure as described for Intermediate 30 and the crude obtained was purified over silica gel eluting with $CHCl_3$:Hexane.

LRMS (m/z): 633 (M+1)$^+$

Intermediate 61 trans-4-[{3-[3-(2-chloro-4-formyl-5-methoxyphenyl)-1,2,4-oxadiazol-5-yl]propyl}(methyl)amino] cyclohexyl hydroxy(di-2-thienyl)acetate Obtained as an oil (326 mg, 78%) from trans-4-[(3-{3-[2-chloro-4-(hydroxymethyl)-5-methoxyphenyl]-1,2,4-oxadiazol-5-yl}propyl)(methyl)amino]cyclohexyl hydroxy(di-2-thienyl)acetate (Intermediate 60; 377 mg, 0.6 mmol) and manganese oxide (570 mg, 6.56 mmol) following the experimental procedure as described for Intermediate 31 and the crude obtained was used in the next step without further purification.

LRMS (m/z): 631 (M+1)$^+$

Intermediate 62 trans-4-[(3-{3-[4-({[(2R)-2-{[tert-butyl(di methyl)silyl]oxy}-2-(8-hydroxy-2-oxo-1,2-dihydroquinolin-5-yl)ethyl]amino}methyl)-2-chloro-5-methoxyphenyl]-1,2,4-oxadiazol-5-yl}propyl)(methyl)amino] cyclohexyl hydroxy(di-2-thienyl)acetate Obtained as a yellow foam (373 mg, 76%) from trans-4-[{3-[3-(2-chloro-4-formyl-5-methoxyphenyl)-1,2,4-oxadiazol-5-yl]propyl}(methyl)amino]cyclohexyl hydroxy(di-2-thienyl)acetate (Intermediate 61; 320 mg, 0.51 mmol), 5-((1 R)-2-amino-1-{[tert-butyl(dimethyl)-silyl]oxy}ethyl)-8-hydroxyquinolin-2(1H)-one acetate (prepared according to preparation 8 from US20060035931; 220 mg, 0.56 mmol), DIEA (115 μL, 0.66 mmol) and sodium triacetoxyborohydride (350 mg, 1.65 mmol) following the procedure as described for Intermediate 10 and the crude obtained was purified over silica gel eluting with Chloroform/Methanol (100/0 to 0/100).

LRMS (m/z): 949 (M+1)$^+$

Example 9 trans-4-[(3-{3-[2-chloro-4-({[(2R)-2-hydroxy-2-(8-hydroxy-2-oxo-1,2-dihydroquinolin-5-yl)ethyl] amino}methyl)-5-methoxyphenyl]-1,2,4-oxadiazol-5-yl}propyl)(methyl)amino]cyclohexyl hydroxy(di-2-thienyl)acetate dihydrofluoride Obtained as a white solid (279 mg, 82%) from trans-4-[(3-{3-[4-({[(2R)-2-{[tert-butyl(dimethyl)silyl]oxy}-2-(8-hydroxy-2-oxo-1,2-dihydroquinolin-5-yl)ethyl]amino}-methyl)-2-chloro-5-methoxyphenyl]-1,2,4-oxadiazol-5-yl}propyl)(methyl)-amino]-cyclohexyl hydroxy(di-2-thienyl)acetate (Intermediate 62; 367 mg, 0.39 mmol) and triethylamine trihydrofluoride (252 μL, 1.55 mmol) following the experimental procedure as described for Example 1.

LRMS (m/z): 835 (M+1)$^+$ $^1$H NMR (300 MHz, dmso) δ 8.15 (d, J=10.0 Hz, 1H), 7.54 (s, 1H), 7.46 (dd, J=5.1, 1.3 Hz, 1H), 7.36 (s, 1H), 7.25 (s, 1H), 7.11-7.01 (m, 3H), 7.00-6.88 (m, 3H), 6.48 (d, J=9.9 Hz, 1H), 5.12-5.03 (m, 1H), 4.67 (bs, 1H), 3.80 (s, 3H), 3.01 (t, J=7.2 Hz, 2H), 2.82-2.63 (m, 2H), 2.41 (bs, 1H), 2.16 (s, 3H), 1.98-1.83 (m, 5H), 1.70 (s, 2H), 1.35 (s, 4H), 1.04 (d, J=6.1 Hz, 3H).

Intermediate 63 methyl 5-chloro-4-hydroxy-2-methoxybenzoate

To solution of 4-amino-5-chloro-2-methoxybenzoic acid (10 g, 0.048 mol) in water (50 mL) was added $HBF_4$ (48% in water, 16.2 mL, 0.12 mol) and acetyl chloride (2.24 mL, 0.031 mol) and the mixture was stirred for 1 hour at room temperature. The mixture was cooled to 0° C. to add dropwise sodium nitrite (3.76 g, 0.054 mol) in water (30 mL). The reaction was allowed to stirrer at 0° C. for 30 minutes. Then the solid was filtered and it was treated with Acid Acetic (500 mL). The mixture was heated at 100° C. for 1 hour. The mixture was cooled and it was stand without further manipulation overnight. The solvent was removed under reduced pressure and the crude obtained was partitioned between Ethyl acetate and Brine. The organic layer was dried, filtered and the solvent was removed under reduced pressure. The crude was treated with sodium hydroxide (150 mL) for 90 minutes at room temperature and overnight at 45° C. The crude was extracted with dichloromethane and purified over silica gel eluting with Dichloromethane/Ethanol (100/0 to 0/100) to give the title compound as a foam (1.1 g, 10%)
LRMS (m/z): 217 (M+1)+

Intermediate 64

2-chloro-4-(hydroxymethyl)-5-methoxyphenol

To a solution of methyl 5-chloro-4-hydroxy-2-methoxybenzoate (Intermediate 63; 1.1 g, 5.08 mmol) in THF (30 mL) was added dropwise at 0° C. lithium aluminium hydride (1M in THF, 9.65 mL). The reaction mixture was stirred 10 minutes at 0° C., 1 hour at room temperature and 30 minutes at 65° C. The mixture was cooled at 0° C. and a saturated solution of L-Tartrate (100 mL) was added cautiously. Then Ethyl acetate was added and the mixture was stirred for 1 hour at room temperature. The organic layer was separated, dried, filtered and the solvent was removed under reduced pressure to give a crude, which was purified over silica gel eluting with Chloroform/Ethanol (100/0 to 0/100) to give the title compound as a foam (460 mg, 450%)
LRMS (m/z): 189 (M+1)+

Intermediate 65

Ethyl[2-chloro-4-(hydroxymethyl)-5-methoxyphenoxy]acetate

To a solution of 2-chloro-4-(hydroxymethyl)-5-methoxyphenol (Intermediate 64; 459 mg, 2.43 mmol) in acetonitrile (5 mL) was added ethyl bromoacetate (0.26 mL, 2.43 mmol) and potassium carbonate (420 mg, 3.04 mmol) in a sealed tub. The mixture was stirred 2 hours at 90° C. The solid was filtrated, washed with acetonitrile and the solvent of the filtrate was removed under reduced pressure giving the title compound as a brown oil (640 mg, 85%), which was used in the next step without further purification.
LRMS (m/z): 275 (M+1)+

Intermediate 66

[2-chloro-4-(hydroxymethyl)-5-methoxyphenoxy] acetic acid

To a solution of ethyl[2-chloro-4-(hydroxymethyl)-5-methoxyphenoxy]acetate (Intermediate 65; 640 mg, 2.33 mmol) in THF (20 mL) was added water (20 mL) and lithium hydroxide (391 mg, 9.32 mmol). The reaction mixture was stirred for 1 hour at room temperature. The solvent was removed under reduced pressure and the aqueous phase was acidified until acid pH and then extracted with ethyl acetate. The organic layer was washed with brine, dried, filtered and the solvent was removed under reduced pressure to give the title compound as a red solid (550 mg, 95%), which was used in the next step without further purification.
LRMS (m/z): 247 (M+1)+

Intermediate 67 trans-4-[{2-[{[2-chloro-4-(hydroxymethyl)-5-methoxyphenoxy]acetyl}(methyl)amino]ethyl}(methyl)amino]cyclohexyl hydroxy(di-2-thienyl)acetate Obtained the title compound (400 mg, 64%) from [2-chloro-4-(hydroxymethyl)-5-methoxyphenoxy]acetic acid (Intermediate 66; 230 mg, 0.93 mmol), trans-4-{methyl [2-(methylamino)ethyl]amino}cyclohexyl hydroxy(di-2-thienyl)acetate (Intermediate 36; 376 mg, 0.92 mmol), HBTU (350 mg, 0.92 mmol) and DIEA (0.64 mL, 3.69 mmol) following the experimental procedure as described for Intermediate 51 and the crude obtained was purified over silica gel eluting with Chloroform/Hexane (100/0 to 0/100).
LRMS (m/z): 638 (M+1)+

Intermediate 68 trans-4-[{2-[[(2-chloro-4-formyl-5-methoxyphenoxy)acetyl](methyl)amino]ethyl}(methyl)amino] cyclohexyl hydroxy(di-2-thienyl)acetate Obtained as an oil (390 mg, 90%) from trans-4-[{2-[{[2-chloro-4-(hydroxymethyl)-5-methoxyphenoxy]acetyl} (methyl)amino]ethyl}(methyl)amino]cyclohexyl hydroxy (di-2-thienyl)acetate (Intermediate 67; 400 mg, 0.63 mmol) and manganese oxide (545 mg, 6.27 mmol) following the experimental procedure as described for Intermediate 31 and the crude obtained was used in the next step without further purification.
LRMS (m/z): 636 (M+1)+

Intermediate 69 trans-4-[{2-[{[4-({[(2R)-2-{[tert-butyl(dimethyl) silyl]oxy}-2-(8-hydroxy-2-oxo-1,2-dihydroquinolin-5-yl)ethyl]amino}methyl)-2-chloro-5-methoxyphenoxy]acetyl}(methyl)amino]ethyl}(methyl)amino] cyclohexyl hydroxy(di-2-thienyl)acetate Obtained as a foam (306 mg, 52%) from trans-4-[{2-[[(2-chloro-4-formyl-5-methoxyphenoxy)acetyl](methyl)amino] ethyl}(methyl)amino]cyclohexyl hydroxy(di-2-thienyl)acetate (Intermediate 68; 390 mg, 0.61 mmol), 5-((1 R)-2-amino-1-{[tert-butyl(dimethyl)-silyl]oxy}ethyl)-8-hydroxyquinolin-2(1H)-one acetate (prepared according to preparation 8 from US20060035931; 226 mg, 0.68 mmol), DIEA (139 μL, 0.8 mmol) and sodium triacetoxyborohydride (390 mg, 1.84 mmol) following the procedure as described for Intermediate 10 and the crude obtained was purified over silica gel eluting with Chloroform/Methanol (100/0 to 0/100).
LRMS (m/z): 954 (M+1)+

Example 10 trans-4-[{2-[{[2-chloro-4-({[(2R)-2-hydroxy-2-(8-hydroxy-2-oxo-1,2-dihydroquinolin-5-yl)ethyl] amino}methyl)-5-methoxyphenoxy]acetyl}(methyl) amino]ethyl}(methyl)amino]cyclohexyl hydroxy(di-2-thienyl)acetate dihydrofluoride Obtained as a white solid (170 mg, 64%) from trans-4-[{2-[{[4-({[(2R)-2-{[tert-butyl(dimethyl)silyl]oxy}-2-(8-hydroxy-2-oxo-1,2-dihydroquinolin-5-yl)ethyl] amino}methyl)-2-chloro-5-methoxyphenoxy]acetyl}-(methyl)amino]ethyl}-(methyl)-amino]-cyclohexyl hydroxy (di-2-thienyl)acetate (Intermediate 69; 300 mg, 0.31 mmol) and triethylamine trihydrofluoride (205 μL, 1.26 mmol) following the experimental procedure as described for Example 1.
LRMS (m/z): 840 (M+1)+
$^1$H NMR (300 MHz, dmso) δ 8.12 (d, J=9.8 Hz, 1H), 7.46 (d, J=5.1 Hz, 1H), 7.30 (d, J=3.0 Hz, 1H), 7.26 (s, 1H), 7.11-7.01 (m, 3H), 7.01-6.86 (m, 3H), 6.63 (d, J=4.4 Hz, 1H), 6.49 (d, J=9.6 Hz, 1H), 5.08 (s, 1H), 4.95 (d, J=8.6 Hz, 2H), 3.73 (d, J=2.7 Hz, 3H), 3.69 (bs, 2H), 3.03 (s, 2H), 2.85 (bs, 2H), 2.69 (s, 3H), 2.45 (bs, 2H), 2.41-2.29 (m, 2H), 1.88 (s, 3H), 1.35-1.3 (m, 4H), 1.25-1.02 (m, 4H).

Intermediate 70

2-oxo-2,3-dihydro-1,3-benzothiazole-6-carbaldehyde

Obtained as a white solid (240 mg of 97% purity by HPLC, 99% yield) from 6-bromo-2-oxo-2,3-dihydro-1,3-benzothiazole (302 mg, 1.31 mmol), methylmagnesium bromide (0.48 mL of a 3M solution in Et$_2$O, 1.44 mmol), tert-butyllithium (3.0 mL of a 1.7 M solution in Hexanes, 5.10 mmol) and DMF (0.6 mL, 7.7 mmol) following the procedure described in Step 2 of Example 16 from patent WO02/50070.
LRMS (m/z): 180 (M+1)$^+$.

Intermediate 71

3-(3-hydroxypropyl)-2-oxo-2,3-dihydro-1,3-benzothiazole-6-carbaldehyde 2-oxo-2,3-dihydro-1,3-benzothiazole-6-carbaldehyde (120 mg, 0.67 mmol), 3-bromopropan-1-ol (85 µL, 0.94 mmol), potassium carbonate (278 mg, 2.01 mmol) and potassium iodide (55 mg, 0.33 mmol) were suspended in acetonitrile (2 mL) and the whole mixture was heated at 65° C. for 48h. Then, the solids were filtered off and washed with acetonitrile and the resulting filtrate was evaporated to dryness to afford the title compound as a solid (204 mg of 77% purity by HPLC, 99% yield) which was used without further purification.
LRMS (m/z): 238 (M+1)$^+$.

Intermediate 72

3-(6-formyl-2-oxo-1,3-benzothiazol-3(2H)-yl)propyl methanesulfonate

To a solution of 3-(3-hydroxypropyl)-2-oxo-2,3-dihydro-1,3-benzothiazole-6-carbaldehyde (Intermediate 71, 158 mg, 0.67 mmol) in CH$_2$Cl$_2$ (5 mL) was added Et$_3$N (0.11 mL, 0.80 mmol) and the mixture was cooled to 0° C. To this solution, methanesulfonyl chloride was added dropwise (57 µL, 0.74 mmol) and the mixture was maintained at 0° C. for 90 min. CH$_2$Cl$_2$ and 4% aqueous sodium bicarbonate solution (10 mL) were added to the reaction mixture and stirred for 10 min. The two layers were separated and the organic phase was washed with water and brine, dried over anhydrous sodium sulphate, filtered and concentrated under reduced pressure to give the title compound as a colourless oil (243 mg, 99% yield) which was used without further purification.
LRMS (m/z): 316 (M+1)$^+$.

Intermediate 73 trans-4-[[3-(6-formyl-2-oxo-1,3-benzothiazol-3(2H)-yl)propyl](methyl)amino]cyclohexyl hydroxy(di-2-thienyl)acetate To a solution of 3-(6-formyl-2-oxo-1,3-benzothiazol-3 (2H)-yl)propyl methanesulfonate (Intermediate 72, 210 mg, 0.67 mmol) in DMF (2 mL) was added trans-4-(methylamino)cyclohexyl hydroxy(di-2-thienyl)acetate (Intermediate 5, 234 mg, 0.67 mmol), sodium iodide (250 mg, 1.67 mmol) and DIEA (174 µL, 1.00 mmol) and the mixture was stirred at 60° C. for 3 hours. The reaction mixture was evaporated to dryness, the solid residue was re-suspended in a CH$_2$Cl$_2$/Hexanes mixture (20 mL of a 1/1 mixture) and the suspension was filtered through Celite®. The solvent was removed under reduced pressure and the resulting brownish residue was purified by column chromatography over silica gel eluting with a mixture of CH$_2$Cl$_2$/EtOH (gradient from 0 to 10% of EtOH) to provide the title compound as a yellow oil (231 mg, 55% yield (90% purity from HPLC)).
LRMS (m/z): 571 (M+1)$^+$.

Intermediate 74 trans-4-[{3-[6-({[(2R)-2-{[tert-butyl(di methyl)silyl] oxy}-2-(8-hydroxy-2-oxo-1,2-dihydroquinolin-5-yl) ethyl]amino}methyl)-2-oxo-1,3-benzothiazol-3(2H)-yl]propyl}(methyl)amino]cyclohexyl hydroxy(di-2-thienyl)acetate Obtained as a pale yellow solid (2104 mg, 59% yield) from trans-4-[[3-(6-formyl-2-oxo-1,3-benzothiazol-3(2H)-yl)propyl](methyl)amino]cyclohexyl hydroxy(di-2-thienyl) acetate (Intermediate 73, 230 mg, 0.40 mmol), 5-((1 R)-2-amino-1-{[tert-butyl(dimethyl)-silyl]oxy}ethyl)-8-hydroxyquinolin-2(1H)-one acetate (prepared according to preparation 8 from US20060035931, 148 mg, 0.44 mmol) and sodium triacetoxyborohydride (270 mg, 1.27 mmol) following the experimental procedure described for the synthesis of Intermediate 10. The crude obtained was purified by column chromatography over silica gel, eluting with a mixture of CHCl$_3$:EtOH (from 0 to 50% of EtOH).
LRMS (m/z): 890 (M+1)$^+$.

Example 11 trans-4-[{3-[6-({[(2R)-2-hydroxy-2-(8-hydroxy-2-oxo-1,2-dihydroquinolin-5-yl)ethyl]amino}methyl)-2-oxo-1,3-benzothiazol-3(2H)-yl]propyl}(methyl) amino]cyclohexyl hydroxy(di-2-thienyl)acetate dihydrofluoride Obtained as a pale yellow solid (149 mg, 81% yield) from trans-4-[{3-[6-({[(2R)-2-{[tert-butyl(dimethyl)silyl]oxy}-2-(8-hydroxy-2-oxo-1,2-dihydroquinolin-5-yl)ethyl] amino}methyl)-2-oxo-1,3-benzothiazol-3(2H)-yl]propyl} (methyl)amino]cyclohexyl hydroxy(di-2-thienyl)acetate (Intermediate 74, 200 mg, 0.22 mmol) and triethylamine trihydrofluoride (150 µL, 0.92 mmol) following the experimental procedure described for the synthesis of Example 1.
LRMS (m/z): 775 (M+1)$^+$.
$^1$H NMR (300 MHz, dmso) δ 8.11 (d, J=10.0 Hz, 1H), 7.60 (s, 1H), 7.46 (dt, J=3.8, 1.9 Hz, 1H), 7.31 (dt, J=18.2, 9.1 Hz, 2H), 7.10-7.02 (m, 3H), 7.00-6.94 (m, 3H), 6.90 (d, J=8.1 Hz, 1H), 6.45 (d, J=9.9 Hz, 1H), 5.11 (bs, 1H), 4.68 (bs, 1H), 3.93 (bs, 3H), 3.84 (s, 2H), 2.72 (d, J=7.0 Hz, 2H), 2.44 (s, 2H), 2.14 (s, 3H), 1.91 (s, 2H), 1.72 (dd, J=15.0, 7.1 Hz, 4H), 1.37 (dd, J=19.6, 10.5 Hz, 4H).

Intermediate 75 methyl 4-amino-3-hydroxybenzoate 4-amino-3-hydroxybenzoic acid (5.0 g, 32.6 mmol) was added dropwise to a 0° C. solution of an HCl 1.25 M solution in MeOH(100 mL) and MeOH (100 mL). After 5 min of final addition the mixture was allowed to warm up to room temperature and stirred overnight. HPLC monitoring of the reaction showed remaining starting material and the mixture was stirred at ambient temperature for 48 hours. The solvent was then removed under reduced pressure and the residue was treated with saturated aqueous bicarbonate solution and the aqueous phase was extracted with AcOEt (2×). The combined organic extracts were washed with brine, dried over anhydrous sodium sulphate, filtered and concentrated to dryness obtaining the title compound (5.37 g, 97% yield) as a crystalline solid.
LRMS (m/z): 168 (M+1)$^+$.

Intermediate 76 methyl 2-oxo-2,3-dihydro-1,3-benzoxazole-6-carboxylate

To a solution of methyl 4-amino-3-hydroxybenzoate (Intermediate 75, 1.06 g, 6.34 mmol) in THF (13.5 mL) was added carbonyl diimidazole (1.88 g, 11.6 mmol) and the reaction mixture was heated to reflux temperature for 1 day. After that time, the solvent was removed and the residue was partitioned between $CH_2Cl_2$ and 1N aqueous HCl solution. The organic phase was washed with 1N aqueous HCl solution (2×) and water, dried over anhydrous sodium sulphate, filtered and concentrated under reduced pressure to provide the title compound as white solid (870 mg of a 79% purity, 56% yield). The crude was used in the next step without any further purification.
LRMS (m/z): 194 (M+1)$^+$.

Intermediate 77

6-(hydroxymethyl)-1,3-benzoxazol-2(3H)-one

To a solution of methyl 2-oxo-2,3-dihydro-1,3-benzoxazole-6-carboxylate (865 mg of 79% purity, 3.51 mmol) in THF (15 mL) was added, under argon atmosphere and at 0° C., lithium aluminium hydride (400 mg, 10.5 mmol) in portions in order to maintain the internal temperature below 5° C. After the last addition, the thick suspension was allowed to warm up to room temperature and stirred for 1.5 hours. Then, water was added (0.4 mL) dropwise followed by addition of 4N sodium hydroxide (0.4 mL) and water (1.2 mL). The mixture was filtered and the solid residue was washed with EtOH. The ethanolic phase was concentrated to dryness. The brown solid obtained was purified by reverse phase column chromatography over C18 modified silica gel eluting with water:MeOH (from 0 to 100% of MeOH) to give a pure fraction of the title compound (148 mg, 26% yield).
LRMS (m/z): 166 (M+1)$^+$.

Intermediate 78

6-({[tert-butyl(diphenyl)silyl]oxy}methyl)-1,3-benzoxazol-2(3H)-one

To a solution of 6-(hydroxymethyl)-1,3-benzoxazol-2 (3H)-one (Intermediate 77, 330 mg, 2.0 mmol) in DMF (10 mL) was added imidazole (203 mg, 2.98 mmol) and the reaction was cooled to 0° C. before tert-butylchlorodiphenylsilane (0.52 mL, 2.0 mmol) was added dropwise. Upon addition, the reaction was allowed to warm up to room temperature and stirring was maintained for 16 hours. Water and $CH_2Cl_2$ (40 mL each) were added to the reaction mixture and the phases were separated. The aqueous phase was extracted with $CH_2Cl_2$ (2×50 mL) and the resulting organic extracts were washed with water (2×50 mL) and brine (50 mL), dried over anhydrous sodium sulphate, filtered and concentrated under reduced pressure. The brown oil obtained was purified by column chromatography over silica gel eluting with Hexane:$Et_2O$ (from 0 to 100% of $Et_2O$) to afford the title compound as a beige solid (437 mg, 54% yield).
LRMS (m/z): 404 (M+1)$^+$.

Intermediate 79

6-({[tert-butyl(diphenyl)silyl]oxy}methyl)-3-(2-hydroxyethyl)-1,3-benzoxazol-2(3H)-one To a solution of 6-({[tert-butyl(diphenyl)silyl]oxy}methyl)-1,3-benzoxazol-2(3H)-one (Intermediate 78, 218 mg, 0.54 mmol) in DMF (2 mL) were added potassium carbonate (232 mg, 1.68 mmol) and 2-bromoethanol (60 µL, 0.85 mmol) and the reaction mixture was placed in a sealed vessel at 120° C. over a period of 4 hours. $CH_2Cl_2$ was added to the mixture and the solids were filtered off and washed with $CH_2Cl_2$. The resulting filtrate was washed with water and brine and the organic phase was filtered through a Phase Separator membrane to remove remaining water. The crude oil was purified by column chromatography over silica gel using Hexane:$Et_2O$ as eluent (from 0 to 100% of $Et_2O$) to give the title compound as a white solid (107 mg, 44% yield).
LRMS (m/z): 448 (M+1)$^+$.

Intermediate 80

2-[6-({[tert-butyl(diphenyl)silyl]oxy}methyl)-2-oxo-1,3-benzoxazol-3(2H)-yl]ethyl methanesulfonate Obtained as a colourless oil (139 mg of 90% purity by HPLC, 99% yield) from 6-({[tert-butyl(diphenyl)silyl]oxy}methyl)-3-(2-hydroxyethyl)-1,3-benzoxazol-2(3H)-one (Intermediate 79, 107 mg, 0.24 mmol), $Et_3N$ (50 µL, 0.34 mmol) and methanesulfonyl chloride (26 µL, 0.34 mmol) following the experimental procedure described for the synthesis of Intermediate 72. The crude was used for the next step without further purification.
LRMS (m/z): 526 (M+1)$^+$.

Intermediate 81 trans-4-[{2-[6-({[tert-butyl(diphenyl)silyl]oxy}methyl)-2-oxo-1,3-benzoxazol-3(2H)-yl]ethyl}(methyl)amino]cyclohexyl hydroxy(di-2-thienyl)acetate Obtained as a solid (92 mg of 88% purity by HPLC, 44% yield) from 2-[6-({[tert-butyl(diphenyl)silyl]oxy}methyl)-2-oxo-1,3-benzoxazol-3(2H)-yl]ethyl methanesulfonate (Intermediate 80, 139 mg, 0.24 mmol), trans-4-(methylamino) cyclohexyl hydroxy(di-2-thienyl)acetate (Intermediate 5, 95 mg, 0.27 mmol), sodium iodide (75 mg, 0.50 mmol) and DIEA (65 µL, 0.37 mmol) following the experimental procedure described for the synthesis of Intermediate 73. The crude was purified by column chromatography over silica gel eluting with Hexane:$Et_2O$ (from 0 to 100% of $Et_2O$).
LRMS (m/z): 781 (M+1)$^+$.

Intermediate 82 trans-4-[{2-[6-(hydroxymethyl)-2-oxo-1,3-benzoxazol-3(2H)-yl]ethyl}(methyl)amino]cyclohexyl hydroxy(di-2-thienyl)acetate To a solution of trans-4-[{2-[6-({[tert-butyl(diphenyl)silyl]oxy}methyl)-2-oxo-1,3-benzoxazol-3(2H)-yl]ethyl}(methyl)amino]cyclohexyl hydroxy(di-2-thienyl)acetate (Intermediate 81, 92 mg of 88% purity by HPLC, 0.10 mmol) in THF (1 mL) was added triethylamine trihydrofluoride (55 µL, 0.342 mmol) and the final solution was stirred at ambient temperature overnight. Saturated aqueous sodium bicarbonate and CHCl$_3$ were added and the phases separated. The aqueous phase was extracted with CHCl$_3$ (2×15 mL) and the combined organic extracts were filtered through a Phase Separator membrane and concentrated under reduced pressure. The solid residue was purified by column chromatography over silica gel eluting with CH$_2$Cl$_2$:EtOH (from 0 to 10% EtOH) to give the title compound as a colourless foam (40 mg, 70% yield).

LRMS (m/z): 543 (M+1)$^+$.

Intermediate 83 trans-4-[[2-(6-formyl-2-oxo-1,3-benzoxazol-3(2H)-yl)ethyl](methyl)amino]cyclohexyl hydroxy(di-2-thienyl)acetate To a solution of trans-4-[{2-[6-(hydroxymethyl)-2-oxo-1,3-benzoxazol-3(2H)-yl]ethyl}(methyl)amino]cyclohexyl hydroxy(di-2-thienyl)acetate (Intermediate 82, 40 mg, 0.07 mmol) in CH$_2$Cl$_2$ (1 mL) was added Dess-Martin periodinane reagent (45 mg, 0.11 mmol) and the mixture was stirred for 40 min. Saturated aqueous solutions of sodium bicarbonate and sodium thiosulfate were added (0.5 mL each) and stirring was maintained for 10 more min. The phases were separated and the aqueous phase was extracted with CH$_2$Cl$_2$ (2×5 mL). The combined organic extracts were filtered through a Phase Separator membrane and concentrated to dryness to afford the title compound (63 mg of 60% purity by HPLC, 100% yield) as a yellow oil. The crude oil was used as this without any further purification.

LRMS (m/z): 541 (M+1)$^+$.

Intermediate 84 trans-4-[{2-[6-({[(2R)-2-{[tert-butyl(di methyl)silyl]oxy}-2-(8-hydroxy-2-oxo-1,2-dihydroquinolin-5-yl)ethyl]amino}methyl)-2-oxo-1,3-benzoxazol-3(2H)-yl]ethyl}(methyl)amino]cyclohexyl hydroxy(di-2-thienyl)acetate Obtained as a yellow solid (44 mg of a 81% purity by HPLC, 59% yield) from trans-4-[[2-(6-formyl-2-oxo-1,3-benzoxazol-3(2H)-yl)ethyl](methyl)amino]cyclohexyl hydroxy(di-2-thienyl)acetate (Intermediate 83, 63 mg of a 60% purity by HPLC, 0.07 mmol), 5-((1 R)-2-amino-1-{[tert-butyl(dimethyl)-silyl]oxy}ethyl)-8-hydroxyquinolin-2(1H)-one acetate (prepared according to preparation 8 from US20060035931, 32 mg, 0.10 mmol) DIEA (21 µL, 0.12 mmol) and sodium triacetoxyborohydride (107 mg, 0.50 mmol) following the experimental procedure described for the synthesis of Intermediate 10. The crude obtained was purified by column chromatography over silica gel, eluting with a mixture of CHCl$_3$:EtOH (from 0 to 50% of EtOH).

LRMS (m/z): 859 (M+1)$^+$.

Example 12 trans-4-[{2-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]ethyl}(methyl)amino]cyclohexyl hydroxy(di-2-thienyl)acetate dihydrofluoride Obtained as a pale yellow solid (29 mg, 72% yield) from trans-4-[{2-[6-({[(2R)-2-{[tert-butyl(dimethyl)silyl]oxy}-2-(8-hydroxy-2-oxo-1,2-dihydroquinolin-5-yl)ethyl]amino}-methyl)-2-oxo-1,3-benzoxazol-3(2H)-yl]ethyl}(methyl)amino]cyclohexyl hydroxy(di-2-thienyl)acetate (Intermediate 84, 44 mg, 0.05 mmol) and triethylamine trihydrofluoride (40 µL, 0.25 mmol) following the experimental procedure described for the synthesis of Example 1.

LRMS (m/z): 745 (M+1)$^+$.

$^1$H NMR (300 MHz, dmso) δ 8.13 (d, J=9.8 Hz, 1H), 7.45 (d, J=4.4 Hz, 1H), 7.36 (bs, 2H), 7.23 (bs, 2H), 7.05 (bs, 3H), 7.01-6.85 (m, 3H), 6.48 (d, J=10.1 Hz, 1H), 5.14 (bs, 1H), 4.62 (bs, 1H), 3.86 (d, J=7.0 Hz, 2H), 2.70 (d, J=16.0 Hz, 3H), 2.35 (s, 3H), 2.22 (bs, 2H), 1.91 (bs, 2H), 1.81 (bs, 2H), 1.49 (bs, 2H), 1.41-1.13 (m, 3H).

Intermediate 85

3-(4-hydroxybutyl)-2-oxo-2,3-dihydro-1,3-benzoxazole-6-carbaldehyde

Obtained as a solid (120 mg of a 76% purity by HPLC, 35% yield) from 2-oxo-2,3-dihydro-1,3-benzoxazole-6-carbaldehyde (Intermediate 7, 180 mg, 1.10 mmol), 4-bromobutan-1-ol (255 mg, 1.67 mmol), potassium carbonate (460 mg, 3.33 mmol) and potassium iodide (92 mg, 0.55 mmol) following the procedure described for the synthesis of Intermediate 71. The crude residue was purified by column chromatography over silica gel eluting with CH$_2$Cl$_2$:EtOH (from 0 to 5% of EtOH).

Intermediate 86

4-(6-formyl-2-oxo-1,3-benzoxazol-3(2H)-yl)butyl methanesulfonate

Obtained as a colourless oil (153 mg of 80% purity by HPLC, 99% yield) from 3-(4-hydroxybutyl)-2-oxo-2,3-dihydro-1,3-benzoxazole-6-carbaldehyde (Intermediate 85, 120 mg of 76% purity by HPLC, 0.39 mmol), Et$_3$N (145 µL, 1.05 mmol) and methanesulfonyl chloride (64 µL, 0.83 mmol) following the experimental procedure described for the synthesis of Intermediate 72. The crude was used for the next step without further purification.

LRMS (m/z): 314 (M+1)$^+$.

Intermediate 87 trans-4-[[4-(6-formyl-2-oxo-1,3-benzoxazol-3(2H)-yl)butyl](methyl)amino]-cyclohexyl hydroxy(di-2-thienyl)acetate Obtained as a solid (93 mg, 42% yield) from 4-(6-formyl-2-oxo-1,3-benzoxazol-3(2H)-yl)butyl methanesulfonate (Intermediate 86, 121 mg, 0.39 mmol), trans-4-(methylamino)cyclohexyl hydroxy(di-2-thienyl)acetate (Intermediate 5, 137 mg, 0.39 mmol), sodium iodide (145 mg, 0.97 mmol)

and DIEA (105 μL, 0.58 mmol) following the experimental procedure described for the synthesis of Intermediate 73. The crude was purified by column chromatography over silica gel eluting with CH$_2$Cl$_2$:MeOH (from 0 to 100% of MeOH).

LRMS (m/z): 569 (M+1)$^+$.

Intermediate 88 trans-4-[{4-[6-({[(2R)-2-{[tert-butyl(di methyl)silyl]oxy}-2-(8-hydroxy-2-oxo-1,2-dihydroquinolin-5-yl)ethyl]amino}methyl)-2-oxo-1,3-benzoxazol-3(2H)-yl]butyl}(methyl)amino]cyclohexyl hydroxy(di-2-thienyl)acetate Obtained as a solid (80 mg of 62% purity by HPLC, 35% yield) from trans-4-[[4-(6-formyl-2-oxo-1,3-benzoxazol-3(2H)-yl)butyl](methyl)amino]cyclohexyl hydroxy(di-2-thienyl)acetate (Intermediate 87, 90 mg, 0.16 mmol), 5-((1R)-2-amino-1-{[tert-butyl(dimethyl)-silyl]oxy}ethyl)-8-hydroxyquinolin-2(1H)-one acetate (prepared according to preparation 8 from US20060035931, 69 mg, 0.17 mmol) and sodium triacetoxyborohydride (135 mg, 0.64 mmol) following the experimental procedure described for the synthesis of Intermediate 10. The crude obtained was purified by column chromatography over silica gel, eluting with a mixture of CHCl$_3$:EtOH (from 0 to 50% of EtOH).

LRMS (m/z): 887 (M+1)$^+$.

Example 13 trans-4-[{4-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]butyl}(methyl)amino]cyclohexyl hydroxy(di-2-thienyl)acetate dihydrofluoride Obtained as a pale yellow solid (44 mg, 98% yield) from trans-4-[{4-[6-({[(2R)-2-{[tert-butyl(dimethyl)silyl]oxy}-2-(8-hydroxy-2-oxo-1,2-dihydroquinolin-5-yl)ethyl]amino}-methyl)-2-oxo-1,3-benzoxazol-3(2H)-yl]butyl}(methyl)amino]cyclohexyl hydroxy(di-2-thienyl)acetate (Intermediate 88, 79 mg of a 62% purity by HPLC, 0.06 mmol) and triethylamine trihydrofluoride (40 μL, 0.25 mmol) following the experimental procedure described for the synthesis of Example 1.

LRMS (m/z): 773 (M+1)$^+$.

$^1$H NMR (300 MHz, dmso) δ 8.30 (d, J=9.9 Hz, 1H), 7.65 (bs, 2H), 7.49 (s, 1H), 7.44-7.28 (m, 2H), 7.24 (dd, J=8.1, 4.6 Hz, 3H), 7.18-7.03 (m, 3H), 6.64 (d, J=9.9 Hz, 1H), 5.32 (s, 1H), 5.29-5.18 (m, 1H), 4.85 (s, 1H), 3.97 (d, J=7.3 Hz, 4H), 2.85 (s, 3H), 2.54 (d, J=7.1 Hz, 4H), 2.28 (d, J=5.4 Hz, 2H), 2.08 (bs, 2H), 1.85 (bs, 4H), 1.66-1.40 (m, 4H).

Intermediate 89 trans-4-[(3-{5-[({(2R)-2-{[tert-butyl(dimethyl)silyl]oxy}-2-[3-(formylamino)-4-hydroxyphenyl]ethyl}amino)methyl]-2-oxo-2,3-dihydro-1H-benzimidazol-1-yl}propyl)(methyl)amino]cyclohexyl hydroxy(di-2-thienyl)acetate Obtained as a solid (56 mg of 71% purity by HPLC, 56% yield) from trans-4-[[3-(5-formyl-2-oxo-2,3-dihydro-1H-benzimidazol-1-yl)propyl](methyl)amino]cyclohexyl hydroxy(di-2-thienyl)acetate (Intermediate 16, 46 mg, 0.08 mmol), N-[5-[(R)-2-amino-1-(tert-butyldimethylsilyloxy)ethyl]-2-hydroxyphenylformamide acetate (prepared according to the preparation of Example 3 from WO2007127297, 33 mg, 0.09 mmol) and sodium triacetoxyborohydride (605 mg, 0.28 mmol) following the experimental procedure described for the synthesis of Intermediate 10. The crude obtained was purified by column chromatography over silica gel, eluting with a mixture of CHCl$_3$:EtOH (from 0 to 50% of EtOH).

LRMS (m/z): 848 (M+1)$^+$.

Example 14 trans-4-[(3-{5-[({(2R)-2-[3-(formylamino)-4-hydroxyphenyl]-2-hydroxyethyl}amino)methyl]-2-oxo-2,3-dihydro-1H-benzimidazol-1-yl}propyl)(methyl)amino]cyclohexyl hydroxy(di-2-thienyl)acetate dihydrofluoride Obtained as a pale yellow solid from trans-4-[(3-{5-[({(2R)-2-{[tert-butyl(dimethyl)-silyl]oxy}-2-[3-(formylamino)-4-hydroxyphenyl]ethyl}amino)methyl]-2-oxo-2,3-dihydro-1H-benzimidazol-1-yl}propyl)(methyl)amino]cyclohexyl hydroxy(di-2-thienyl)acetate (56 mg of 71% purity by HPLC, 0.05 mmol) and triethylamine trihydrofluoride (30 μL, 0.19 mmol) following the experimental procedure described for the synthesis of Example 1.

LRMS (m/z): 734 (M+1)$^+$.

$^1$H NMR (300 MHz, dmso) δ 9.53 (s, 1H), 8.24 (d, J=6.5 Hz, 1H), 8.00 (s, 1H), 7.47-7.36 (m, 2H), 7.22 (bs, 2H), 7.09-6.71 (m, 6H), 4.65 (bs, 1H), 4.54 (bs, 1H), 3.74 (d, J=6.7 Hz, 2H), 2.57 (s, 3H), 2.40-2.3 (m, 3H), 2.07 (bs, 4H), 1.87 (d, J=4.9 Hz, 2H), 1.67 (bs, 4H), 1.32 b(s, 4H).

Intermediate 90

3-(3-hydroxypropyl)-2-oxo-2,3-dihydro-1,3-benzoxazole-6-carbaldehyde

Obtained as a solid (191 mg of 85% purity by HPLC, 49% yield) from 2-oxo-2,3-dihydro-1,3-benzoxazole-6-carbaldehyde (Intermediate 7, 245 mg, 1.50 mmol), 3-bromopropan-1-ol (190 μL, 2.11 mmol), potassium carbonate (620 mg, 4.50 mmol) and potassium iodide (125 mg, 0.75 mmol) following the experimental procedure described for the synthesis of Intermediate 71. The crude residue was purified by column chromatography over silica gel eluting with CH$_2$Cl$_2$:EtOH (from 0 to 10% of EtOH).

LRMS (m/z): 222 (M+1)$^+$.

Intermediate 91

3-(6-formyl-2-oxo-1,3-benzoxazol-3(2H)-yl)propyl methanesulfonate

Obtained as a colourless oil (297 mg of 86% purity by HPLC, 99% yield) from 3-(3-hydroxypropyl)-2-oxo-2,3-dihydro-1,3-benzoxazole-6-carbaldehyde (Intermediate 90, 190 mg of 85% purity by HPLC, 0.85 mmol), Et$_3$N (145 μL, 1.05 mmol) and methanesulfonyl chloride (75 μL, 0.97 mmol) following the experimental procedure described for the synthesis of Intermediate 72. The crude was used for the next step without further purification.

LRMS (m/z): 300 (M+1)$^+$.

Intermediate 92 trans-4-[[3-(6-formyl-2-oxo-1,3-benzoxazol-3(2H)-yl)propyl](methyl)amino]cyclohexyl 9-methyl-9H-xanthene-9-carboxylate Obtained as a solid (298 mg, 54% yield) from 3-(6-formyl-2-oxo-1,3-benzoxazol-3(2H)-yl)propyl methanesulfonate (Intermediate 91, 297 mg, 0.99 mmol), trans-4-(methylamino)cyclohexyl 9-methyl-9H-xanthene-9-carboxylate (prepared according to preparation of Intermediate 162 from WO2011141180, 349 mg, 0.99 mmol), sodium iodide (372 mg, 2.48 mmol) and DIEA (260 µL, 1.49 mmol) following the experimental procedure described for the synthesis of Intermediate 73. The crude was purified by column chromatography over silica gel eluting with $CH_2Cl_2$:EtOH (from 0 to 100% of EtOH).
LRMS (m/z): 555 (M+1)$^+$.

Intermediate 93 trans-4-[{3-[6-({[(2R)-2-{[tert-butyl(di methyl)silyl]oxy}-2-(8-hydroxy-2-oxo-1,2-dihydroquinolin-5-yl)ethyl]amino}methyl)-2-oxo-1,3-benzoxazol-3(2H)-yl]propyl}(methyl)amino]cyclohexyl 9-methyl-9H-xanthene-9-carboxylate Obtained as a solid (110 mg, 44% yield) from trans-4-[[3-(6-formyl-2-oxo-1,3-benzoxazol-3(2H)-yl)propyl](methyl)amino]cyclohexyl 9-methyl-9H-xanthene-9-carboxylate (Intermediate 92, 160 mg, 0.29 mmol), 5-((1 R)-2-amino-1-{[tert-butyl(dimethyl)-silyl]oxy}ethyl)-8-hydroxyquinolin-2(1H)-one acetate (prepared according to preparation 8 from US20060035931, 135 mg, 0.34 mmol) and sodium triacetoxyborohydride (200 mg, 0.94 mmol) following the experimental procedure described for the synthesis of Intermediate 10. The crude obtained was purified by column chromatography over silica gel, eluting with a mixture of $CHCl_3$:$CHCl_3$/MeOH/$NH_4OH$ (40/4/0.2) (from 0 to 100% of $CHCl_3$/MeOH/$NH_4OH$ (40/4/0.2)).
LRMS (m/z): 874 (M+1)$^+$.

Example 15 trans-4-[{3-[6-({[(2R)-2-hydroxy-2-(8-hydroxy-2-oxo-1,2-dihydroquinolin-5-yl)ethyl]amino}methyl)-2-oxo-1,3-benzoxazol-3(2H)-yl]propyl}(methyl)amino]cyclohexyl 9-methyl-9H-xanthene-9-carboxylate dihydrofluoride Obtained as a pale yellow solid from trans-4-[{3-[6-({[(2R)-2-{[tert-butyl(dimethyl)-silyl]oxy}-2-(8-hydroxy-2-oxo-1,2-dihydroquinolin-5-yl)ethyl]amino}methyl)-2-oxo-1,3-benzoxazol-3(2H)-yl]propyl}(methyl)amino]cyclohexyl 9-methyl-9H-xanthene-9-carboxylate (Intermediate 93, 110 mg, 0.13 mmol) and triethylamine trihydrofluoride (80 µL, 0.50 mmol) following the experimental procedure described for the synthesis of Example 1.
LRMS (m/z): 759 (M+1)$^+$.
$^1$H NMR (300 MHz, dmso) δ 8.13 (d, J=9.9 Hz, 1H), 7.40-7.23 (m, 4H), 7.20 (s, 1H), 7.13 (bs, 4H), 7.1-7.02 (m, 2H), 6.91 (d, J=8.1 Hz, 2H), 6.47 (d, J=9.9 Hz, 1H), 5.13 (bs, 1H), 4.55 (t, J=10.8 Hz, 1H), 3.87 (s, 2H), 3.77 (t, J=6.8 Hz, 2H), 2.72 (t, J=5.8 Hz, 2H), 2.38 (dd, J=20.3, 14.1 Hz, 2H), 2.27 (bs, 2H), 2.07 (s, 2H), 1.71 (d, J=16.8 Hz, 4H), 1.55 (d, J=10.9 Hz, 2H), 1.27 (dd, J=29.5, 17.5 Hz, 2H), 1.03 (bs, 2H).

Intermediate 94 trans-4-[{3-[6-[({(2R)-2-{[tert-butyl(dimethyl)silyl]oxy}-2-[3-(formylamino)-4-hydroxyphenyl]ethyl}amino)methyl]-2-oxo-1,3-benzoxazol-3(2H)-yl]propyl}(methyl)amino]cyclohexyl 9-methyl-9H-xanthene-9-carboxylate Obtained as a solid (87 mg, 42% yield) from trans-4-[[3-(6-formyl-2-oxo-1,3-benzoxazol-3(2H)-yl)propyl](methyl)amino]cyclohexyl 9-methyl-9H-xanthene-9-carboxylate (Intermediate 92, 135 mg, 0.24 mmol), N-[5-[(R)-2-amino-1-(tert-butyldimethylsilyloxy)ethyl]-2-hydroxyphenylformamide acetate (prepared according to the preparation of Example 3 from WO2007127297, 83 mg, 0.27 mmol) and sodium triacetoxyborohydride (360 mg, 1.70 mmol) following the experimental procedure described for the synthesis of Intermediate 10. The crude obtained was purified by column chromatography over silica gel, eluting with a mixture of $CHCl_3$:$CHCl_3$/MeOH/$NH_4OH$ (40/4/0.2) (from 0 to 100% of $CHCl_3$/MeOH/$NH_4OH$ (40/4/0.2)).
LRMS (m/z): 850 (M+1)$^+$.

Example 16 trans-4-[{3-[6-[({(2R)-2-[3-(formylamino)-4-hydroxyphenyl]-2-hydroxyethyl}amino)methyl]-2-oxo-1,3-benzoxazol-3(2H)-yl]propyl}(methyl)amino]cyclohexyl 9-methyl-9H-xanthene-9-carboxylate dihydrofluoride Obtained as a pale yellow solid from trans-4-[{3-[6-[({(2R)-2-{[tert-butyl(dimethyl)-silyl]oxy}-2-[3-(formylamino)-4-hydroxyphenyl]ethyl}amino)methyl]-2-oxo-1,3-benzoxazol-3(2H)-yl]propyl}(methyl)amino]cyclohexyl 9-methyl-9H-xanthene-9-carboxylate (Intermediate 94, 87 mg, 0.10 mmol) and triethylamine trihydrofluoride (66 µL, 0.41 mmol) following the experimental procedure described for the synthesis of Example 1.
LRMS (m/z): 735 (M+1)$^+$.
$^1$H NMR (300 MHz, dmso) δ 9.56 (s, 1H), 8.25 (d, J=1.9 Hz, 1H), 8.03 (d, J=1.8 Hz, 1H), 7.38-7.22 (m, 2H), 7.19 (bs, 3H), 7.16-7.07 (m, 4H), 6.86 (dd, J=8.3, 1.8 Hz, 1H), 6.79 (d, J=8.2 Hz, 1H), 4.56 (dd, J=16.4, 8.6 Hz, 1H), 3.78 (dd, J=16.7, 9.6 Hz, 2H), 2.61 (d, J=6.0 Hz, 3H), 2.39 (t, J=6.5 Hz, 2H), 2.25 (bs, 4H), 2.08 (bs, 2H), 1.76 (s, 3H), 1.55 (bs, 2H), 1.25 (bs, 4H), 1.12-0.95 (m, 4H).

Intermediate 95

4-[(3-hydroxypropyl)amino]-3-nitrobenzonitrile

To a solution of 4-fluoro-3-nitrobenzonitrile (10 g, 0.06 mol) in THF (50 mL) was added in portions, via syringe, 3-aminopropanol (5 mL, 0.07 mol) and the mixture was stirred at room temperature. After one hour of reaction the crude mixture was evaporated to dryness and AcOEt was added (300 mL). The organic layer was washed with aqueous sodium bicarbonate (250 mL of a 4% aqueous solution) and the aqueous phase was further extracted with AcOEt (2×100 mL). The combined organic extracts were washed with brine, dried over anhydrous sodium sulphate, and concentrated under reduced pressure to give the title compound as an orange solid (13.4 g, 99% yield) which was used in the next step without further purification.
LRMS (m/z): 222 (M+1)$^+$.

Intermediate 96

3-amino-4-[(3-hydroxypropyl)amino]benzonitrile

To a suspension of 4-[(3-hydroxypropyl)amino]-3-nitrobenzonitrile (Intermediate 95, 13.4 g, 0.06 mol) in EtOH (500 mL) was added, under argon atmosphere, palladium over carbon (350 mg, 3.3 mmol of a 10% Pd/C) and the mixture was degassed. Then, $H_2$ was added up to an internal pressure of 20 psi, and the final suspension was stirred at room temperature for 2.5 hours. The crude was filtered through a Whatmann glass micro fibre filter and the solvent was removed under reduced pressure to afford the title compound as a brownish solid (11.5 g, 95% yield) which was used in the next step without further purification.

LRMS (m/z): 192 (M+1)$^+$.

Intermediate 97

1-(3-hydroxypropyl)-1H-1,2,3-benzotriazole-5-carbonitrile

To a vigorously stirred solution of 3-amino-4-[(3-hydroxypropyl)amino]benzonitrile (Intermediate 96, 11.5 g, 0.06 mol) in aqueous HCl (105 mL of a 5N HCl solution) was added, dropwise an 0° C., a solution of sodium nitrite (6.2 g, 0.09 mol) in water (47 mL). After 3.5 hours of vigorously stirring at 0° C., water was added (200 mL) and the reaction mixture extracted with AcOEt (3×150 mL). The combined organic extracts were washed with water (3×100 mL) and brine, and the resulting organic phase was evaporated to dryness to deliver the title compound as a brownish solid (10.8 g, 86%) which was used without further purification.

LRMS (m/z): 203 (M+1)$^+$.

Intermediate 98

1-(3-hydroxypropyl)-1H-1,2,3-benzotriazole-5-carbaldehyde

To a solution of 1-(3-hydroxypropyl)-1H-1,2,3-benzotriazole-5-carbonitrile (Intermediate 97, 9.6 g, 47.5 mmol) in aqueous Formic Acid (106 mL of a 75% solution in water) was added Niquel-Aluminium alloy (10.6 g, 0.12 mol). The mixture was stirred overnight at 75° C. The solids were removed by filtration through Celite® and the solvent was removed under reduced pressure. The crude obtained was treated with MeOH (415 mL) and potassium carbonate was added (49 g, 0.35 mol). After 1h the solution was acidified with 2N HCl until neutral pH and MeOH evaporated under reduced pressure. The aqueous phase was extracted with $CH_2Cl_2$ (3×200 mL) and the resulting organic layer washed with water (2×50 mL), dried and evaporated under reduced pressure to afford the title compound as a solid (6.05 g, 60% yield), which was used in the next step without further purification.

LRMS (m/z): 206 (M+1)$^+$.

Intermediate 99

3-(5-formyl-1H-1,2,3-benzotriazol-1-yl)propyl methanesulfonate

Obtained as a colourless oil (701 mg, 99% yield) from of 1-(3-hydroxypropyl)-1H-1,2,3-benzotriazole-5-carbaldehyde (Intermediate 98, 500 mg, 2.44 mmol), Et$_3$N (0.41 mL, 2.96 mmol) and methanesulfonyl chloride (0.19 mL, 2.45 mmol) following the experimental procedure described for the synthesis of Intermediate 72. The crude obtained was used without further purification.

LRMS (m/z): 284 (M+1)$^+$.

Intermediate 100 trans-4-[[3-(5-formyl-1H-1,2,3-benzotriazol-1-yl) propyl](methyl)amino]cyclohexyl (2S)-cyclopentyl (hydroxy)2-thienylacetate To a solution of trans-4-(methylamino)cyclohexyl (2S)-cyclopentyl(hydroxy)2-thienylacetate (Intermediate 172 from WO2011/141180A1, 318 mg, 0.93 mmol) in DMF (3 mL) was added sodium iodide (355 mg, 2.37 mmol) and DIEA (0.25 mL, 1.44 mmol). To this suspension a solution of 3-(5-formyl-1H-1,2,3-benzotriazol-1-yl)propyl methanesulfonate (Intermediate 99, 380 mg, 1.17 mmol) in DMF (2 mL) was added and the mixture was stirred at 75° C. for 7 hours. The reaction mixture was evaporated to dryness, the solid residue was re-suspended in CHCl$_3$ (30 mL) and the suspension was filtered through Celite®. The solvent was removed under reduced pressure and the resulting yellow solid was purified by column chromatography over silica gel eluting with a mixture of $CH_2Cl_2$/EtOH (gradient from 0 to 100% of EtOH) to provide the title compound as a yellow solid (473 mg (70% purity by HPLC), 68% yield).

LRMS (m/z): 525 (M+1)$^+$.

Intermediate 101 trans-4-[{3-[5-({[(2R)-2-{[tert-butyl(di methyl)silyl] oxy}-2-(8-hydroxy-2-oxo-1,2-dihydroquinolin-5-yl) ethyl]amino}methyl)-1H-1,2,3-benzotriazol-1-yl] propyl}(methyl)amino]cyclohexyl (2S)-cyclopentyl (hydroxy)2-thienylacetate Obtained as a solid (144 mg, 35% yield (60% purity by HPLC) from trans-4-[[3-(5-formyl-1H-1,2,3-benzotriazol-1-yl)propyl](methyl)amino]cyclohexyl (2S)-cyclopentyl (hydroxy)2-thienylacetate (Intermediate 100, 221 mg, 0.29 mmol), 5-((1R)-2-amino-1-{[tert-butyl(dimethyl)-silyl] oxy}ethyl)-8-hydroxyquinolin-2(1H)-one acetate (prepared according to preparation 8 from US20060035931, 120 mg, 0.30 mmol) and sodium triacetoxyborohydride (560 mg, 2.64 mmol) following the experimental procedure described for the synthesis of Intermediate 10. The crude obtained was purified by column chromatography over silica gel, eluting with a mixture of hexane:Et$_2$O:EtOH (from 0 to 100% of Et$_2$O and then from 0 to 100% of EtOH).

LRMS (m/z): 843 (M+1)$^+$.

Example 17 trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino] cyclohexyl (2S)-cyclopentyl(hydroxy)2-thienylacetate dihydrofluoride Obtained as a pale yellow solid (80 mg, 92% yield) from trans-4-[{3-[5-({[(2R)-2-{[tert-butyl(dimethyl)silyl]oxy}-2-(8-hydroxy-2-oxo-1,2-dihydroquinolin-5-yl)ethyl] amino}-methyl)-1H-1,2,3-benzotriazol-1-yl]propyl} (methyl)amino]cyclohexyl (2S)-cyclopentyl(hydroxy)2-thienylacetate (Intermediate 101, 144 mg of a 60% purity, 0.1 mmol) and triethylamine trihydrofluoride (65 μL, 0.41 mmol) following the experimental procedure described for the synthesis of Example 1.

LRMS (m/z): 729 (M+1)$^+$.

$^1$H NMR (300 MHz, dmso) δ 8.09 (d, J=10.0 Hz, 1H), 8.03 (s, 1H), 7.83 (d, J=8.4 Hz, 1H), 7.59 (d, J=8.5 Hz, 1H), 7.38 (dd, J=5.1, 1.2 Hz, 1H), 7.07 (bs, 2H), 7.00-6.85 (m, 2H), 6.44 (d, J=10.0 Hz, 1H), 5.95 (bs, 1H), 5.17 (bs, 1H), 4.71 (bs, 2H), 4.56 (bs, 2H), 4.06 (bs, 2H), 2.88-2.60 (m, 3H), 2.47-2.28 (m, 2H), 2.16 (bs, 2H), 2.06 (bs, 2H), 1.91 (bs, 2H), 1.86-1.73 (m, 2H), 1.67 (bs, 4H), 1.5-1.39 (m, 8H).

Intermediate 102 trans-4-[{3-[5-({[(2R)-2-{[tert-butyl(dimethyl)silyl]oxy}-2-(5-hydroxy-3-oxo-3,4-dihydro-2H-1,4-benzoxazin-8-yl)ethyl]amino}methyl)-1H-1,2,3-benzotriazol-1-yl]propyl}(methyl)amino]cyclohexyl (2S)-cyclopentyl(hydroxy)2-thienylacetate Obtained as a solid (97 mg, 47% yield (66% purity by HPLC)) from trans-4-[[3-(5-formyl-1H-1,2,3-benzotriazol-1-yl)propyl](methyl)amino]cyclohexyl (2S)-cyclopentyl-(hydroxy)2-thienylacetate (Intermediate 100, 100 mg, 0.19 mmol), 8-[(R)-2-amino-1-(tert-butyl-dimethyl-silanoxy)-ethyl-5-hydroxy-4H-benzo[1,4]oxazin-3-one (prepared according to intermediate 65 from WO2008149110, 60 mg, 0.16 mmol) and sodium triacetoxyborohydride (209 mg, 0.99 mmol) following the experimental procedure described for the synthesis of Intermediate 10. The crude obtained was purified by column chromatography over silica gel, eluting with a mixture of CH$_2$Cl$_2$:EtOH (from 0 to 50% of EtOH).

LRMS (m/z): 848 (M+1)$^+$.

Example 18 trans-4-[{3-[5-({[(2R)-2-hydroxy-2-(5-hydroxy-3-oxo-3,4-dihydro-2H-1,4-benzoxazin-8-yl)ethyl]amino}methyl)-1H-1,2,3-benzotriazol-1-yl]propyl}(methyl)amino]cyclohexyl (2S)-cyclopentyl(hydroxy)2-thienylacetate dihydrofluoride Obtained as a pale yellow solid (47 mg, 81% yield) from trans-4-[{3-[5-({[(2R)-2-{[tert-butyl(dimethyl)silyl]oxy}-2-(5-hydroxy-3-oxo-3,4-dihydro-2H-1,4-benzoxazin-8-yl)ethyl]amino}methyl)-1H-1,2,3-benzotriazol-1-yl]propyl}(methyl)amino]cyclohexyl (2S)-cyclopentyl(hydroxy)2-thienylacetate (Intermediate 102, 97 mg of a 66% purity, 0.08 mmol), and triethylamine trihydrofluoride (50 μL, 0.31 mmol) following the experimental procedure described for the synthesis of Example 1.

LRMS (m/z): 729 (M+1)$^+$.

$^1$H NMR (300 MHz, dmso) δ 9.99 (bs, 1H), 7.98 (s, 1H), 7.82 (d, J=8.5 Hz, 1H), 7.55 (s, 1H), 7.38 (d, J=4.9 Hz, 1H), 7.05 (s, 1H), 6.96 (s, 1H), 6.85 (d, J=8.5 Hz, 1H), 6.48 (d, J=8.3 Hz, 1H), 5.96 (s, 1H), 4.93 (bs, 1H), 4.71 (bs 2H), 4.57 (bs, 2H), 4.43 (t, J=9.0 Hz, 2H), 3.98 (bs, 2H), 2.77-2.53 (m, 2H), 2.39 (s, 3H), 2.10 (bs, 2H), 2.02 (bs, 4H), 1.97-1.60 (m, 4H), 1.60-1.15 (m, 8H), 1.10 (d, J=6.9 Hz, 2H).

Intermediate 103

3-(3-{[tert-butyl(dimethyl)silyl]oxy}propyl)-2-oxo-2,3-dihydro-1,3-benzoxazole-6-carbaldehyde To a solution of 2-oxo-2,3-dihydro-1,3-benzoxazole-6-carbaldehyde (Intermediate 7, 300 mg, 1.84 mmol) in DMF (10 mL) were added potassium carbonate (633 mg, 4.58 mmol) and (3-bromopropoxy)(tert-butyl)dimethylsilane (0.47 mL, 2.03 mmol), and the resulting mixture was heated to 75° C. Upon complete disappearance of starting material (ca 16 hours), the solvent was removed under reduced pressure and the solid residue was treated with CH$_2$Cl$_2$ and stirred for 5 min. The suspension was filtered through Celite® and the solid residue washed with additional CH$_2$Cl$_2$. The filtrate was concentrated to dryness and the crude was purified by column chromatography over silica gel, eluting with Hexane:Et$_2$O (from 0 to 32% of Et$_2$O) to give the title compound as a white solid (550 mg, 89% yield).

LRMS (m/z): 336 (M+1)$^+$.

Intermediate 104

3-(3-{[tert-butyl(di methyl)silyl]oxy}propyl)-6-[(E/Z)-2-methoxyvinyl]-1,3-benzoxazol-2(3H)-one A solution of methoxymethyltriphenylphosphonium chloride (1.2 g, 3.5 mmol) in THF (7 mL) was treated, under argon atmosphere and at 0° C., with lithium hexamethyldisilazide (3.5 mL of a 1M solution in toluene, 3.5 mmol) and the mixture was stirred at this temperature for 30 min. Then, a solution of 3-(3-{[tert-butyl(dimethyl)silyl]oxy}propyl)-2-oxo-2,3-dihydro-1,3-benzoxazole-6-carbaldehyde (Intermediate 103, 468 mg, 1.4 mmol) in THF (4 mL) was added and stirring was maintained at room temperature for 14 hours. Saturated aqueous ammonium chloride solution and AcOEt were added (30 mL each) and stirring was maintained for 5 min. Water was added (10 mL), the layers were separated and the aqueous phase was extracted with AcOEt (3×40 mL). The resulting organic phase was washed with water and brine (60 mL each), dried over anhydrous sodium sulphate, filtered and evaporated to dryness. The resulting oil was purified by column chromatography over silica gel eluting with Hexane:Et$_2$O (from 0 to 100% of Et$_2$O) to afford the title compound as a colourless oil (432 mg of a 1:1 E:Z mixture, 85% yield).

LRMS (m/z): 364 (M+1)$^+$.

Intermediate 105

3-(3-hydroxypropyl)-6-[(E/Z)-2-methoxyvinyl]-1,3-benzoxazol-2(3H)-one

To a solution of TBAF (1.15 mL of a 1M solution in THF, 1.15 mmol) glacial AcOH was added dropwise (0.2 mL) and the final mixture was added to a solution of 3-(3-{[tert-butyl(dimethyl)silyl]oxy}propyl)-6-[(E/Z)-2-methoxyvinyl]-1,3-benzoxazol-2(3H)-one (Intermediate 104, 378 mg, 1.04 mmol) in THF (1 mL). The reaction mixture was stirred at room temperature fro 14 hours. Saturated aqueous ammonium chloride solution (10 mL), water (10 mL) and Et$_2$O (20 mL) were added. The aqueous phase was separated and further extracted with Et$_2$O (4×30 mL) and the organic phase was dried over anhydrous sodium sulphate, filtered and concentrated under reduced pressure. The residue was purified by column chromatography over silica gel eluting with Hexane:Et$_2$O (from 0 to 100% of Et$_2$O) to provide the title compound as a colourless oil (228 mg of a 1:1 E/Z mixture, 88% yield)

LRMS (m/z): 250 (M+1)$^+$.

Intermediate 106

3-[6-[(E/Z)-2-methoxyvinyl]-2-oxo-1,3-benzoxazol-3(2H)-yl]propyl methanesulfonate Obtained as a colourless oil (356 mg of a 1:1 E/Z mixture (92% purity by HPLC), 98% yield) from 3-(3-hydroxypropyl)-6-[(E/Z)-2-methoxyvinyl]-1,3-benzoxazol-2(3H)-one (Intermediate 105, 254 mg, 1.02 mmol), methanesulfonyl chloride (80 μL, 1.03 mmol) and Et$_3$N (160 μL, 1.15 mmol) following the experimental procedure described for the synthesis of Intermediate 100.

LRMS (m/z): 328 (M+1)$^+$.

Intermediate 107 trans-4-[{3-[6-[(E/Z)-2-methoxyvinyl]-2-oxo-1,3-benzoxazol-3(2H)-yl]propyl}(methyl)amino]cyclohexyl hydroxy(di-2-thienyl)acetate Obtained as a brownish oil (500 mg of a 1:1 E/Z mixture (90% purity by HPLC), 86% yield) from trans-4-(methylamino)cyclohexyl hydroxy(di-2-thienyl)acetate (Intermediate 5, 315 mg, 0.9 mmol), 3-[6-[(E/Z)-2-methoxyvinyl]-2-oxo-1,3-benzoxazol-3(2H)-yl]propyl methanesulfonate (Intermediate 106, 356 mg, 1.0 mmol), sodium iodide (290 mg, 1.93 mmol) and DIEA (0.24 mL, 1.38 mmol). following the experimental procedure described for the synthesis of Intermediate 101. The crude was purified by column chromatography over silica gel eluting with a mixture of CH$_2$Cl$_2$/EtOH (gradient from 0 to 100% of EtOH).

LRMS (m/z): 583 (M+1)$^+$.

Intermediate 108 trans-4-(methyl{3-[2-oxo-6-(2-oxoethyl)-1,3-benzoxazol-3(2H)-yl]propyl}amino)cyclohexyl hydroxy(di-2-thienyl)acetate To a solution of trans-4-[{3-[6-[(E/Z)-2-methoxyvinyl]-2-oxo-1,3-benzoxazol-3(2H)-yl]propyl}(methyl)amino]cyclohexyl hydroxy(di-2-thienyl)acetate (Intermediate 107, 500 mg, 0.86 mmol) in THF (5 mL) was added dropwise a solution of HCl (0.45 mL of a 4M solution in dioxane, 1.8 mmol) and the mixture was stirred for 1 hour. Aqueous sodium bicarbonate was added and the aqueous layer was extracted with CH$_2$Cl$_2$ (3×30 mL). The resulting organic phase was washed with water and brine (30 mL each), dried over anhydrous sodium sulphate, filtered and concentrated under reduced pressure to afford the title compound as a brownish oil (545 mg (90% purity by HPLC, 100% yield). The crude was immediately used without further purification.

LRMS (m/z): 542 (M+18)$^+$, 556 (M+32)$^+$.

Intermediate 109 trans-4-[{3-[6-(2-{[(2R)-2-{[tert-butyl(di methyl)silyl]oxy}-2-(8-hydroxy-2-oxo-1,2-dihydroquinolin-5-yl)ethyl]amino}ethyl)-2-oxo-1,3-benzoxazol-3(2H)-yl]propyl}(methyl)amino]cyclohexyl hydroxy(di-2-thienyl)acetate To a solution of trans-4-(methyl{3-[2-oxo-6-(2-oxoethyl)-1,3-benzoxazol-3(2H)-yl]propyl}amino)cyclohexyl hydroxy(di-2-thienyl)acetate (Intermediate 108, 487 mg, 0.86 mmol) in 1,2-dichlorethane (8 mL) was added 5-((1R)-2-amino-1-{[tert-butyl(dimethyl)-silyl]oxy}ethyl)-8-hydroxyquinolin-2(1H)-one acetate (prepared according to preparation 8 from US20060035931, 347 mg, 0.88 mmol). The suspension was stirred for 10 min and sodium cyanoborohydride was added (145 mg, 2.31 mmol). A few drops of MeOH were also added to the reaction mixture and stirring was maintained for 18 hours. Chloroform and saturated aqueous sodium bicarbonate solution were added and the phases separated and remaining insoluble solid was kept in the flask. The aqueous phase was extracted with chloroform (3×50 mL) and the organic layer was dried over anhydrous sodium sulphate, filtered and concentrated under reduced pressure obtaining a brown solid residue. The insoluble solid was dissolved in MeOH and joined to the solid residue and the mixture was purified initially by column chromatography over silica gel eluting with chloroform:EtOH (from 0 to 100% EtOH) followed by reverse phase column chromatography over C18 modified silica gel eluting with water:MeOH (from 0 to 100% MeOH) to give the title compound as a yellowish solid (170 mg, 22% yield).

LRMS (m/z): 888 (M+1)$^+$.

Example 19 trans-4-[{3-[6-(2-{[(2R)-2-hydroxy-2-(8-hydroxy-2-oxo-1,2-dihydroquinolin-5-yl)ethyl]amino}ethyl)-2-oxo-1,3-benzoxazol-3(2H)-yl]propyl}(methyl)amino]cyclohexyl hydroxy(di-2-thienyl)acetate dihydrofluoride Obtained as a pale yellow solid (67 mg, 85% yield) from trans-4-[{3-[6-(2-{[(2R)-2-{[tert-butyl(dimethyl)silyl]oxy}-2-(8-hydroxy-2-oxo-1,2-dihydroquinolin-5-yl)ethyl]amino}ethyl)-2-oxo-1,3-benzoxazol-3(2H)-yl]propyl}(methyl)amino]cyclohexyl hydroxy(di-2-thienyl)acetate (Intermediate 109, 100 mg of a 70% purity, 0.08 mmol), and triethylamine trihydrofluoride (55 μL, 0.34 mmol) following the experimental procedure described for the synthesis of Example 1.

LRMS (m/z): 812 (M+1)$^+$.

$^1$H NMR (300 MHz, dmso) δ 8.16 (d, J=10.0 Hz, 1H), 7.45 (dd, J=5.0, 1.2 Hz, 2H), 7.26-7.12 (m, 3H), 7.10-7.02 (m, 3H), 7.00-6.82 (m, 3H), 6.50 (d, J=9.9 Hz, 1H), 5.10 (s, 1H), 4.66 (bs, 2H), 3.81 (bs, 2H), 2.9-2.5 (m, 2H), 2.43 (bs, 2H), 2.11 (s, 3H), 1.90 (bs, 2H), 1.79 (bs, 4H), 1.65 (bs, 4H), 1.35 (bs, 4H).

Intermediate 110

Ethyl[4-(2-oxopropyl)phenoxy]acetate 1-(4-hydroxyphenyl)propan-2-one (500 mg, 3.33 mmol), ethyl 2-bromoacetate (0.37 mL, 3.34 mmol) and potassium carbonate (575 mg, 4.16 mmol) were dissolved in acetonitrile (7 mL) in a sealed tube under argon atmosphere. The reaction mixture was heated to 90° C. for 3.5 hours. The solids were filtered and washed with additional acetonitrile and the filtrate was concentrated under reduced pressure to give the title compound (790 mg, 100% yield).

LRMS (m/z): 237 (M+1)$^+$.

Intermediate 111

[4-(2-oxopropyl)phenoxy]acetic acid

To a solution of ethyl[4-(2-oxopropyl)phenoxy]acetate (Intermediate 110, 786 mg, 3.33 mmol) in THF (24 mL)

water was added (12 mL) and the mixture was stirred for 10 min. Then, lithium hydroxide monohydrate (420 mg, 10.01 mmol) was added and stirring was continued for 3.5 hours at room temperature. THF was evaporated from the reaction mixture and water was added (25 mL). The solution was acidified with 5N HCl until pH 2 was reached and the aqueous phase was extracted with $CH_2Cl_2$ (3×30 mL). The resulting organic extract was washed with water and brine, dried over anhydrous sodium sulphate, filtered and concentrated under reduced pressure to give the title compound (392 mg, 57% yield).

LRMS (m/z): 209 (M+1)$^+$.

Intermediate 112 trans-4-{methyl[2-({[4-(2-oxopropyl)phenoxy]acetyl}amino)ethyl]amino}cyclohexyl hydroxy(di-2-thienyl)acetate To a solution of trans-4-[(2-aminoethyl)(methyl)amino]cyclohexyl hydroxy(di-2-thienyl)acetate (Intermediate 49, 266 mg, 0.57 mmol) in DMF (9 mL) were added [4-(2-oxopropyl)phenoxy]acetic acid (Intermediate 111, 131 mg, 0.63 mmol), DIEA (0.4 mL, 2.3 mmol) and HATU (430 mg, 1.13 mmol), and the reaction mixture was stirred at room temperature, under argon atmosphere, for 18 hours. The solvent is removed under reduced pressure and water was added to the solid residue. The aqueous phase was extracted with AcOEt (2×50 mL) and the combined organic extracts were washed with brine, dried over anhydrous sodium sulphate, filtered and concentrated to dryness. The residue obtained was purified by column chromatography over silica gel eluting with a mixture of $CH_2Cl_2$:EtOH (from 0 to 10% of EtOH) to provide the title compound (281 mg, 85% yield).

LRMS (m/z): 585 (M+1)$^+$.

Intermediate 113 trans-4-[[2-({[4-(2-{[(2R)-2-{[tert-butyl(dimethyl)silyl]oxy}-2-(8-hydroxy-2-oxo-1,2-dihydroquinolin-5-yl)ethyl]amino}propyl)phenoxy]acetyl}amino)ethyl](methyl)-amino]cyclohexyl hydroxy(di-2-thienyl)acetate Obtained as a solid (137 mg, 32% yield) from trans-4-{methyl[2-({[4-(2-oxopropyl)phenoxy]acetyl}amino)ethyl]amino}cyclohexyl hydroxy(di-2-thienyl)acetate (Intermediate 112, 280 mg, 0.48 mmol), 5-((1 R)-2-amino-1-{[tert-butyl(dimethyl)-silyl]oxy}ethyl)-8-hydroxyquinolin-2(1H)-one acetate (prepared according to preparation 8 from US20060035931, 205 mg, 0.52 mmol) and sodium triacetoxyborohydride (325 mg, 1.53 mmol) following the experimental procedure described for the synthesis of Intermediate 10 using only MeOH as solvent (4 mL). The crude obtained was purified by column chromatography over silica gel, eluting with a mixture of $CH_2Cl_2$:EtOH (from 0 to 90% of EtOH).

LRMS (m/z): 843 (M+1)$^+$.

Example 20 trans-4-{[2-({2-[4-(2-{[(2R)-2-hydroxy-2-(8-hydroxy-2-oxo-1,2-dihydroquinolin-5-yl)ethyl]amino}propyl)phenoxy]acetyl}amino)ethyl]amino}cyclohexyl hydroxy(di-2-thienyl)acetate dihydrofluoride Obtained as a pale yellow solid (967 mg, 78% yield) from trans-4-[[2-({[4-(2-{[(2R)-2-{[tert-butyl(dimethyl)silyl]oxy}-2-(8-hydroxy-2-oxo-1,2-dihydroquinolin-5-yl)ethyl]amino}propyl)phenoxy]acetyl}amino)ethyl](methyl)amino]cyclohexyl hydroxy(di-2-thienyl)acetate (Intermediate 113, 135 mg, 0.15 mmol), and triethylamine trihydrofluoride (60 µL, 0.38 mmol) following the experimental procedure described for the synthesis of Example 1.

LRMS (m/z): 812 (M+1)$^+$.

$^1$H NMR (300 MHz, cd3od) δ 8.33 (t, J=9.9 Hz, 1H), 7.35 (bs, 2H), 7.32-7.15 (m, 2H), 7.10 (bs, 3H), 6.99 (d, J=23.2 Hz, 4H), 6.67 (d, J=9.9 Hz, 1H), 5.37 (bs, 1H), 4.83 (bs, 2H), 4.52 (bs, 2H), 3.59 (bs, 2H), 3.48 (bs, 2H), 3.27-2.99 (m, 5H), 2.80-2.59 (m, 3H), 2.06 (bs, 4H), 1.69-1.39 (m, 4H), 1.33-1.14 (m, 2H).

Example 21 trans-4-[{3-[5-({[(2R)-2-hydroxy-2-(4-hydroxy-2-oxo-2,3-dihydro-1,3-benzothiazol-7-yl)ethyl]amino}methyl)-1H-1,2,3-benzotriazol-1-yl]propyl}(methyl)amino]-cyclohexyl (2S)-cyclopentyl (hydroxy)2-thienylacetate Obtained as a colourless foam (8 mg, 6% yield) from trans-4-[[3-(5-formyl-1H-1,2,3-benzotriazol-1-yl)propyl](methyl)amino]cyclohexyl (2S)-cyclopentyl (hydroxy)2-thienylacetate (Intermediate 100, 151 mg of a 70% purity, 0.2 mmol), 7-[(1 R)-2-amino-1-hydroxyethyl]-4-hydroxy-3H-benzothiazol-2-one, acetate salt (prepared according to step d of Example 1 from patent WO2009/098448, 49 mg, 0.17 mmol) and sodium triacetoxyborohydride (68 mg, 0.32 mmol) following the experimental procedure described for the synthesis of Intermediate 113. The reaction mixture was purified by reverse phase column chromatography over C18 modified silica gel eluting with water:MeOH (from 0 to 100% MeOH)

LRMS (m/z): 729 (M+1)$^+$.

$^1$H NMR (300 MHz, dmso) δ 7.90 (s, 1H), 7.77 (d, J=8.4 Hz, 1H), 7.51 (d, J=7.8 Hz, 1H), 7.37 (s, 1H), 7.05 (s, 1H), 6.95 (d, J=3.8 Hz, 1H), 6.86 (d, J=8.2 Hz, 1H), 6.69 (d, J=8.4 Hz, 1H), 5.91 (bs, 1H), 5.44 (bs, 2H), 4.62 (bs, 3H), 4.57 (bs, 2H), 3.87 (bs, 1H), 2.68 (bs, 2H), 2.37 (s, 3H), 2.12 (bs, 2H), 1.96 (bs, 3H), 1.78 (bs, 1H), 1.59 (bs, 2H), 1.31 (bs, 12H).

Biological Tests

Test 1: Human Adrenergic $\beta_1$ and $\beta_2$ Receptor Binding Assays

The study of binding to human adrenergic beta1 and beta2 receptors was performed using commercial membranes prepared from Sf9 cells where they are overexpressed (Perkin Elmer). The membrane suspensions (16 µg/well for beta1 and 5 µg/well for beta2) in assay buffer (75 mM Tris/HCl with 12.5 mM MgCl2 and 2 mM EDTA pH=7.4) were incubated with 0.14 or 0.6 nM of 3H-CGP12177 (Amersham) for beta 1 and beta 2 receptors respectively in a final volume of 250 µl, in GFC Multiscreen 96 well plates (Millipore) previously treated with assay buffer containing 0.3% PEI (Sigma). Non specific binding was measured in the presence of 1 µM propanolol. Incubation was maintained for 60 minutes at room temperature and with gentle shaking. The binding reactions were terminated by filtration and washing with 2.5 volumes of Tris/HCl 50 mM pH=7.4. The affinity of each test compound to the receptor was determined by using ten different concentrations ran in duplicate. IC50s were calculated using Activity Base software from IDBS and the four parameters-log equation.

Test 2: Human Muscarinic $M_1$, $M_2$, $M_3$, $M_4$ and $M_5$ Receptors Binding Assays The study of binding to human muscarinic M1, M2, M3, M4 and M5 receptors was performed using commercial membranes (Perkin Elmer) prepared from CHO-K1 cells. Radioligand binding experiments were conducted in 96 polypropylene well plates in a total volume of 200 µl. All reagents were dissolved in assay binding buffer (PBS with calcium and magnesium, SIGMA), except compounds that were dissolved in DMSO 100%. Non-specific binding (NSB) was measured in the presence of 1 µM atropine. [3H]-NMS was used as the radioligand at a concentration of 1 nM for M2, M3 and M5 and 0.3 nM for M1 and M4. [3H]-NMS and antagonists were incubated with membranes that express human muscarinic receptors M1, M2, M3, M4 and M5 at concentrations of 8.1, 10, 4.9, 4.5 and 4.9 µg/well, respectively.

After an incubation period of two hours with gentle shaking, 150 µl of the reaction mix were transferred to 96 GF/C filter plates (Millipore), previously treated with wash buffer (Tris 50 mM; NaCl 100 mM; pH:7.4), containing 0.05% PEI (Sigma) during one hour.

Bound and free [3H]-NMS were separated by rapid vacuum filtration in a manifold from Millipore and washed four times with ice cold wash buffer. After drying 30 min, 30 µl of OPTIPHASE Supermix were added to each well and radioactivity quantified using a Microbeta microplate scintillation counter.

The affinity of each test compound to the receptors was determined by using ten different concentrations ran in duplicate. IC50s were calculated using Activity Base software from IDBS and the four parameters-log equation.

| Example | Binding IC$_{50}$, nM | |
|---|---|---|
| | $\beta_2$ | $M_3$ |
| 1 | 140 | 0.3 |
| 2 | 120 | 0.4 |
| 4 | 220 | 0.6 |
| 5 | 2.7 | 0.4 |
| 6 | 34 | 1.4 |
| 8 | 18 | 2.2 |
| 9 | 2.2 | 0.2 |
| 10 | 5.7 | 0.4 |
| 11 | 4.2 | 0.5 |
| 15 | 1.5 | 1 |
| 16 | 12 | 5.9 |
| 17 | 13 | 0.6 |
| 18 | 1.4 | 0.4 |
| 19 | 62 | 0.8 |
| 20 | 3.1 | 3.6 |

Pharmaceutical Compositions

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Pharmaceutical compositions according to the present invention comprise the compounds of the invention in association with a pharmaceutically acceptable diluent or carrier.

As used herein, the term pharmaceutical composition refers to a mixture of one or more of the compounds described herein, or physiologically/pharmaceutically acceptable salts, solvates, N-oxides, isomers, isotopes, polymorphs or prodrugs thereof, with other chemical components, such as physiologically/pharmaceutically acceptable carriers and excipients. The purpose of a pharmaceutical composition is to facilitate administration of a compound to an organism.

As used herein, a physiologically/pharmaceutically acceptable diluent or carrier refers to a carrier or diluent that does not cause significant irritation to an organism and does not abrogate the biological activity and properties of the administered compound.

A pharmaceutically acceptable excipient refers to an inert substance added to a pharmaceutical composition to further facilitate administration of a compound.

The invention further provides pharmaceutical compositions comprising the compounds of the invention in association with a pharmaceutically acceptable diluent or carrier together with one or more other therapeutic agents such as the previously described for use in the treatment of a pathological condition or disease associated with both β2 adrenergic receptor agonist and muscarinic receptor antagonist activities.

The invention is also directed to pharmaceutical compositions of the invention for use in the treatment of a pathological disease or disorder associated with both β2 adrenergic receptor agonist and muscarinic receptor antagonist activities, in particular wherein the pathological disease or disorder is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis.

The invention also provides a method of treatment of a pathological condition or disease associated with both β2 adrenergic receptor agonist and muscarinic receptor antagonist activities in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis, comprising administering a therapeutically effective amount of a pharmaceutical composition of the invention.

The present invention also provides pharmaceutical compositions which comprise, as an active ingredient, at least a compound of formula (I) or a pharmaceutically acceptable salt, solvate, N-oxide or deuterated derivative thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, inhalation, topical, nasal, rectal, percutaneous or injectable administration.

Pharmaceutical compositions suitable for the delivery of compounds of the invention and methods for their preparation will be readily apparent to those skilled in the art. Such compositions and methods for their preparation can be found, for example, in Remington: The Science and Practice of Pharmacy, 21 st Edition, Lippincott Williams & Wilkins, Philadelphia, Pa., 2001.

The pharmaceutically acceptable excipients which are admixed with the active compound or salts of such compound, to form the compositions of this invention are well-known per se and the actual excipients used depend inter alia on the intended method of administering the compositions. Examples, without limitation, of excipients include calcium carbonate, calcium phosphate, various sugars and types of starch, cellulose derivatives, gelatin, vegetable oils and polyethylene glycols.

Additional suitable carriers for formulations of the compounds of the present invention can be found in Remington: The Science and Practice of Pharmacy, 21st Edition, Lippincott Williams & Wilkins, Philadelphia, Pa., 2001; or in Handbook of Pharmaceutical Excipients, $6^{th}$ ed., published by Pharmaceutical Press and American Pharmacists Association, 2009.

i) Oral Administration

The compounds of the invention may be administered orally (peroral administration; per os (latin)). Oral administration involve swallowing, so that the compound is absorbed from the gut and delivered to the liver via the portal circulation (hepatic first pass metabolism) and finally enters the gastrointestinal (GI) tract.

Compositions for oral administration may take the form of tablets, retard tablets, sublingual tablets, capsules, inhalation aerosols, inhalation solutions, dry powder inhalation, or liquid preparations, such as mixtures, solutions, elixirs, syrups or suspensions, all containing the compound of the invention; such preparations may be made by methods well-known in the art. The active ingredient may also be presented as a bolus, electuary or paste.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant. Tablet blends may be compressed directly or by roller to form tablets. Tablet blends or portions of blends may alternatively be wet-, dry-, or melt-granulated, melt congealed, or extruded before tabletting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., 1980.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Solid formulations for oral administration may be formulated to be immediate and/or modified release. Modified release formulations include delayed-, sustained-, pulsed-, controlled-, targeted and programmed release.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent. Liquid formulations may also be prepared by the reconstitution of a solid, for example, from a sachet.

ii) Oral Mucosal Administration

The compounds of the invention can also be administered via the oral mucosal. Within the oral mucosal cavity, delivery of drugs is classified into three categories: (a) sublingual delivery, which is systemic delivery of drugs through the mucosal membranes lining the floor of the mouth, (b) buccal delivery, which is drug administration through the mucosal membranes lining the cheeks (buccal mucosa), and (c) local delivery, which is drug delivery into the oral cavity.

Pharmaceutical products to be administered via the oral mucosal can be designed using mucoadhesive, quick dissolve tablets and solid lozenge formulations, which are formulated with one or more mucoadhesive (bioadhesive) polymers (such as hydroxy propyl cellulose, polyvinyl pyrrolidone, sodium carboxymethyl cellulose, hydroxy propyl methyl cellulose, hydroxy ethyl cellulose, polyvinyl alcohol, polyisobutylene or polyisoprene); and oral mucosal permeation enhancers (such as butanol, butyric acid, propranolol, sodium lauryl sulphate and others)

iii) Inhaled Administration

The compounds of the invention can also be administered by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 0.0001-10 mg, more preferably 0.001-2 mg of active ingredient or the equivalent amount of a pharmaceutically acceptable salt thereof. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described the following patent applications Nos: WO97/000703, WO03/000325 and WO2006/008027.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (Ex. WO 97/000703). For such semi-permanent multi dose inhalers with disposable drug containers, the requirements to prevent drug accumulation are even more strict.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with. Such atomiser is the Respimat® which is described, for example, in PCT Patent Applications Nos. WO 91/14468 and WO 97/12687, reference here is being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant.

The aerosol composition may be excipient free or may optionally contain additional formulation excipients well known in the art such as surfactants (eg oleic acid or lecithin) and cosolvens (eg ethanol). Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e.g. a fluorocarbon polymer as described in WO96/32150. Canisters will be fitted into an actuator adapted for buccal delivery.

iv) Nasal Mucosal Administration

The compounds of the invention may also be administered via the nasal mucosal. Typical compositions for nasal mucosa administration are typically applied by a metering, atomizing spray pump and are in the form of a solution or suspension in an inert vehicle such as water optionally in combination with conventional excipients such as buffers, anti-microbials, tonicity modifying agents and viscosity modifying agents.

v) Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art. The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

vi) Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and microneedle or needle-free injection.

Formulations for topical administration may be formulated to be immediate and/or modified release. Modified release formulations include delayed-, sustained-, pulsed-, controlled-, targeted and programmed release.

vii) Rectal/Intravaginal Administration

Compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

viii) Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable {e.g. absorbable gel sponges, collagen) and nonbiodegradable (e.g. silicone) implants, wafers, lenses and particulate or vesicular systems, such as niosomes or liposomes. A polymer such as crossed-linked polyacrylic acid, polyvinyl-alcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

ix) Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

The amount of the active compound administered will be dependent on the subject being treated, the severity of the disorder or condition, the rate of administration, the disposition of the compound and the discretion of the prescribing physician. However, an effective dosage is typically in the range of 0.01-3000 μg, more preferably 0.5-1000 μg of active ingredient or the equivalent amount of a pharmaceutically acceptable salt thereof per day. Daily dosage may be administered in one or more treatments, preferably from 1 to 4 treatments, per day.

The pharmaceutical formulations may conveniently be presented in unit dosage form and may be prepared by any of the methods well known in the art of pharmacy. Preferably the composition is in unit dosage form, for example a tablet, capsule or metered aerosol dose, so that the patient may administer a single dose.

The active substance compositions according to the invention are preferably administered in the form of compositions for inhalation delivered with the help of inhalers, especially dry powder inhalers; however, any other form of nasal, topical, parenteral or oral application is possible. Here, the application of inhaled compositions embodies one of the preferred application form, especially in the therapy of obstructive lung diseases or for the treatment of asthma.

Combinations

The compounds of the invention can also be used in combination with other drugs known to be effective in the treatment of the diseases or the disorders indicated above. For example the compounds of the present invention can be combined with a corticosteroid and/or with a PDE4 inhibitor.

Accordingly, another embodiment of the invention is a combination product comprising
(i) at least a compound as defined previously, and
(ii) one or more active ingredients selected from the group consisting of a corticosteroid and a PDE4 inhibitor,
for simultaneous, separate or sequential use in the treatment of the human or animal body.

A preferred embodiment of the invention is a combination product as defined before for the treatment or prevention of pathological conditions, diseases and disorders associated with both β2 adrenergic receptor agonist and muscarinic receptor antagonist activities in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis; as well as a method for treating a subject afflicted with a pathological condition or disease associated with both β2 adrenergic receptor agonist and muscarinic receptor antagonist activities, in particular wherein the pathological condition or disease is selected from a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis; preferably asthma and chronic obstructive pulmonary disease, which comprises administering to said subject an effective amount of a combination product as defined before.

As indicated above, the compounds or pharmaceutically acceptable salts, solvates, N-oxides, isomers, isotopes, polymorphs or prodrugs thereof, according to the invention may also be used in combination with another therapeutically active agent, for example a corticosteroid and/or with a PDE4 inhibitor.

The amount of each active which is required to achieve a therapeutic effect will, of course, vary with the particular active, the route of administration, the subject under treatment, and the particular disease or disorder being treated.

The active ingredients may be administered from 1 to 6 times a day, sufficient to exhibit the desired activity. Preferably, the active ingredients are administered once or twice a day, most preferably once a day.

Examples of suitable corticosteroids and glucocorticoids that can be combined with the compounds of the invention are prednisolone, methylprednisolone, dexamethasone, dexamethasone acetate, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone, mometasone furoate, rimexolone, prednisolone farnesylate, ciclesonide, butixocort propionate, RS-85095, CGP-13774, GW-250495, deltacortisone, NO-Prednisolone, NO-Budesonide, etiprednol dicloacetate, QAE-397, 7beta-OH-EPIA, RPR-106541, deprodone propionate, fluticasone, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, 21-Chloro-11 beta-hydroxy-17alpha-[2-(methylsulfanyl)acetoxy]-4-pregnene-3,20-dione, desisobutyrylciclesonide, hydrocortisone acetate, hydrocortisone sodium succinate, prednisolone sodium phosphate and hydrocortisone probutate, prednisolone sodium metasulfobenzoate and clobetasol propionate.

Examples of suitable PDE4 inhibitors that can be combined with the compounds of the present invention are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, revamilast, ronomilast, (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-isopropyl-3H-purine hydrochloride (V-11294A), 6-[3-(N,N-

Dimethylcarbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxyethyl)pyridin-2(1H)-one (T-440), (−)-trans-2-[3′-[3-(N-Cyclopropylcarbamoyl)-4-oxo-1,4-dihydro-1,8-naphthyridin-1-yl]-3-fluorobiphenyl-4-yl]cyclopropanecarboxylic acid, MK-0873, CDC-801, GSK-356278, TA-7906, CP-80633, RPL-554, NIK-616, GPD-1116, D4396, UK-500001, BLX-914, 2-carbomethoxy-4-cyano-4-(3-cyclopropylmethoxy-4-difluoromethoxyphenyl) cyclohexanl-one, cis[4-cyano-4-(3-cyclopropylmethoxy-4-difluoromethoxyphenyl) cyclohexan-1-ol, 5(S)-[3-(Cyclopentyloxy)-4-methoxyphenyl]-3(S)-(3-methylbenzyl) piperidin-2-one (IPL-455903), ONO-6126 (Eur Respir J 2003, 22(Suppl. 45): Abst 2557) and the compounds claimed in the PCT patent applications number WO 03/097613, WO 2004/058729, WO 2005/049581, WO 2005/123693, WO 2005/123692, and WO 2010/069504.

Particularly preferred combination products according to the invention comprise a compound of the present invention and a therapeutically effective amount of one or more additional therapeutic agents selected from the group consisting of mometasone furoate, ciclesonide, budesonide, fluticasone propionate, fluticasone furoate, betamethasone valerate, clobetasol propionate, rolipram, roflumilast, oglemilast, cilomilast, arofylline, apremilast and tetomilast.

Thus, in one aspect of the invention, the combination product comprises a compound of the present invention and a corticosteroid. Particularly preferred corticosteroids are those selected from the group consisting of mometasone furoate, ciclesonide, budesonide, fluticasone furoate, fluticasone propionate, betamethasone valerate and clobetasol propionate.

In a still other aspect of the invention, the combination product comprises a compound of the present invention and a PDE4 inhibitor. Particularly preferred PDE4 inhibitors are those selected from the group consisting of rolipram, roflumilast, oglemilast, cilomilast and the compounds claimed in the PCT patent applications number WO 03/097613, WO 2004/058729, WO 2005/049581, WO 2005/123693, WO 2005/123692, and WO 2010/069504. The combination product may further comprise a corticosteroid selected from the group consisting of mometasone furoate, ciclesonide, budesonide, fluticasone furoate and fluticasone propionate.

The compounds of the present invention and the combinations of the invention may be used in the treatment of respiratory, skin and inflammatory diseases, wherein the use of a dual both β2 adrenergic receptor agonist and antimuscarinic receptor antagonist is expected to have a beneficial effect, for example a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis; preferably asthma and chronic obstructive pulmonary disease.

The active compounds in the combination product may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be administered in the morning and the other (s) later in the day. Or in another scenario, one or two actives could be administered twice daily and the other (s) once daily, either at the same time as one of the twice-a-day dosing occurred, or separately. Preferably at least two, and more preferably all, of the actives would be administered together at the same time. Preferably, at least two, and more preferably all actives would be administered as an admixture.

FORMULATION EXAMPLE

Formulation Example 1 (Oral Suspension)

| Ingredient | Amount |
| --- | --- |
| Active Compound | 3 mg |
| Citric acid | 0.5 g |
| Sodium chloride | 2.0 g |
| Methyl paraben | 0.1 g |
| Granulated sugar | 25 g |
| Sorbitol (70% solution) | 11 g |
| Veegum K | 1.0 g |
| Flavoring | 0.02 g |
| Dye | 0.5 mg |
| Distilled water | q.s. to 100 mL |

Formulation Example 2 (Hard Gelatine Capsule for Oral Administration)

| Ingredient | Amount |
| --- | --- |
| Active Compound | 1 mg |
| Lactose | 150 mg |
| Magnesium stearate | 3 mg |

Formulation Example 3 (Gelatin Cartridge for Inhalation)

| Ingredient | Amount |
| --- | --- |
| Active Compound (micronized) | 0.2 mg |
| Lactose | 25 mg |

Formulation Example 4 (Formulation for Inhalation with a DPI)

| Ingredient | Amount |
| --- | --- |
| Active Compound (micronized) | 15 mg |
| Lactose | 3000 mg |

Formulation Example 5 (Formulation for a MDI)

| Ingredient | Amount |
| --- | --- |
| Active Compound (micronized) | 10 g |
| 1,1,1,2,3,3,3-heptafluoro-n-propane | q.s. to 200 ml |

The invention claimed is:

1. A compound of formula (IV), or a pharmaceutically acceptable salt, solvate, or deuterated derivative thereof:

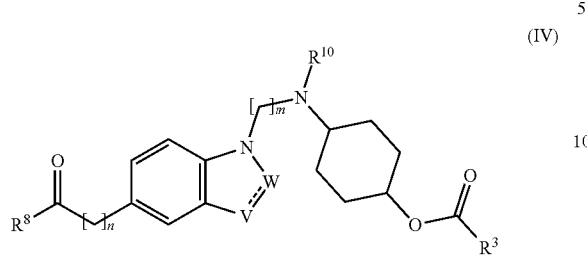
(IV)

wherein
=== is a double bond or a single bond,
wherein:
when === is a single bond, V is independently chosen from —O—, —NH—, and —S—, and W is —C(O)—, or
when === is a double bond, V and W are independently chosen from —N— and —CH—,
$R^3$ is formula:

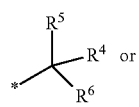
i)

or

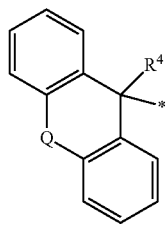
ii)

wherein:
$R^4$ is chosen from a hydrogen atom, a hydroxy group, a hydroxymethyl group, and a linear or branched $C_{1-4}$ alkyl group,
$R^5$ and $R^6$ are independently chosen from a thienyl group, a phenyl group, a benzyl group, and a $C_{4-6}$ cycloalkyl group,
Q is chosen from a direct bond or an oxygen atom,
* is a point of attachment of $R^3$ to the remainder of Formula (IV),
$R^8$ and $R^{10}$ are independently chosen from a hydrogen atom and a linear or branched $C_{1-4}$ alkyl group,
n is 0, 1 or 2, and
m is 2, 3 or 4.

2. The compound according to claim 1, wherein the compound is chosen from:
Intermediate 9: trans-4-[[3-(6-formyl-2-oxo-1,3-benzoxazol-3(2H)-yl)propyl](methyl)amino] cyclohexylhydroxy(di-2-thienyl)acetate;
Intermediate 16: trans-4-[[3-(5-formyl-2-oxo-2,3-dihydro-1H-benzimidazol-1-yl)propyl](methyl)amino] cyclohexyl hydroxy(di-2-thienyl)acetate;
Intermediate 21: trans-4-[[3-(5-formyl-1H-1,2,3-benzotriazol-1-yl)propyl](methyl)amino]cyclohexyl hydroxy(di-2-thienyl)acetate;
Intermediate 24: trans-4-[[3-(5-formyl-1H-indol-1-yl)propyl](methyl)amino]cyclohexyl hydroxy(di-2-thienyl)acetate;
Intermediate 73: trans-4-[[3-(6-formyl-2-oxo-1,3-benzothiazol-3(2H)yl)propyl](methyl)amino]cyclohexyl hydroxy(di-2-thienyl)acetate;
Intermediate 83: trans-4-[[2-(6-formyl-2-oxo-1,3-benzoxazol-3(2H)-yl)ethyl](methyl)amino]cyclohexyl hydroxy(di-2-thienyl)acetate;
Intermediate 87: trans-4-[[4-(6-formyl-2-oxo-1,3-benzoxazol-3(2H)-yl)butyl](methyl)amino]-cyclohexyl hydroxy(di-2-thienyl)acetate;
Intermediate 92: trans-4-[[3-(6-formyl-2-oxo-1,3-benzoxazol-3(2H)-yl)propyl](methyl)amino]cyclohexyl 9-methyl-9H-xanthene-9-carboxylate;
Intermediate 100: trans-4-[[3-(5-formyl-1H-1,2,3-benzotriazol-1-yl)propyl](methyl)amino]cyclohexyl (2S)-cyclopentyl(hydroxy)2-thienylacetate; and
Intermediate 108: trans-4-(methyl{3-[2-oxo-6-(2-oxoethyl)-1,3-benzoxazol-3(2H)-yl]propyl}amino)cyclohexyl hydroxy(di-2-thienyl)acetate;
or a pharmaceutically acceptable salt, solvate, or deuterated derivative thereof.

3. The compound according to claim 1, wherein the compound is Intermediate 21: trans-4-[[3-(5-formyl-1H-1,2,3-benzotriazol-1-yl)propyl](methyl)amino]cyclohexyl hydroxy(di-2-thienyl)acetate.

4. A process for the preparation of trans-4-[[3-(5-formyl-1 H-1,2,3-benzotriazol-1-yl)propyl](methyl)amino]cyclohexyl hydroxy(di-2-thienyl)acetate, Intermediate 21, comprising the step of
reacting trans-4-(methylamino)cyclohexyl hydroxy(di-2-thienyl)acetate, Intermediate 5, with a compound of formula (XIV),

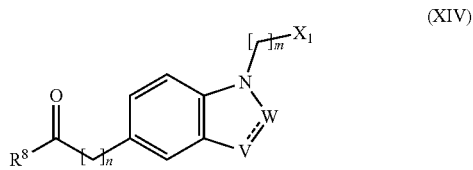
(XIV)

wherein
=== is a double bond,
V and W are nitrogen,
m is 3,
n is 0,
$R^8$ is hydrogen, and
$X_1$ is chosen from a bromine atom, a —O-methanesulfonyl group and a —O—p-toluenesulfonyl group.

5. The process of claim 4, wherein the compound of formula (XIV) is Intermediate 20: 1-(3-bromopropyl)-1H-1,2,3-benzotriazole-5-carbaldehyde.

6. The process of claim 4, wherein the compound of formula (XIV) is Intermediate 99: 3-(5-formyl-1H-1,2,3-benzotriazol-1-yl)propyl methanesulfonate.

7. The process of claim 4, wherein the reaction is carried out in an organic solvent.

8. The process of claim 7, wherein the organic solvent is acetonitrile.

9. The process of claim 4, wherein the reaction is carried out at a temperature between 75° C. to 90° C.

10. The process of claim 4, wherein the reaction is carried out in the presence of an organic base.

11. The process of claim 10, wherein the organic base is chosen from diisopropylethylamine (DIEA) and triethylamine (Et₃N).

12. A compound which is Intermediate 20: 1-(3-bromopropyl)-1H-1,2,3-benzotriazole-5-carbaldehyde or a pharmaceutically acceptable salt, solvate, or deuterated derivative thereof.

13. A compound which is Intermediate 99: 3-(5-formyl-1H-1,2,3-benzotriazol-1-yl)propyl methanesulfonate or a pharmaceutically acceptable salt, solvate, or deuterated derivative thereof.

14. A process for the preparation of a compound of formula (ID) or a pharmaceutically acceptable salt, solvate, or deuterated derivative thereof:

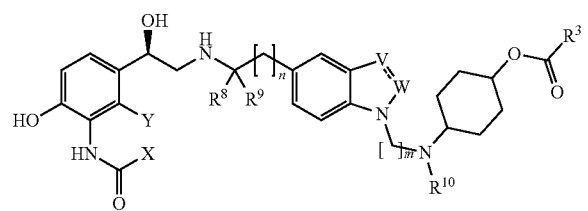

wherein
$R^9$ is hydrogen,
X and Y are independently chosen from a hydrogen atom or X together with Y forms —CH=CH—, —CH₂—CH₂—, —CH₂—O—, or —S—, wherein in the case of —CH₂—O— the methylene group is bound to the carbon atom in the amido substituent containing X and the oxygen atom is bound to the carbon atom in the phenyl ring containing Y,
comprising the step of reacting a compound of formula (IV) or a pharmaceutically acceptable salt, solvate, or deuterated derivative thereof:

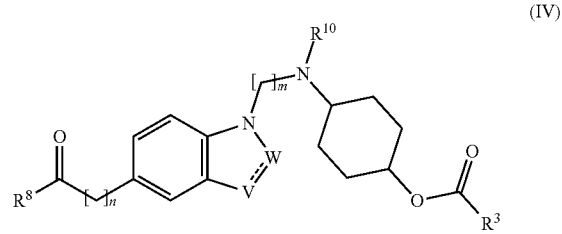

wherein
═══ is a double bond or a single bond,
wherein:
when ═══ is a single bond, V is independently chosen from —O—, —NH—, and —S—, and W is —C(O)—, or
when ═══ is a double bond, V and W are independently chosen from —N— and —CH—,
$R^3$ is formula:

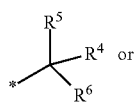

-continued

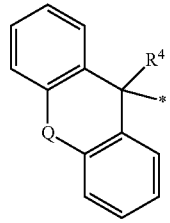

wherein:
$R^4$ is chosen from a hydrogen atom, a hydroxy group, a hydroxymethyl group, and a linear or branched $C_{1-4}$ alkyl group,
$R^5$ and $R^6$ are independently chosen from a thienyl group, a phenyl group, a benzyl group, and a $C_{4-6}$ cycloalkyl group,
Q is chosen from a direct bond and an oxygen atom,
* is a point of attachment of $R^3$ to the remainder of Formula (IV),
$R^8$ and $R^{10}$ are independently chosen from a hydrogen atom and a linear or branched $C_{1-4}$ alkyl group,
n is 0, 1 or 2, and
m is 2, 3 or 4,
with a compound of formula (III),

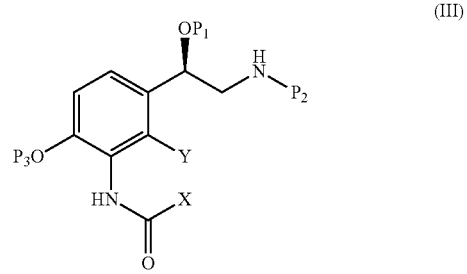

wherein $P_1$ and $P_3$ are independently chosen from a hydrogen atom or an oxygen-protecting group, and $P_2$ is chosen from a hydrogen atom or a nitrogen-protecting group.

15. The process of claim 14, wherein the oxygen-protecting group is chosen from a silyl and a benzyl ether.

16. The process of claim 14, wherein the nitrogen-protecting group is a benzyl group.

17. The process of claim 14, wherein the step of reacting a compound of formula (IV) with a compound of formula (III) is carried out in an organic solvent or a mixture of organic solvents.

18. The process of claim 17, wherein the solvent is chosen from THF, methanol, dichlorometane, 1,2-dichloroethane and DMSO.

19. The process of claim 17, wherein the mixture of solvents is chosen from THF/methanol and 1,2-dichloroethane/methanol.

20. The process of claim 14, wherein the step of reacting a compound of formula (IV) with a compound of formula (III) is carried out at a temperature between 0° C. and 60° C.

21. The process of claim 14, wherein the step of reacting a compound of formula (IV) with a compound of formula (III) is carried out in the presence of a reducing agent.

22. The process of claim 21, wherein the reducing agent is chosen from sodium borohydride, sodium triacetoxyborohydride and sodium cyanoborohydride.

23. The process of claim 14, wherein the step of reacting a compound of formula (IV) with a compound of formula (III) is carried out in the presence of a tertiary amine.

24. The process of claim 23, wherein the tertiary amine is diisopropylethylamine (DIEA).

* * * * *